United States Patent
Egawa et al.

(10) Patent No.: US 8,183,793 B2
(45) Date of Patent: May 22, 2012

(54) METHOD FOR SYNTHESIZING ANTHRACENE DERIVATIVE AND ANTHRACENE DERIVATIVE, LIGHT EMITTING ELEMENT, LIGHT EMITTING DEVICE, ELECTRONIC DEVICE

(75) Inventors: Masakazu Egawa, Tochigi (JP); Sachiko Kawakami, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 12/940,473

(22) Filed: Nov. 5, 2010

(65) Prior Publication Data

US 2011/0050118 A1 Mar. 3, 2011

Related U.S. Application Data

(62) Division of application No. 11/845,432, filed on Aug. 27, 2007, now abandoned.

(30) Foreign Application Priority Data

Aug. 30, 2006 (JP) ................. 2006-234639

(51) Int. Cl.
*H05B 37/02* (2006.01)
*C07D 209/82* (2006.01)
*C07D 209/86* (2006.01)
*H01J 1/62* (2006.01)

(52) U.S. Cl. ...................... 315/291; 428/690

(58) Field of Classification Search .......... 428/690, 428/917, 411.1, 336; 313/502–509; 257/40, 257/88, 104, E51; 532/1; 540/1
See application file for complete search history.

(56) References Cited

U.S. PATENT DOCUMENTS 5,811,834 A 9/1998 Tamano et al.
(Continued)

FOREIGN PATENT DOCUMENTS

CN 1526689 A 9/2004
(Continued)

OTHER PUBLICATIONS

International Search Report and Written Opinion for Application No. PCT/JP2006/306775, dated May 2, 2006, 7 pages.
(Continued)

*Primary Examiner* — Angela Ortiz
*Assistant Examiner* — J. L. Yang
(74) *Attorney, Agent, or Firm* — Fish & Richardson P.C.

(57) ABSTRACT

It is an object to provide a novel method for synthesizing an anthracene derivative with the small number of steps. It is another object to provide a novel anthracene derivative. It is further another object to provide a light-emitting element, a light-emitting device, and an electronic device, each using the anthracene derivative. A method for synthesizing an anthracene derivative represented by a general formula (1) is provided by coupling a 9-arylanthracene derivative having an active site at a 10-position with a 9-arylcarbazole derivative having an active site in an aryl group using metal, a metal compound, or a metal catalyst.

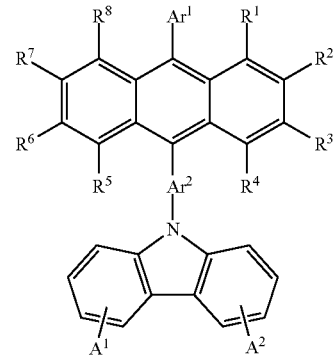

7 Claims, 55 Drawing Sheets

U.S. PATENT DOCUMENTS

| | | | |
|---|---|---|---|
| 6,482,986 | B1 | 11/2002 | Boigegrain et al. |
| 6,617,051 | B1 | 9/2003 | Higashi et al. |
| 6,713,566 | B1 | 3/2004 | Marcuccio et al. |
| 6,815,094 | B2 | 11/2004 | Lee et al. |
| 6,984,462 | B2 | 1/2006 | Kim et al. |
| 7,132,456 | B2 | 11/2006 | Gillig et al. |
| 7,161,185 | B2 | 1/2007 | Yamazaki et al. |
| 7,252,894 | B2 | 8/2007 | Yu et al. |
| 7,387,845 | B2 | 6/2008 | Saitoh et al. |
| 7,541,097 | B2 | 6/2009 | Seo et al. |
| 7,723,722 | B2 | 5/2010 | Kawakami et al. |
| 7,745,988 | B2 | 6/2010 | Sasaki et al. |
| 7,790,892 | B2 | 9/2010 | Ikeda et al. |
| 2003/0205696 | A1 | 11/2003 | Thoms et al. |
| 2004/0086745 | A1 | 5/2004 | Iwakuma et al. |
| 2004/0115476 | A1 | 6/2004 | Oshiyama et al. |
| 2004/0161633 | A1 * | 8/2004 | Seo et al. ............ 428/690 |
| 2006/0014981 | A1 | 1/2006 | Reetz et al. |
| 2006/0052449 | A1 | 3/2006 | Gillig et al. |
| 2006/0068221 | A1 | 3/2006 | Saitoh et al. |
| 2006/0115680 | A1 | 6/2006 | Hwang et al. |
| 2007/0049760 | A1 | 3/2007 | Kawakami et al. |
| 2007/0075632 | A1 | 4/2007 | Kawakami et al. |
| 2007/0106103 | A1 | 5/2007 | Ikeda et al. |
| 2007/0247063 | A1 * | 10/2007 | Murase et al. ............ 313/504 |
| 2009/0015140 | A1 | 1/2009 | Kawakami et al. |
| 2009/0102360 | A1 | 4/2009 | Kawakami et al. |
| 2010/0069647 | A1 | 3/2010 | Suzuki et al. |
| 2010/0076201 | A1 | 3/2010 | Suzuki et al. |
| 2010/0200847 | A1 | 8/2010 | Kawakami et al. |

FOREIGN PATENT DOCUMENTS

| | | | |
|---|---|---|---|
| CN | 1984897 | A | 6/2007 |
| CN | 101200634 | A | 6/2008 |
| EP | 1424381 | A2 | 6/2004 |
| EP | 1748045 | A1 | 1/2007 |
| EP | 1829871 | A1 | 9/2007 |
| JP | 2003-031371 | A | 1/2003 |
| JP | 2003-167550 | A | 6/2003 |
| JP | 2003-229273 | A | 8/2003 |
| JP | 2003-238534 | A | 8/2003 |
| JP | 2004-087363 | A | 3/2004 |
| JP | 2004-091334 | A | 3/2004 |
| JP | 2004-335427 | A | 11/2004 |
| JP | 2006-509801 | A | 3/2006 |
| JP | 2006-199679 | A | 8/2006 |
| JP | 2007-131722 | A | 5/2007 |
| WO | WO 01/23353 | A2 | 4/2001 |
| WO | WO 2004/052848 | A1 | 6/2004 |
| WO | WO 2005/113531 | A1 * | 12/2005 |
| WO | WO 2006/104221 | A1 | 10/2006 |

OTHER PUBLICATIONS

Grisorio, R et al., Novel Bifluorene Based Conjugated Systems: Synthesis and Properties; Tetrahedron, 2006, vol. 62, pp. 627-634.

Promarak. V et al., Synthesis and Properties of Stable Amorphous Hole-Transporting Molecules for Electroluminescent Devices, Tetrahedron Letters, 2006, vol. 47, No. 50, pp. 8949-8952.

European Search Report for Application No. 08003826.8, dated Jul. 14, 2008, 7 pages.

Kim, S et al., Synthesis and Hole-Transporting Properties of Phenyl-Carbazyl Derivatives; Molecular Crystals & Liquid Crystals, 2008, vol. 491, pp. 133-144.

International Search Report and Written Opinion for Application No. PCTJP2009062568, dated Aug. 11, 2009, 6 pages.

European Search Report for Application No. 09169453.9, dated Nov. 3, 2009, 4 pages.

European Search Report for Application No. 06730723.1, dated Jan. 26, 2010, 6 pages.

Chinese Office Action for Application No. 200680018801.4, dated Apr. 15, 2010, 25 pages.

Li, J-H.; Wang, D-P. Eur. J. Org. Chem. 2006, 2063-2066.

PCT International Search Report (Application No. PCT/JP2007/066706) mailed Oct. 16, 2007 (4 pages).

PCT Written Opinion (Application No. PCT/JP2007/066706) mailed Oct. 16, 2007 (5 pages).

Chinese Office Action for Application No. 200680018801.4, dated Apr. 15, 2010, with full English translation, 25 pages.

Chinese Office Action for Application No. 200780031662.3, dated Apr. 6, 2011, with full English translation, 15 pages.

* cited by examiner

Light-Emitting Element 4

— Initial
— After 100 Cycles

METHOD FOR SYNTHESIZING ANTHRACENE DERIVATIVE AND ANTHRACENE DERIVATIVE, LIGHT EMITTING ELEMENT, LIGHT EMITTING DEVICE, ELECTRONIC DEVICE

CROSS-REFERENCE TO RELATED APPLICATIONS

This application is a divisional of U.S. application Ser. No. 11/845,432, filed Aug. 27, 2007, now pending, which claims the benefit of a foreign priority application filed in Japan as Serial No. 2006-234639 on Aug. 30, 2006, both of which are incorporated by reference.

TECHNICAL FIELD

The present invention relates to a method for synthesizing an anthracene derivative. The present invention also relates to an anthracene derivative. Further, the present invention relates to a current-excitation light-emitting element, and a light-emitting device and an electronic device each having the light-emitting element.

BACKGROUND ART

In recent years, research and development have been extensively conducted on light-emitting elements using electroluminescence. As a basic structure of these light-emitting elements, a structure where a substance having a light-emitting property is interposed between a pair of electrodes is used. By application of a voltage to this element, light emission from a substance having a light-emitting property can be obtained.

Since such a light-emitting element is a self-luminous element, there are advantages such as higher visibility of a pixel than visibility of a liquid crystal display, and unnecessity of a backlight. Accordingly, such a light-emitting element is considered to be suitable as a flat panel display element. In addition, such a light-emitting element can be manufactured to be thin and light, which is a great advantage. Moreover, the light-emitting element has a feature that response speed is extremely fast.

Furthermore, since such a light-emitting element can be formed into a film form, planar light emission can be easily obtained by formation of a large-area element. This characteristic is difficult to be obtained by a point light source typified by an incandescent lamp or an LED, or a line light source typified by a fluorescent lamp. Therefore, the light-emitting element has a high utility value as a plane light source that can be applied to lighting or the like.

The light-emitting elements using electroluminescence are classified roughly in accordance with whether they use an organic compound or an inorganic compound as a substance having a light-emitting property.

In a case where a substance having a light-emitting property is an organic compound, by application of a voltage to the light-emitting element, electrons and holes are injected from the pair of electrodes into the layer including an organic compound having a light-emitting property to cause current flow. Then, by recombination of these carriers (electrons and holes), the organic compound having a light-emitting property gets in an excited state, and light is emitted when the excited state returns to a ground state. Because of such a mechanism, this kind of light-emitting element is referred to as a light-emitting element of a current excitation type.

It is to be noted that an excited state formed by an organic compound can be a singlet excited state or a triplet excited state. Light emission from the singlet excited state is referred to as fluorescence, and light emission from the triplet excited state is referred to as phosphorescence.

In order to overcome many problems derived from materials of such a light-emitting element and to improve its element characteristics, improvement in an element structure, material development, and so on are carried out.

For example, anthracene derivatives have been developed as the material used for the light-emitting elements (see Reference 1: Japanese Published Patent Application No. 2003-238534). However, in order to synthesize the anthrancene derivative disclosed in Reference 1, the plurality of steps are required to be conducted. Therefore, the yield is not favorable and a long time period for synthesis is needed.

DISCLOSURE OF INVENTION

In view of the foregoing problems, it is an object of the present invention to provide a novel method for synthesizing an anthracene derivative with the small number of steps. It is another object of the present invention to provide a novel anthracene derivative. It is further another object of the present invention to provide a light-emitting element, a light-emitting device, and an electronic device, each using the anthracene derivative.

One aspect of the present invention is a method for synthesizing an anthracene derivative represented by a general formula (1) by coupling a 9-arylanthracene derivative having an active site at a 10-position with a 9-arylcarbazole derivative having an active site in an aryl group using metal, a metal compound, or a metal catalyst.

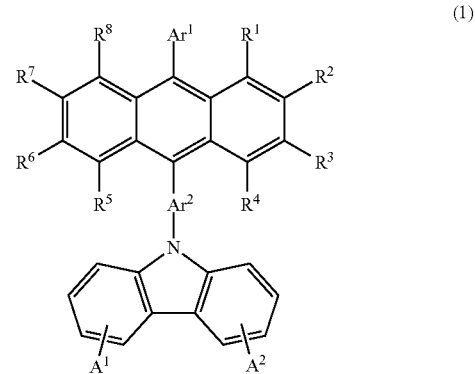

(1)

In the general formula (1), each of $R^1$ to $R^8$ represents hydrogen, an alkyl group having 1 to 4 carbon atoms, or an aryl group having 6 to 15 carbon atoms; $Ar^1$ represents an aryl group having 6 to 25 carbon atoms; $Ar^2$ represents an arylene group having 6 to 25 carbon atoms; and each of $A^1$ and $A^2$ represents hydrogen, an aryl group having 6 to 25 carbon atoms, or an alkyl group having 1 to 4 carbon atoms.

Another aspect of the present invention is a method for synthesizing an anthracene derivative represented by the general formula (1) by coupling an anthracene derivative represented by a general formula (2) with a carbazole derivative represented by a general formula (3) using metal, a metal compound, or a metal catalyst.

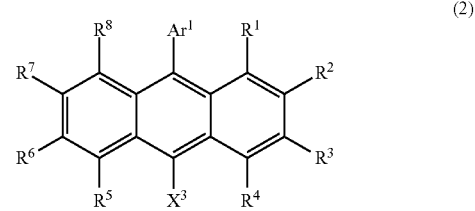

(2)

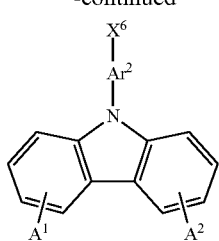

(3)

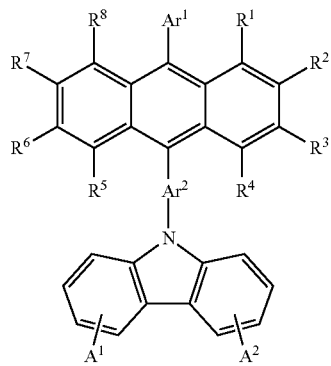

(1)

In the general formulas (1) to (3), each of $R^1$ to $R^8$ represents hydrogen, an alkyl group having 1 to 4 carbon atoms, or an aryl group having 6 to 15 carbon atoms; $Ar^1$ represents an aryl group having 6 to 25 carbon atoms; $Ar^2$ represents an arylene group having 6 to 25 carbon atoms; each of $A^1$ and $A^2$ represents hydrogen, an aryl group having 6 to 25 carbon atoms, or an alkyl group having 1 to 4 carbon atoms; and each of $X^3$ and $X^6$ represents an active site.

In the above synthesizing method, copper, iron, or the like can be given as the metal. As the metal compound, copper iodide or the like can be given. As the metal catalyst, a palladium catalyst, a nickel catalyst, or the like can be given.

In the above synthesizing method, boronic acid or organoboron is preferably coupled with halogen at the active site. That is, it is preferable that one of the active sites be boronic acid or organoboron and the other be halogen. When boronic acid or organoboron is coupled with halogen at the active site, an anthracene derivative that is a target matter can be obtained with high yield.

Another aspect of the present invention is a method for synthesizing an anthracene derivative represented by the general formula (1) by performing coupling reaction of 9-aryl-10-anthracene halide and (carbazol-9-yl)arylboronic acid using a metal catalyst.

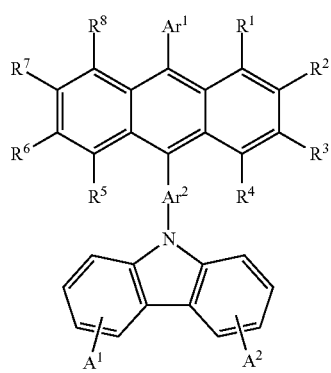

(1)

In the general formula (1), each of $R^1$ to $R^8$ represents hydrogen, an alkyl group having 1 to 4 carbon atoms, or an aryl group having 6 to 15 carbon atoms; $Ar^1$ represents an aryl group having 6 to 25 carbon atoms; $Ar^2$ represents an arylene group having 6 to 25 carbon atoms; and each of $A^1$ and $A^2$ represents hydrogen, an aryl group having 6 to 25 carbon atoms, or an alkyl group having 1 to 4 carbon atoms.

In the above synthesis method, the metal catalyst is preferably a palladium catalyst.

One aspect of the present invention is an anthracene derivative represented by a structural formula (12).

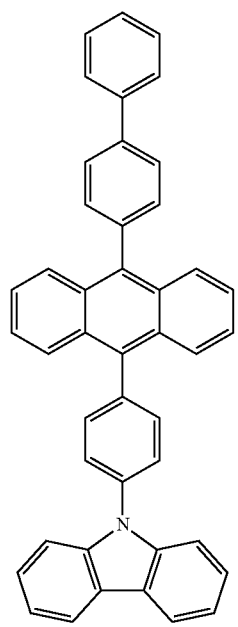

(12)

Another aspect of the present invention is an anthracene derivative represented by a structural formula (20).

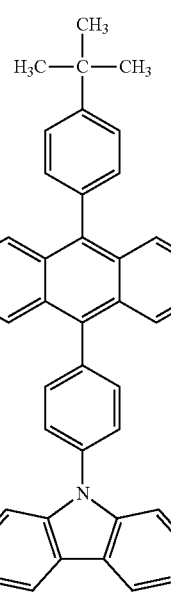

(20)

Another aspect of the present invention is an anthracene derivative represented by a structural formula (43).

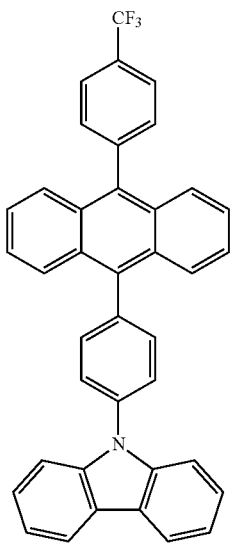

(43)

Another aspect of the present invention is an anthracene derivative represented by a structural formula (16).

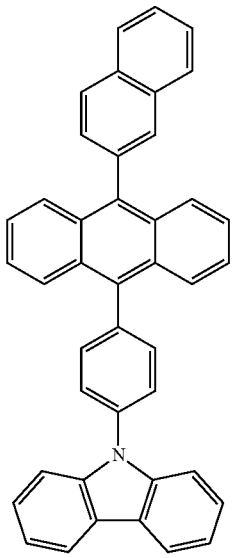

(16)

One aspect of the present invention is a light-emitting element using the above anthracene derivative. Specifically, the light-emitting element has the above anthracene derivative between a pair of electrodes.

Another aspect of the present invention is a light-emitting element having a light-emitting layer between a pair of electrodes, which has the above anthracene derivative. In particular, the above anthracene derivative is preferably used as a light-emitting substance. That is, the light-emitting element preferably has a structure in which the above anthracene derivative emits light.

A feature of the present invention is that a light-emitting device has a light-emitting element including the above anthracene derivative and a controller for controlling light emission of the light-emitting element. The light-emitting device in this specification includes an image display device, a light-emitting device, and a light source (including a lighting device). Further, the light-emitting device also includes a module in which a connector such as an FPC (Flexible Printed Circuit), a TAB (Tape Automated Bonding) tape, or a TCP (Tape Carrier Package) is attached to a panel, a module in which a printed wiring board is provided at an end of a TAB tape or a TCP, and a module in which an IC (Integrated Circuit) is directly mounted on the light-emitting device by a COG (Chip On Glass) method.

Further, an electronic device using the light-emitting element of the present invention in its display portion is also included in the category of the present invention. Therefore, the electronic device of the present invention has a display portion, and the display portion is equipped with the above-described light-emitting element and a controller for controlling light emission of the light-emitting element.

In accordance with the present invention, it becomes possible to omit synthesis steps for obtaining an anthracene derivative that is a target matter, and then, it becomes possible to synthesize an anthracene derivative more easily than the conventional case. In addition, time period needed for reaction can be shortened, which leads to cost reduction. Further, in accordance with the present invention, an anthracene derivative can be synthesized with higher yield than the conventional case.

An anthracene derivative of the present invention that has the larger band gap can emit light with a short wavelength. Further, the anthracene derivative can emit blue light with high color purity.

A light-emitting element using an anthracene derivative of the present invention can emit light with the short wavelength and blue light with high color purity.

Further, a light-emitting material having a smaller band gap than the anthracene derivative of the present invention (hereinafter, referred to as dopant) is added to a layer including the anthracene derivative of the present invention, whereby light can be obtained from the dopant. At this time, since the anthracene derivative of the present invention has an extremely large band gap, light that is not from the anthracene derivative of the present invention but from the dopant can be efficiently obtained even if dopant emitting light with relatively short wavelength is used. Specifically, by using a light-emitting material as dopant, which has emission maximum in around 450 nm of the wavelength and shows an excellent blue color purity, a light-emitting element that can obtain blue light with a high color purity can be obtained.

When a light-emitting element is manufactured, in which the anthracene derivative of the present invention is added to a layer including a material having a larger band gap than the anthracene derivative (hereinafter, refereed to as host), light from the anthracene derivative of the present invention can be obtained. In other words, the anthracene derivative of the present invention serves as dopant. At this time, since the anthracene derivative has an extremely large band gap and exhibits light with the short wavelength, a light-emitting element that can obtain blue light with a high color purity can be manufactured.

When a light-emitting material of the present invention including the anthracene derivative is used, a light-emitting element that provides an excellent color purity as blue color can be obtained. Further, when the light-emitting material of the present invention including the anthracene derivative is used, a highly reliable light-emitting element can be obtained.

A light-emitting element of the present invention including the above anthracene derivative is a light-emitting element that can provide an excellent color purity as blue light. Further, the light-emitting element of the present invention including the above anthracene derivative is a highly reliable light-emitting element.

A light-emitting device of the present invention including the light-emitting element is a light-emitting device with high color reproducibility. Further, the light-emitting device of the present invention including the light-emitting element is a highly reliable light-emitting device.

An electronic device of the present invention including the light-emitting element is an electronic device with high color reproducibility. Further, the electronic device of the present invention including the light-emitting element is a highly reliable electronic device.

BEST MODE FOR CARRYING OUT THE INVENTION

Figure 1A:
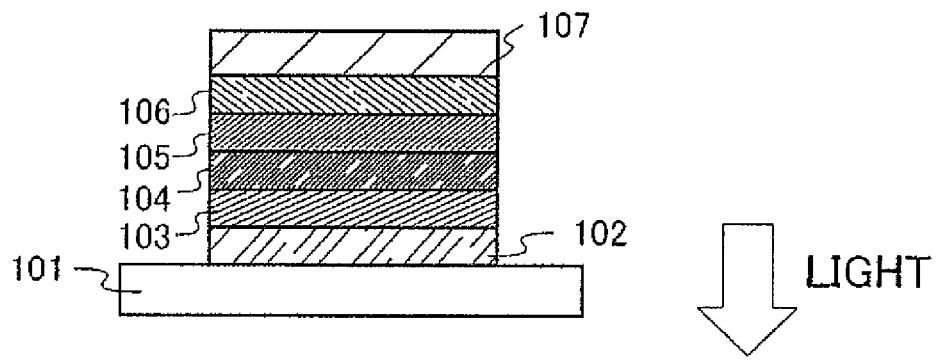
FIGS. 1A to 1C are views explaining a light-emitting element of the present invention.

Hereinafter, embodiment modes of the present invention will be described in detail with reference to the accompanying drawings. However, the present invention is not limited to the following description, and it is easily understood by those skilled in the art that various changes and modifications are possible, unless such changes and modifications depart from the content and the scope of the invention. Therefore, the present invention is not construed as being limited to the description of the following Embodiment Modes.

Embodiment Mode 1

In this embodiment mode, a method for synthesizing an anthracene derivative of the present invention will be described.

In a method for synthesizing an anthracene derivative of the present invention, a 9-arylanthracene derivative having an active site at a 10-position is coupled with a 9-arylcarbazole derivative having an active site in an aryl group using metal, a metal compound, or a metal catalyst, so that an anthracene derivative represented by a general formula (1) is synthesized.

More specifically, a 9-arylanthracene derivative having an aryl group $Ar^1$ at a 9-position and an active site at a 10-position is coupled with a 9-arylcarbazole derivative having an aryl group $Ar^2$ at a 9-position and an active site at the aryl group $Ar^2$ using metal, a metal compound, or a metal catalyst, so that an anthracene derivative represented by the general formula (1) is synthesized.

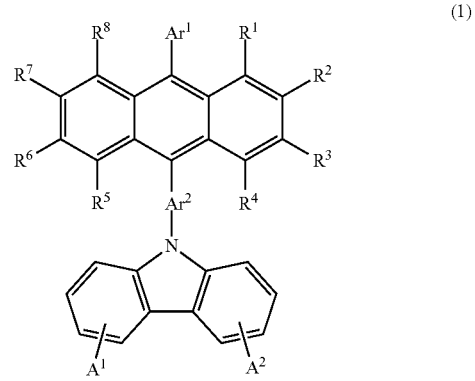

(1)

That is, an anthracene derivative represented by a general formula (2) is coupled with a carbazole derivative represented by a general formula (3) using metal, a metal compound, or a metal catalyst, so that an anthracene derivative represented by the general formula (1) can be synthesized.

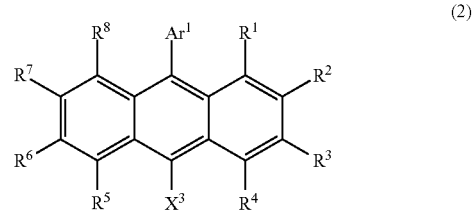

(2)

-continued

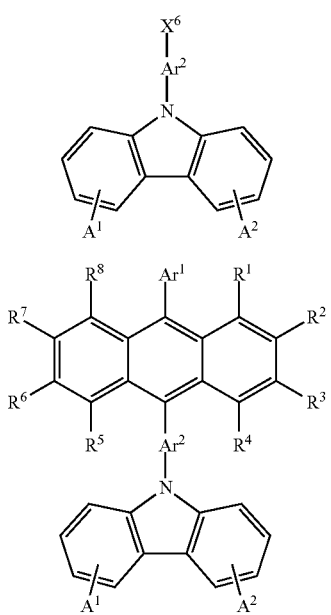

In the general formulas (1) to (3), each of $R^1$ to $R^8$ represents hydrogen, an alkyl group having 1 to 4 carbon atoms, or an aryl group having 6 to 15 carbon atoms; $Ar^1$ represents an aryl group having 6 to 25 carbon atoms; $Ar^2$ represents an arylene group having 6 to 25 carbon atoms; and each of $A^1$ and $A^2$ represents hydrogen, an aryl group having 6 to 25 carbon atoms, or an alkyl group having 1 to 4 carbon atoms. Each of $Ar^1$, $Ar^2$, $A^1$ and $A^2$ may have a substituent. As the substituent, an alkyl group having 1 to 4 carbon atoms, an aryl group having 6 to 25 carbon atoms, halogen, a haloalkyl group, a cyano group, a nitro group, an ester group, an alkoxycarbonyl group, an acyloxy group, an alkoxy group, an acyl group, a formyl group, a hydroxyl group, or the like can be given. Specifically, the following can be given: a methyl group, an ethyl group, an n-propyl group, an i-propyl group, an n-butyl group, an i-butyl group, an s-butyl group, a t-butyl group, a phenyl group, an o-tolyl group, an m-tolyl group, a p-tolyl group, a 1-naphthyl group, a 2-naphthyl group, an o-biphenylyl group, a m-biphenylyl group, a p-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a fluoren-2-yl group, a 9,9-dimethylfluoren-2-yl group, a 9,9-diphenylfluoren-2-yl group, a spiro-9,9'-bifluoren-2-yl group, fluorine, chlorine, bromine, iodine, a trifluoromethyl group, a cyano group, a nitro group, a methylester group, an ethylester group, a methoxycarbonyl group, an etoxycarbonyl group, an acetoxy group, a methoxy group, an ethoxy group, a carboxyl group, an acetyl group, an aldehyde group, or a hydroxyl group.

Further, for each of an active site $X^3$ and an active site $X^6$, halogen, boronic acid, organoboron, organotin, trifluoromethanesulfonate (triflate), a Grignard reagent, organic mercury, thiocyanate, organozinc, organoaluminum, organozirconium, or the like can be given.

As metal, a metal compound, or a metal catalyst used for reaction, metal such as copper or iron, a metal compound such as copper iodide(I), a metal catalyst such as a palladium catalyst or a nickel catalyst can be given.

A method for synthesizing an anthracene derivative of the present invention will be described in detail below. By the method for synthesizing an anthracene derivative of the present invention, coupling reaction of a 9-arylanthracene derivative (compound E) having an active site $X^3$ and a 9-arylcarbazole derivative (compound H) having an active site $X^6$ is performed using metal such as copper or iron, or a metal compound such as copper iodide(I) as shown in a synthesis scheme (A-4), so that an anthracene derivative (compound I) that is a target matter can be synthesized. The metal or the metal compound may be a metal catalyst such as a palladium catalyst or a nickel catalyst. As the coupling reaction, Suzuki-Miyaura coupling, Migita-Kosugi-Stille coupling, Kumada-Tamao coupling, Negishi coupling, or the like can be used.

(A-4)

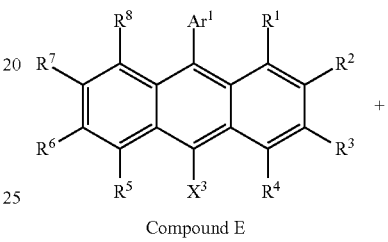

Compound E

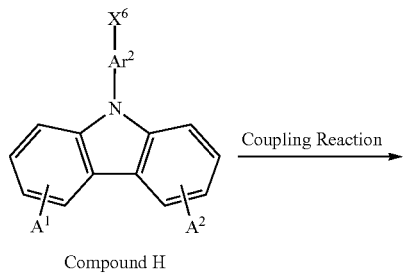

Compound H

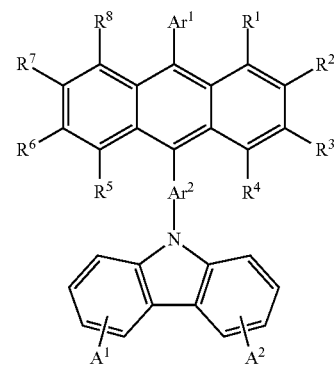

Compound I

The 9-arylanthracene derivative (compound E) having an active site $X^3$ can be synthesized by a method described below. First, as shown in a synthesis scheme (A-1), coupling reaction of an anthracene derivative (compound A) in which carbon at a 9-position such as 9-anthracene halide is active and arene (compound B) having reaction active carbon such as arylboronic acid is performed using metal such as copper or iron, a metal compound such as copper iodide(I), a metal catalyst such as a palladium catalyst or a nickel catalyst, so that a 9-arylanthracene derivative (compound C) is obtained.

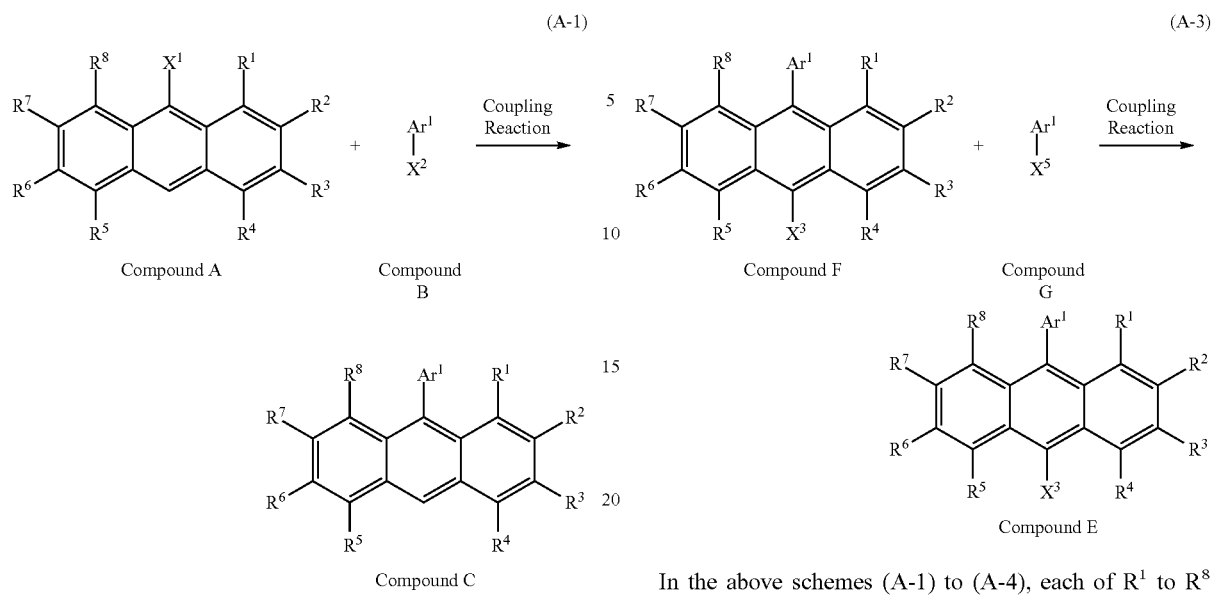

(A-1)

Compound A + Compound B →

(A-2)

Compound C →

Compound E

Next, as shown in a synthesis scheme (A-2), carbon at a 10-position is activated like halogenation of the 9-arylanthracene derivative (compound C), so that the 9-arylanthracene derivative (compound E) having an active site $X^3$ can be obtained.

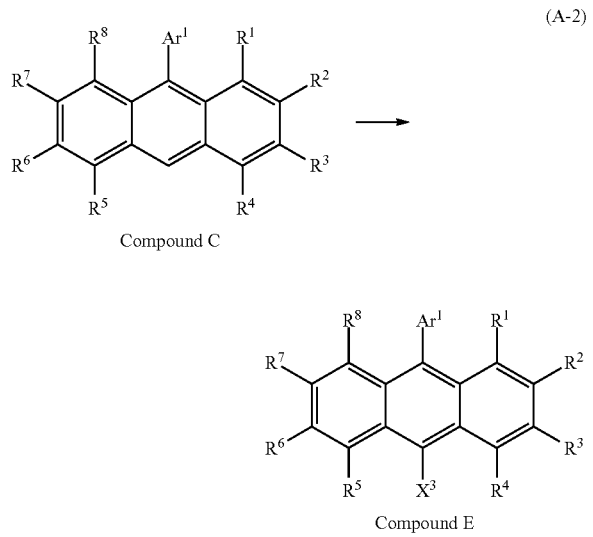

In a case where the 9-arylanthracene derivative (compound E) having an active site $X^3$ is 9-aryl-10-anthracene halide or 9-aryl-10-triflateanthracene, the synthesis can be performed by a method shown in a synthesis scheme (A-3). Specifically, an anthracene derivative (compound F) in which carbon at a 9-position and carbon at a 10-position are activated is coupled with arene (compound G) having reaction active carbon such as arylboronic acid using metal such as copper or iron, a metal compound such as copper iodide(I), a metal catalyst such as a palladium catalyst or a nickel catalyst, so that the 9-arylanthracene derivative (compound E) having an active site $X^3$ can be obtained.

In the above schemes (A-1) to (A-4), each of $R^1$ to $R^8$ represents hydrogen, an alkyl group having 1 to 4 carbon atoms, or an aryl group having 6 to 15 carbon atoms; $Ar^1$ represents an aryl group having 6 to 25 carbon atoms; $Ar^2$ represents an arylene group having 6 to 25 carbon atoms; and each of $A^1$ and $A^2$ represents hydrogen, an aryl group having 6 to 25 carbon atoms, or an alkyl group having 1 to 4 carbon atoms. Each of $Ar^1$, $Ar^2$, $A^1$ and $A^2$ may have a substituent. As the substituent, an alkyl group having 1 to 4 carbon atoms, an aryl group having 6 to 25 carbon atoms, halogen, a haloalkyl group, a cyano group, a nitro group, a carbonyl group, an ester group, an alkoxy group, or the like can be given.

In the above schemes (A-1) to (A-4), each of $X^1$ to $X^6$ represents halogen, boronic acid, organoboron, organotin, trifluoromethanesulfonate (triflate), a Grignard reagent, organic mercury, thiocyanate, organozinc, organoaluminum, or organozirconium.

Each synthesis scheme is described in detail below. In particular, specific combination of the reaction active site ($X^1$ to $X^6$) is described.

First, the synthesis scheme (A-4) is described. When Suzuki-Miyaura coupling is performed in the coupling reaction of the 9-arylanthracene derivative (compound E) having an active site $X^3$ and the 9-arylcarbazole (compound H) having an active site $X^6$ represented by the synthesis scheme (A-4), it is preferable that $X^3$ be halogen or triflate and $X^6$ be boronic acid or organoboron. Alternatively, it is preferable that $X^3$ be boronic acid or organoboron and $X^6$ be halogen or triflate. Moreover, a palladium catalyst is preferably used. When $X^3$ and $X^6$ are halogen, bromine or iodine is preferable. That is, a synthesis method shown in a synthesis scheme (A-14a) or a synthesis scheme (A-14b) is preferable.

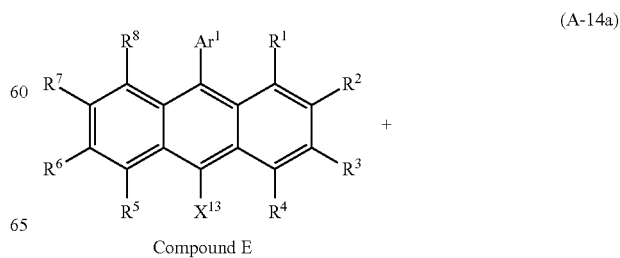

(A-14a)

Compound E +

-continued

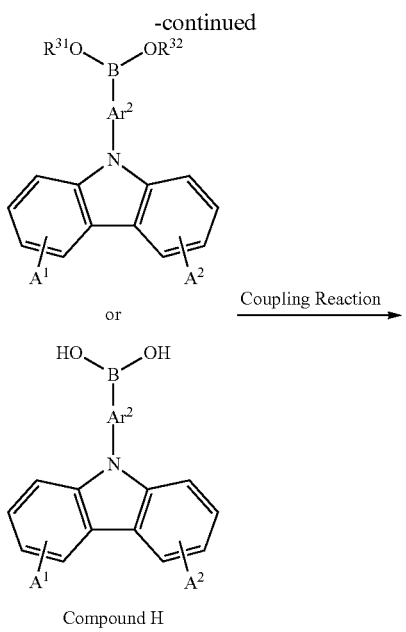

Compound H

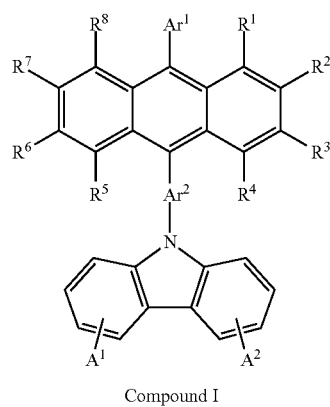

Compound I

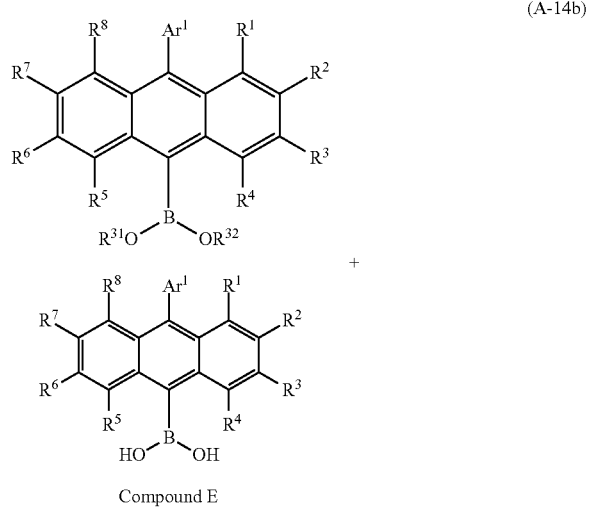

Compound E

-continued

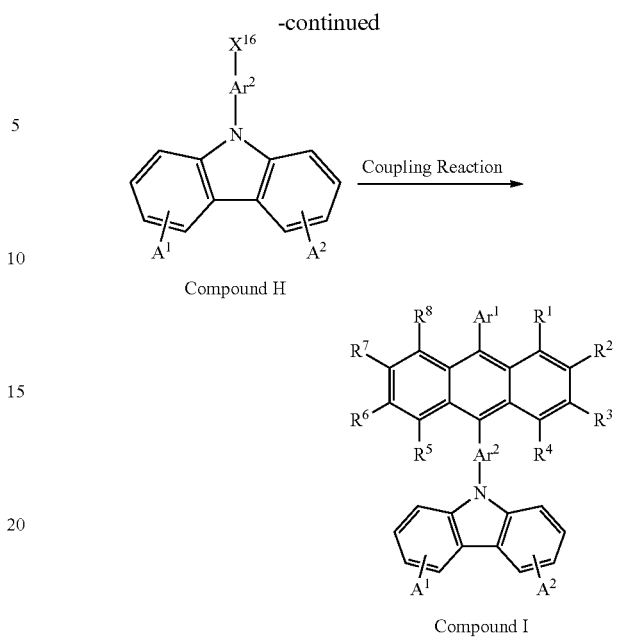

In the above schemes (A-14a) and (A-14b), each of $R^1$ to $R^8$ represents hydrogen, an alkyl group having 1 to 4 carbon atoms, or an aryl group having 6 to 15 carbon atoms; $Ar^1$ represents an aryl group having 6 to 25 carbon atoms; $Ar^2$ represents an arylene group having 6 to 25 carbon atoms; and each of $A^1$ and $A^2$ represents hydrogen, an aryl group having 6 to 25 carbon atoms, or an alkyl group having 1 to 4 carbon atoms. Each of $Ar^1$, $Ar^2$, $A^1$ and $A^2$ may have a substituent. As the substituent, an alkyl group having 1 to 4 carbon atoms, an aryl group having 6 to 25 carbon atoms, halogen, a haloalkyl group, a cyano group, a nitro group, a carbonyl group, an ester group, an alkoxy group, or the like can be given. $X^{13}$ and $X^{16}$ represent halogen, and each of $R^{31}$ and $R^{32}$ represents an alkyl group having 1 to 6 carbon atoms. It is to be noted that $R^{31}$ and $R^{32}$ are combined to form a ring.

The anthracene derivative (compound I) that is a target matter can be obtained with extremely high yield in the coupling reaction of the 9-arylanthracene derivative (compound E) having an active site $X^3$ and the 9-arylcarbazole (compound H) having an active site $X^6$ represented by the synthesis scheme (A-4); therefore, Suzuki-Miyaura coupling is preferably performed.

When $X^3$ is halogen in the coupling reaction of the 9-arylanthracene derivative (compound E) having an active site $X^3$ and the 9-arylcarbazole (compound H) having an active site $X^6$ represented by the synthesis scheme (A-4), $X^6$ is a Grignard reagent, organotin, or organic mercury. By performing coupling reaction using metal, a metal compound, or a metal catalyst such as a palladium catalyst or a nickel catalyst, the anthracene derivative (compound I) can be synthesized. Alternatively, when $X^6$ is halogen, $X^3$ is a Grignard reagent, organotin, or organic mercury. By performing coupling reaction using metal, a metal compound, or a metal catalyst such as a palladium catalyst or a nickel catalyst, the anthracene derivative (compound I) that is a target matter can be synthesized.

When $X^3$ and $X^6$ are halogen or thiocyanate in the coupling reaction of the 9-arylanthracene derivative (compound E) having an active site $X^3$ and the 9-arylcarbazole (compound H) having an active site $X^6$, the anthracene derivative (compound I) that is a target matter can be synthesized by Ullmann reaction in which copper or a copper compound is used. In the case where Ullmann reaction is performed, although $X^3$ and $X^6$ may be same or different with each other, $X^3$ and $X^6$ are preferably iodine.

Next, the synthesis scheme (A-1) is described in detail. When Suzuki-Miyaura coupling is performed in the synthesis of the 9-arylanthracene derivative (compound C) represented by the synthesis scheme (A-1), it is preferable that $X^1$ be halogen or triflate and $X^2$ be boronic acid or organoboron. For example, 9-aryl-10-anthracene halide and (carbazol-9-yl) arylboronic acid are preferably used. Alternatively, it is preferable that $X^1$ be boronic acid or organoboron and $X^2$ be halogen or triflate. Further, a palladium catalyst is preferably used. When $X^1$ and $X^2$ are halogen, bromine or iodine is preferable. That is, the synthesis scheme (A-1) is preferably a synthesis scheme (A-11a) or a synthesis scheme (A-11b).

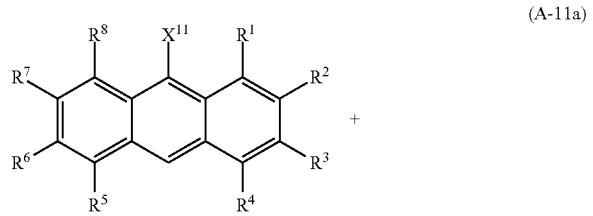

(A-11a)

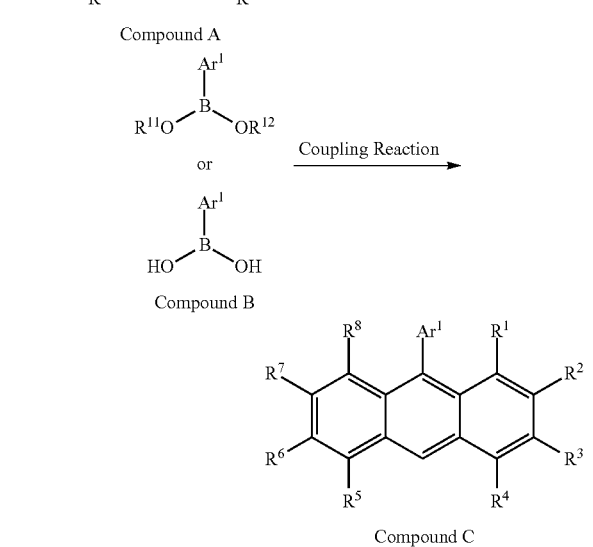

(A-11b)

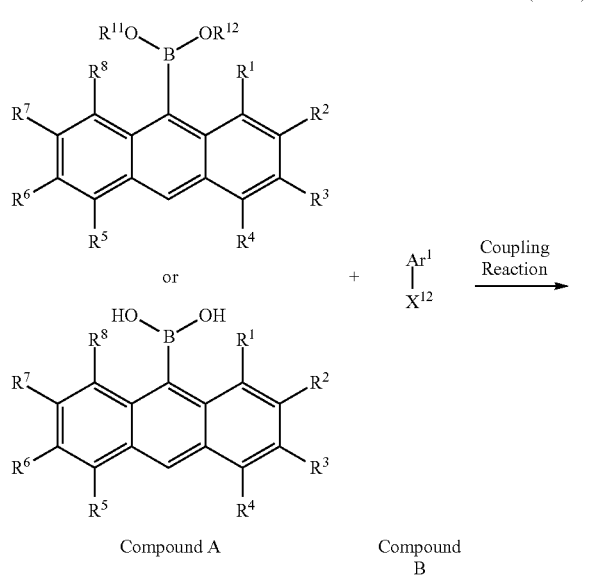

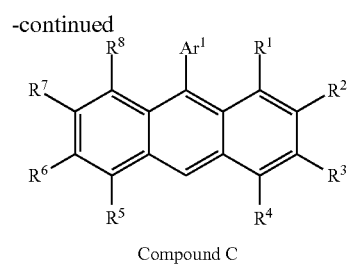

Compound C

In the above schemes (A-11a) and (A-11b), each of $R^1$ to $R^8$ represents hydrogen, an alkyl group having 1 to 4 carbon atoms, or an aryl group having 6 to 15 carbon atoms; and $Ar^1$ represents an aryl group having 6 to 25 carbon atoms. $Ar^1$ may have a substituent. As the substituent, an alkyl group having 1 to 4 carbon atoms, an aryl group having 6 to 25 carbon atoms, halogen, a haloalkyl group, a cyano group, a nitro group, a carbonyl group, an ester group, an alkoxy group, or the like can be given. $X^{11}$ and $X^{12}$ represent halogen, and each of $R^{11}$ and $R^{12}$ represents an alkyl group having 1 to 6 carbon atoms. It is to be noted that $R^{11}$ and $R^{12}$ are combined to form a ring.

The 9-arylanthracene derivative (compound C) that is a target matter can be obtained with extremely high yield in the synthesis of the 9-arylanthracene derivative (compound C) represented by the synthesis scheme (A-1); therefore, Suzuki-Miyaura coupling is preferably performed. In particular, in consideration of easiness for synthesis of materials, it is preferable that $X^1$ be halogen or triflate and $X^2$ be boronic acid or organoboron.

When $X^1$ is halogen, $X^2$ is a Grignard reagent, organotin, organic mercury, boronic acid, or organoboron. By performing coupling reaction using metal, a metal compound, or a metal catalyst such as a palladium catalyst or a nickel catalyst, the 9-arylanthracene derivative (compound C) can be synthesized. Alternatively, when $X^2$ is halogen, $X^1$ is a Grignard reagent, organotin, organic mercury, boronic acid, or organoboron. By performing coupling reaction using metal, a metal compound, or a metal catalyst such as a palladium catalyst or a nickel catalyst, the 9-arylanthracene derivative (compound C) can be synthesized.

When $X^1$ and $X^2$ are halogen or thiocyanate, the anthracene derivative (compound A) is coupled with arene (compound B) having reaction active carbon by Ullmann reaction in which copper or a copper compound is used, so that the 9-arylanthracene detivative (compound C) can be synthesized. In the case where Ullmann reaction is performed, although $X^1$ and $X^2$ may be same or different with each other, $X^1$ and $X^2$ are preferably iodine.

Next, the synthesis scheme (A-2) is described in detail. Carbon at a 10-position is activated like halogenation of the 9-arylanthracene derivative (compound C) represented by the synthesis scheme (A-12), so that the 9-arylanthracene derivative (compound B) having an active site $X^3$ can be obtained. When bromination is performed in halogenation reaction, bromination can be performed by using bromine, N-bromosuccinimide (NBS), or the like. Alternatively, when iodination is performed, iodination can be performed using iodine, orthoperiodic acid, potassium iodide, N-iodosuccinimide, or the like.

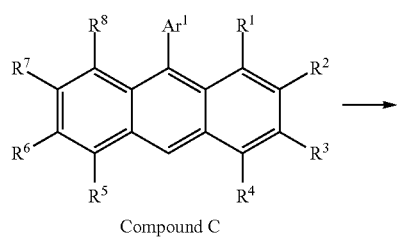

Compound C (A-12)

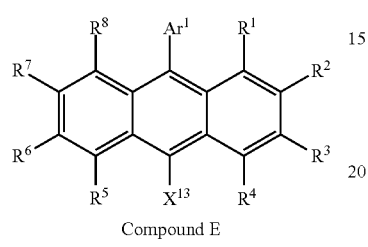

Compound E

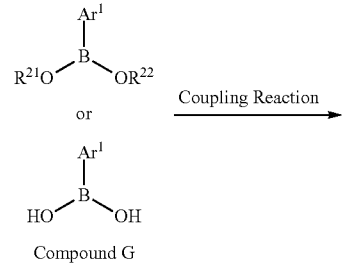

Compound G

Coupling Reaction

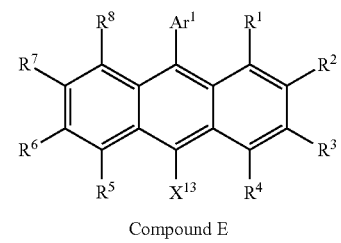

Compound E

Next, the synthesis scheme (A-3) is described in detail. When Suzuki-Miyaura coupling is performed in the reaction represented by the synthesis scheme (A-3), it is preferable that $X^4$ be halogen or triflate and $X^5$ be boronic acid or organoboron. Alternatively; it is preferable that $X^4$ be boronic acid or organoboron and $X^5$ be halogen or triflate. Further, a palladium catalyst is preferably used. When $X^4$ and $X^5$ are halogen, bromine or iodine is preferable.

That is, when the arylanthracene derivative (compound E) having an active site $X^3$ is 9-aryl-10-anthracene halide or 9-anthracene having a triflate group at a 10-position as a reaction active site, a 9,10-dihalogenated anthracene (compound F) and arylboronic acid (compound G) can be synthesized by performing coupling reaction at a mole ratio of 1:1 with the use of a palladium catalyst or the like as represented by a synthesis scheme (A-13a). At this time, the arylboronic acid (compound G) may be an arylorganoboron compound. Alternatively, as represented by a synthesis scheme (A-13b), anthracene-9,10-diboronic acid (compound F) and halogenated arene (compound G) are subjected to coupling reaction with a mole ratio of 1:1 with the use of a palladium catalyst or the like, so that 9-aryl-10-anthracene halide can be synthesized. At this time, the anthracene-9,10-diboronic acid (compound F) may be an anthracene-9,10-bisorganoboron compound.

(A-13a)

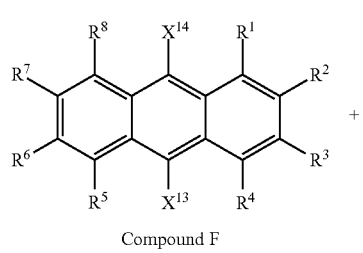

Compound F

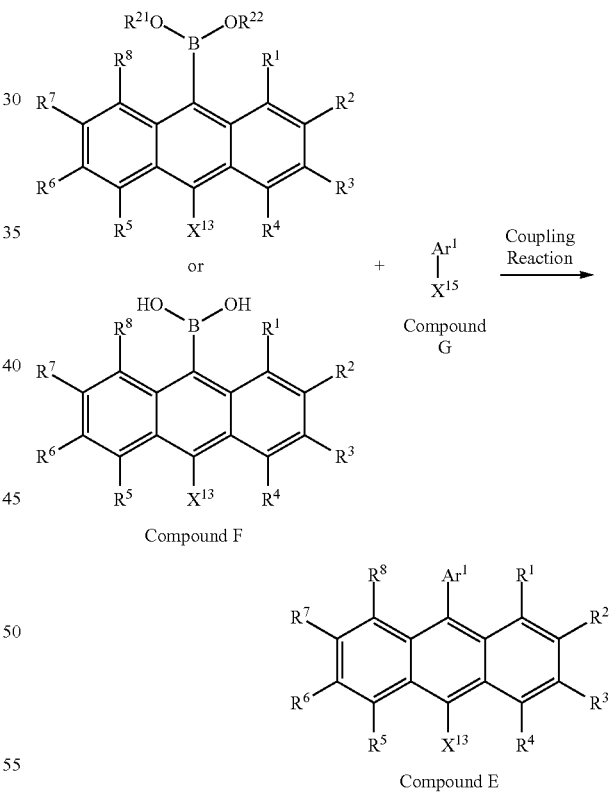

In the above schemes (A-13a) and (A-13b), each of $R^1$ to $R^8$ represents hydrogen, an alkyl group having 1 to 4 carbon atoms, or an aryl group having 6 to 15 carbon atoms; and $Ar^1$ represents an aryl group having 6 to 25 carbon atoms. $Ar^1$ may have a substituent. As the substituent, an alkyl group having 1 to 4 carbon atoms, an aryl group having 6 to 25 carbon atoms, halogen, a haloalkyl group, a cyano group, a nitro group, a carbonyl group, an ester group, an alkoxy group, or the like can be given. $X^{13}$, $X^{14}$, and $X^{15}$ represent halogen, and each of $R^{21}$ and $R^{22}$ represents an alkyl group having 1 to 6 carbon atoms. It is to be noted that $R^{21}$ and $R^{22}$ are combined to form a ring.

A target matter can be obtained with extremely high yield by coupling reaction of the anthracene derivative (compound F) in which carbon at a 9-position and carbon at a 10-position are activated and the arene (compound G) having reaction active carbon represented by the synthesis scheme (A-3); therefore, Suzuki-Miyaura coupling is preferably performed. In particular, in consideration of easiness for synthesis of materials, it is preferable that $X^6$ be halogen or triflate and $X^4$ be boronic acid or organoboron.

When $X^4$ is halogen, $X^5$ is a Grignard reagent, organotin, organic mercury, boronic acid, or organoboron. By performing coupling reaction using metal, a metal compound, or a metal catalyst such as a palladium catalyst or a nickel catalyst, the 9-arylanthracene derivative (compound E) can be synthesized. Alternatively, when $X^5$ is halogen, $X^4$ is a Grignard reagent, organotin, organic mercury, boronic acid, or organoboron. By performing coupling reaction using metal, a metal compound, or a metal catalyst such as a palladium catalyst or a nickel catalyst, the 9-arylanthracene derivative (compound E) can be synthesized.

When $X^4$ and $X^5$ are halogen or thiocyanate, the anthracene derivative (compound F) in which carbon at a 9-position and carbon at a 10-position are activated can be coupled with the arene (compound G) having reaction active carbon by Ullmann reaction in which copper or a copper compound is used. In the case where the Ullmann reaction is performed, although $X^4$ and $X^5$ may be same or different with each other, $X^4$ and $X^5$ are preferably iodine.

In accordance with the above synthesis method, the anthracene derivative represented by the general formula (1) can be synthesized. That is, a different substituent is introduced into a 9-position and into a 10-position of an anthracene skeleton from each other.

In a case where a compound in which a different substituent is introduced into the 9-position and into the 10-position of an anthracene skeleton is synthesized, skeletons are sequentially coupled one by one in general; therefore, the number of steps is increased, and it is not suitable for industry. That is, takt time of synthesis becomes longer, and the cost is increased due to lowering of the yield and the like. However, when the number of steps is omitted as much as possible (for example, a case of introducing two kinds of skeletons at one time to an anthracene skeleton at one stage), it is anticipated that variety of by-products are produced and purification is difficult; therefore, it is not suitable for industry. In particular, since purity of organic semiconductor materials is extremely important, there is a risk that characteristics of materials are drastically lowered when purification is difficult.

In the synthesis method of the present invention, skeletons that are to be introduced to an anthracene skeleton are separately synthesized, and the skeletons are introduced into a 9-position and into a 10-position of anthracene by 1 equivalent by the 2-3 steps. In the synthesis method of the present invention, reaction proceeds with high yield in each stage, and by-products are suppressed to be generated; therefore, this method can be considered to be the most suitable method in the consideration of the above problems. In addition, this method is suitable for mass-synthesis because the by-products can be suppressed, and it can be considered to be suitable method for industry.

Further, synthesis stages for obtaining an anthracene derivative that is a target matter can be omitted, and an anthracene derivative with higher purity can be synthesized more easily than the conventional method. Furthermore, time period for reaction can be shortened, which leads to reduction in cost.

Embodiment Mode 2

In this embodiment mode, an anthracene derivative of the present invention will be described.

An anthracene derivative of the present invention is an anthracene derivative represented by a general formula (1).

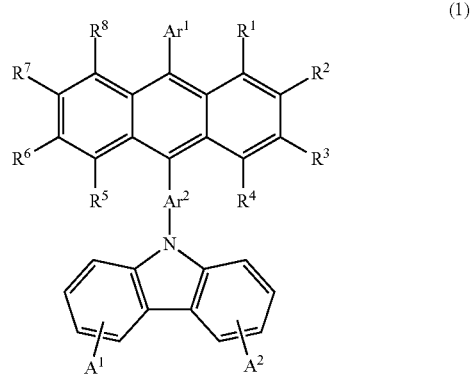

(1)

The anthracene derivative represented by the general formula (1) has an anthracene skeleton to which an aryl group is introduced as a substituent at 9- and 10-positions.

In general, since a blue light-emitting material with high color purity has low electrochemical stability and low stability in an excited state, a light-emitting element using the blue light-emitting material has difficulty in having long lifetime. Accordingly, electrochemical stability and stability in an excited state of a blue light-emitting material with high color purity is needed for improvement in reliability of the light-emitting element using the blue light-emitting material. Moreover, in the light-emitting element and in a light-emitting device and an electronic device that have the light-emitting element, stability to high temperature is particularly required in consideration of various external environments where the element and devices are used.

An anthracene derivative is known as a compound capable of emitting blue light; however, anthracene itself tends to form excimer in a solid state; accordingly, efficient light emission cannot be obtained even when anthracene itself is used for a light-emitting element. Further, chromaticity is reduced. Accordingly, introduction of bulky substituent is required to prevent the formation of excimer. In particular, it is an advantageous method to introduce a substituent into 9- and 10-positions that are most reactive of anthracene. Further, in order to keep the high carrier-transporting property of an anthracene skeleton, it is particularly effective to introduce an aryl group. The anthracene derivative represented by the general formula (1) can suppress formation of excimer because the anthracene derivative has an anthracene skeleton to which an aryl group is introduced as a substituent at 9- and 10-positions. Further, the carrier-transporting property can be kept.

On the other hand, a carbazolyl group has a structure in which phenyl groups of a diphenylamine group are bridged, so that a compound including a carbazolyl group has higher thermal stability than a compound including a diphenylamine group. Accordingly, by introducing a carbazolyl group, thermal stability (glass transition temperature or melting point) of a compound can be improved. Further, the present inventors have revealed that electrochemical stability is increased greater in the case of using a compound in which one carbazolyl group is introduced, for example, a compound in which a carbazolyl group is introduced into only one of phenyl groups in diphenylanthracene, than the case of using a compound in which two carbazolyl groups are introduced in both the phenyl groups in diphenylanthracene.

In other words, the inventors have revealed that the electrochemical stability is greatly improved by introducing a carbazolyl group into only an aryl group on one side. Therefore, it is a feature of the present invention that an anthracene derivative has an aryl group at one of 9- and 10-positions of anthracene as a substituent and an aryl group including a carbazolyl group at the other position. In addition, the carbazolyl group preferably has a structure in which a nitrogen atom at the 9-position is directly coupled with the aryl group.

An anthracene derivative of the present invention having the above structure has an extremely large band gap; therefore, light emission with a short wavelength is possible, and blue light emission with high color purity can be obtained.

It is to be noted that, in the anthracene derivative provided in the present invention, an aryl group or an alkyl group may be included in an anthracene skeleton or an aryl group that is directly coupled with the anthracene skeleton. This is based on the following reasons.

In a light-emitting element, crystallization of a material causes capital damage to an element. Specifically, it is an immediate cause of a short circuit between electrodes, which inhibits light emission. Therefore, the crystallinity of a material is required to be lowered. For this, it is effective to introduce an appropriate substituent into an anthracene skeleton or an aryl group that is directly coupled with the anthracene skeleton. An aryl group or an alkyl group can be used as such a substituent.

An aryl group or an alkyl group to be introduced is not limited; however, a phenyl group, an o-biphenyl group, or the like is preferable as the aryl group, and a methyl group, a t-butyl group, or the like is preferable as the alkyl group.

An alkyl group has an extremely great effect of suppressing crystallization, and it can suppress crystallization of a structure of which crystallization cannot be suppressed by introducing an aryl group. It is to be noted that introduction of an alkyl group may reduce a carrier transporting property; therefore, in the case where the crystallinity of the substance into which a substituent is to be introduced is not so high, an aryl group is more effective as the substituent to be introduced in terms of keeping the carrier transporting property.

Typical examples of the anthracene derivative of the present invention represented by the above general formula (1) are shown in the following structural formulas (11) to (53), structural formulas (61) to (76), and structural formulas (81) to (90). Naturally, the present invention is not limited thereto.

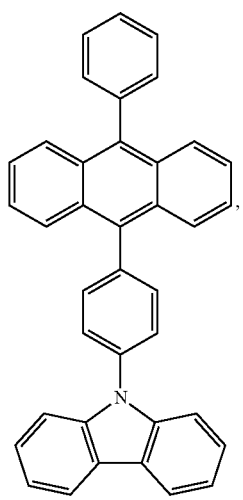

(11)

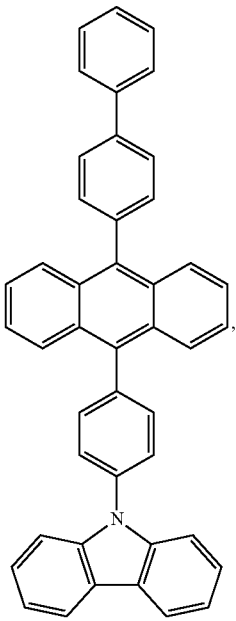

(12)

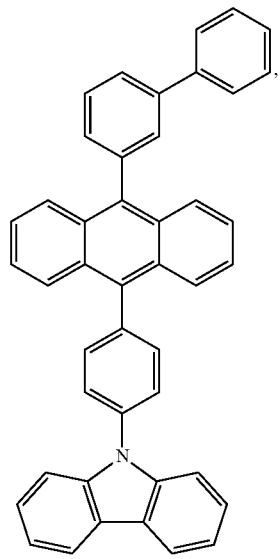

(13)

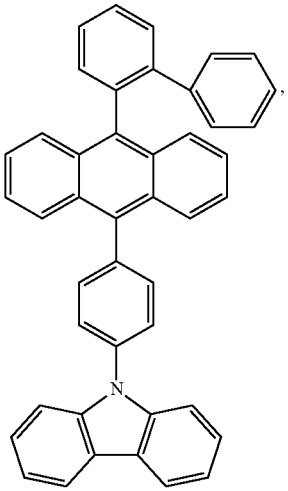

(14)

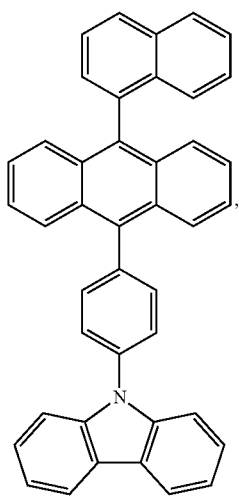
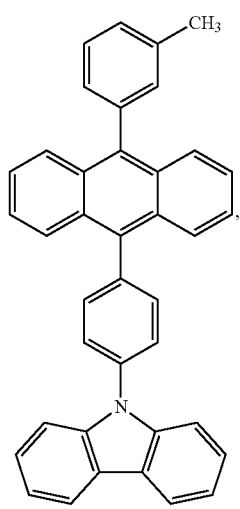
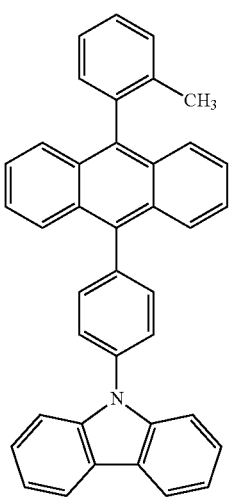
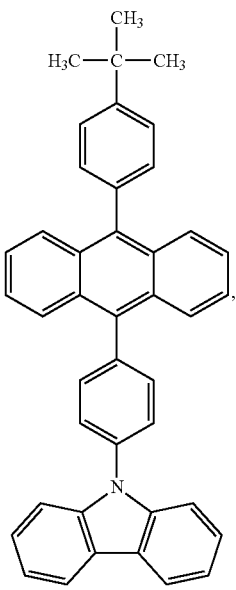

(21)
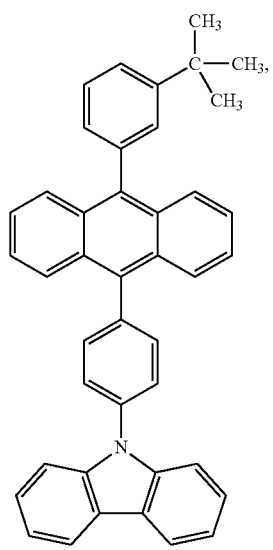
(22)
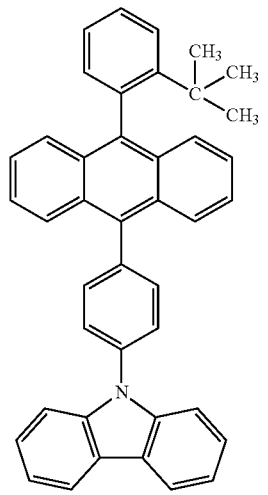
(23)
(24)
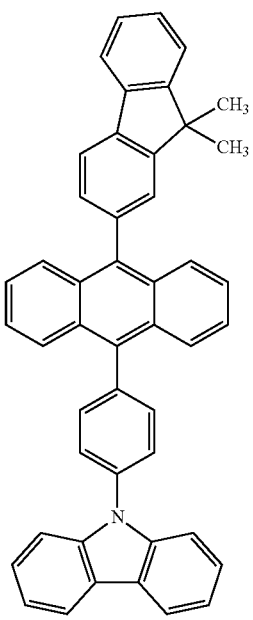
(25)
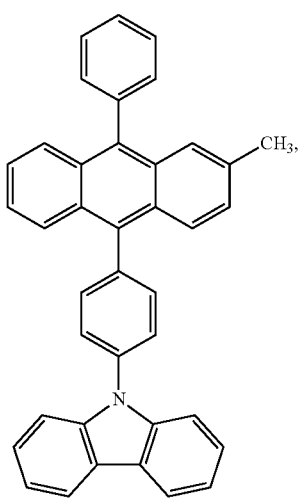
(26)
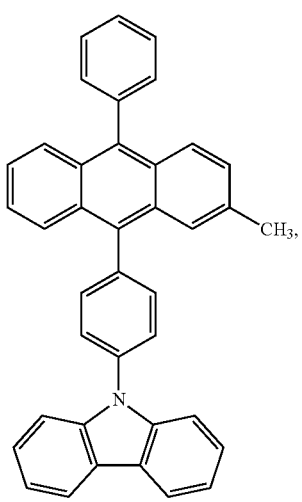

-continued
(27)
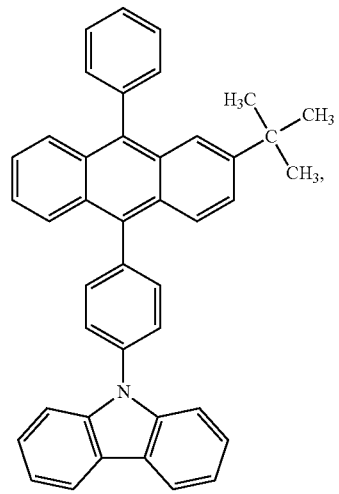
(28)
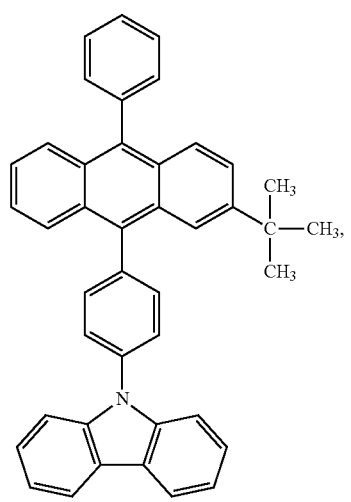
(29)
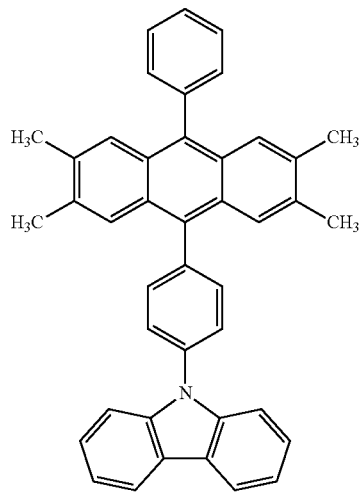
-continued
(30)
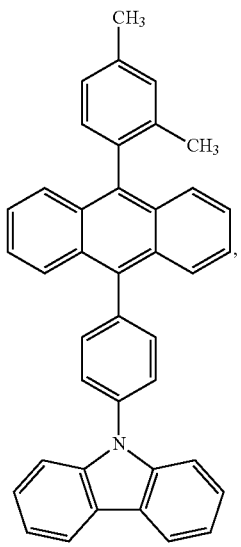
(31)
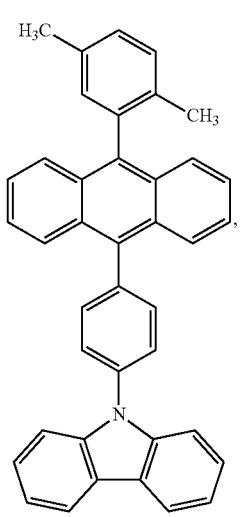
(32)
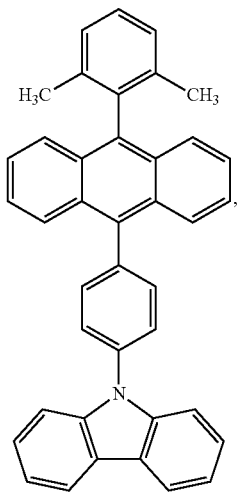

(33) 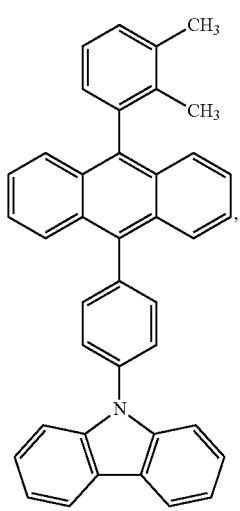
(34) 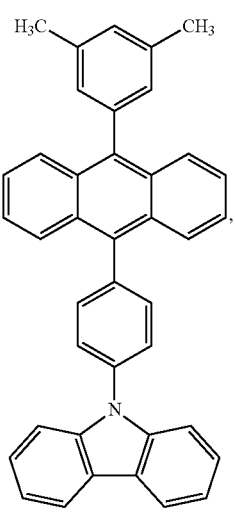
(35) 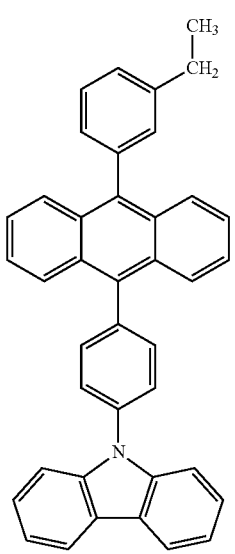
(36) 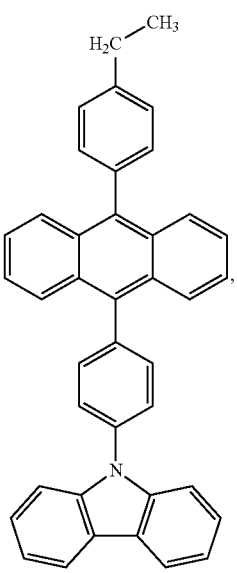
(37) 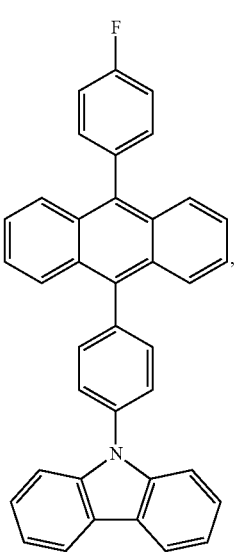
(38) 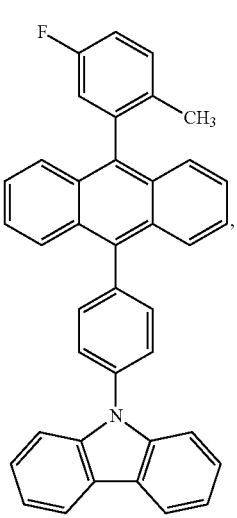

(39)
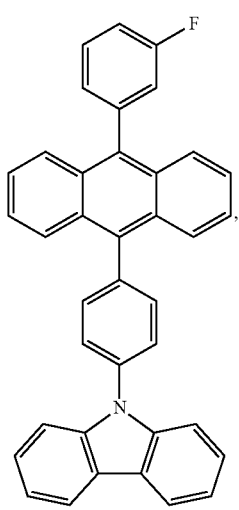
(40)
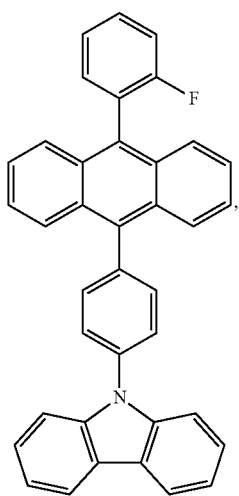
(41)
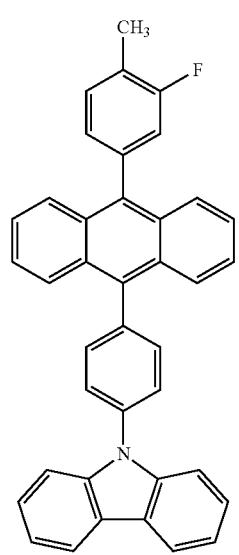
(42)
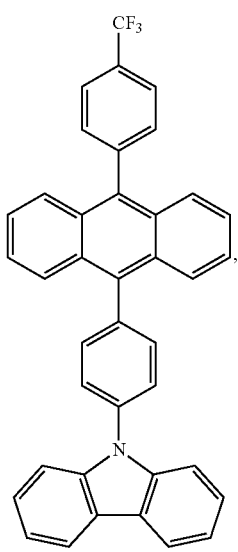
(43)
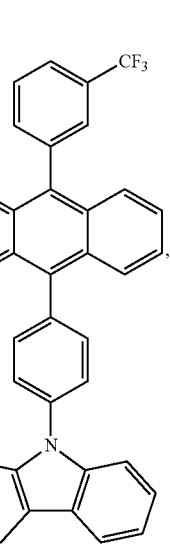
(44)
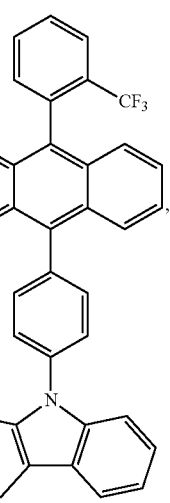

(45)
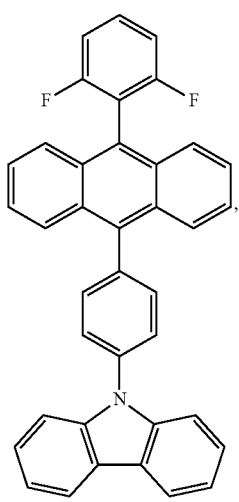
(46)
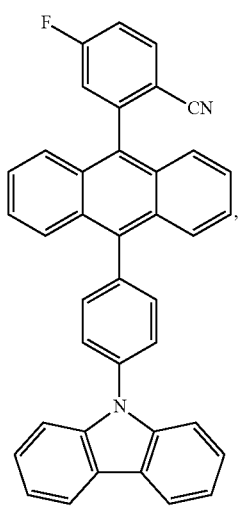
(47)
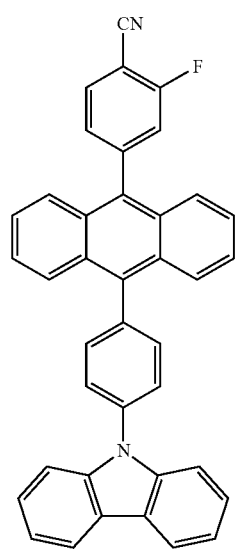
(48)
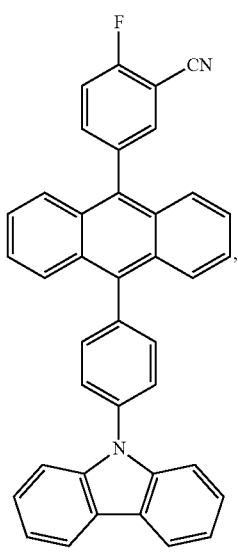
(49)
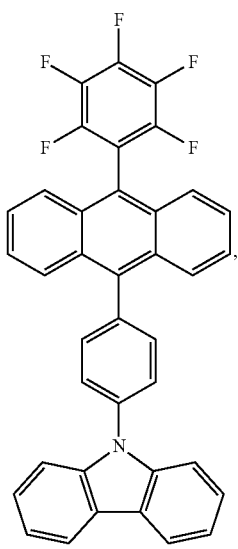
(50)
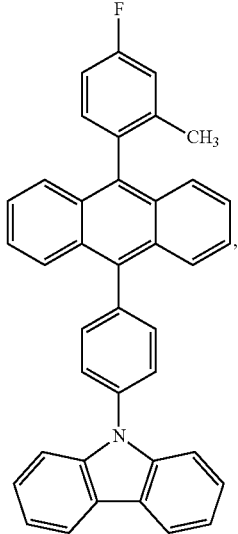

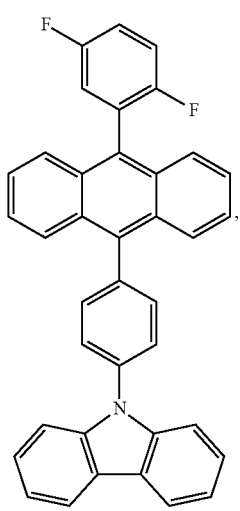
(51)
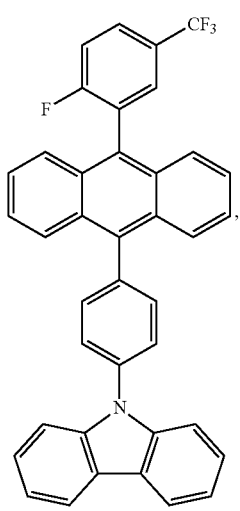
(52)
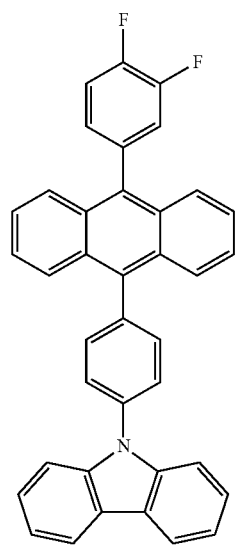
(53)
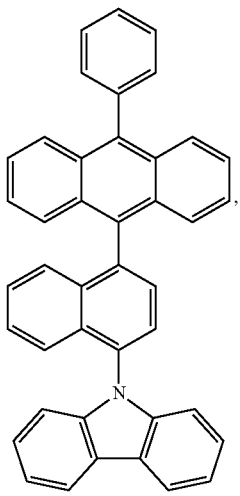
(61)
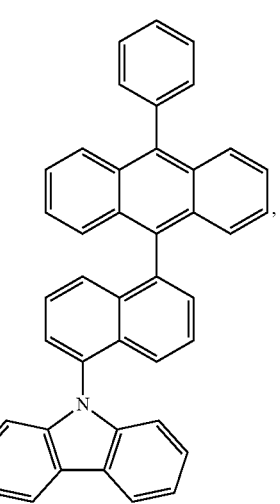
(62)
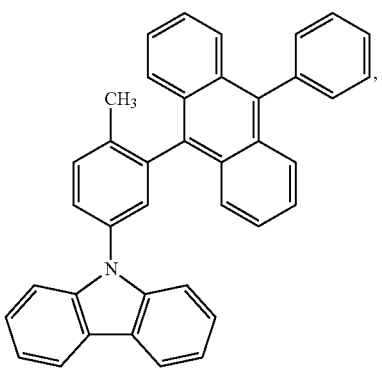
(63)

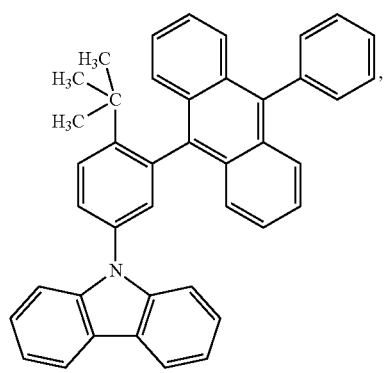
(64)
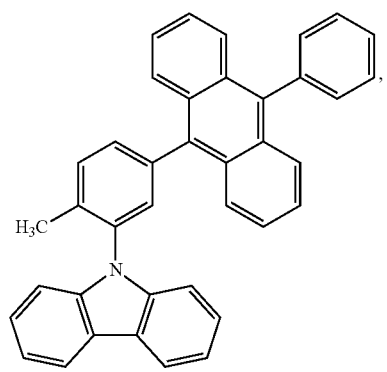
(65)
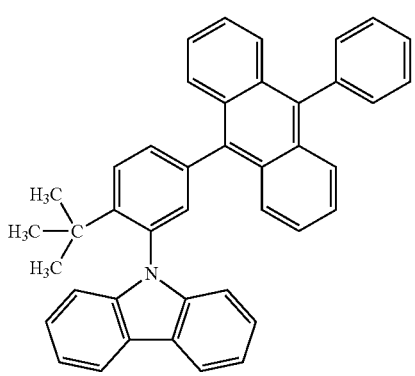
(66)
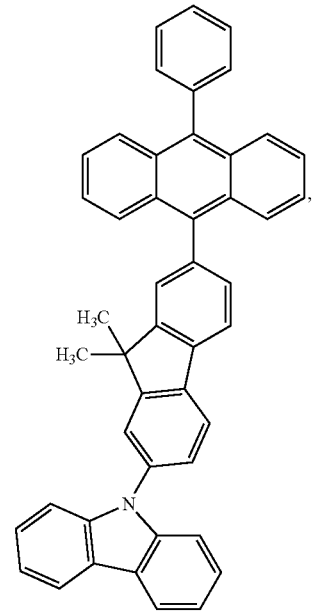
(67)
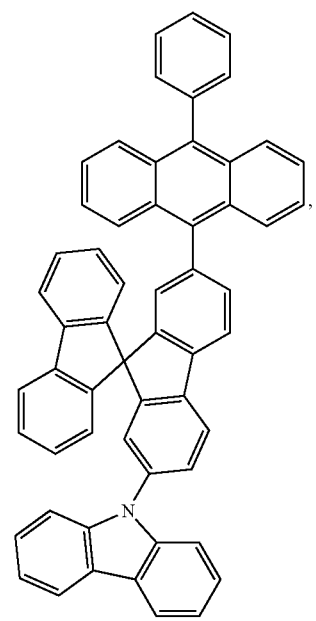
(68)
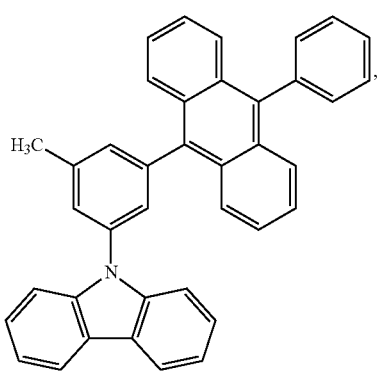
(69)

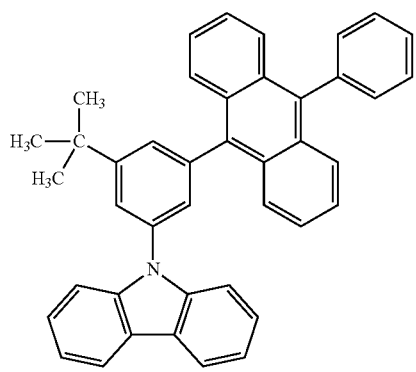
(70)
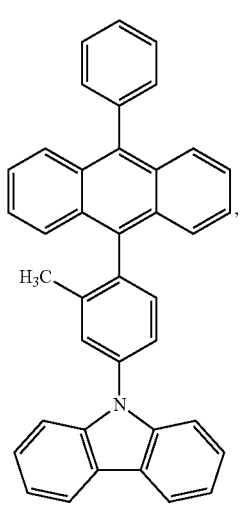
(71)
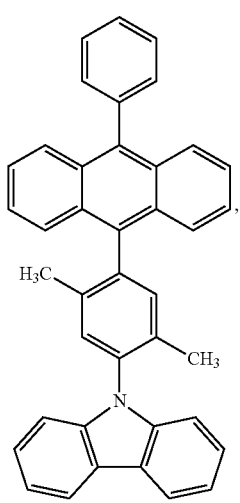
(72)
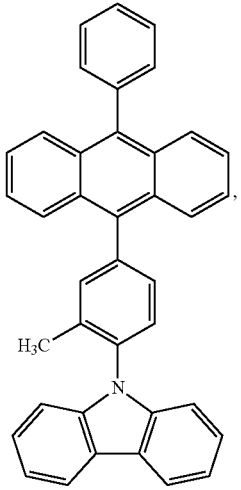
(73)
(74)
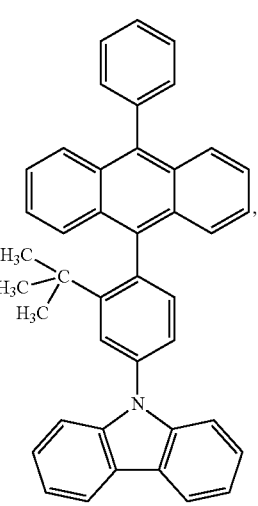
(75)

(76)
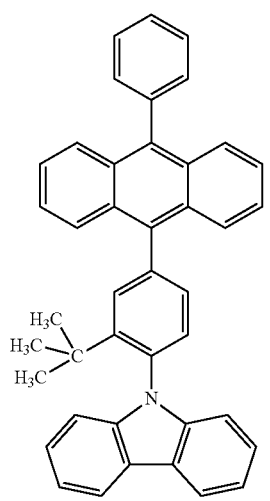
(83)
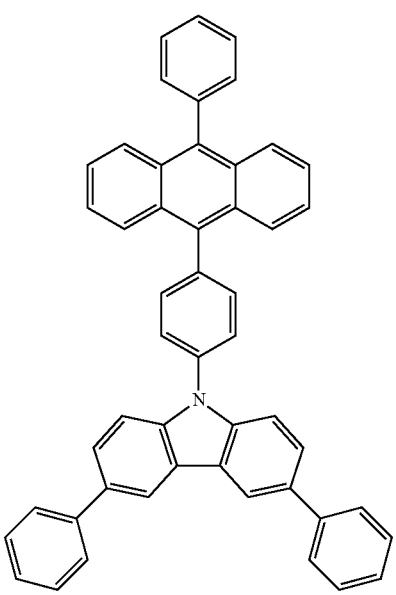
(81)
(82)
(84)
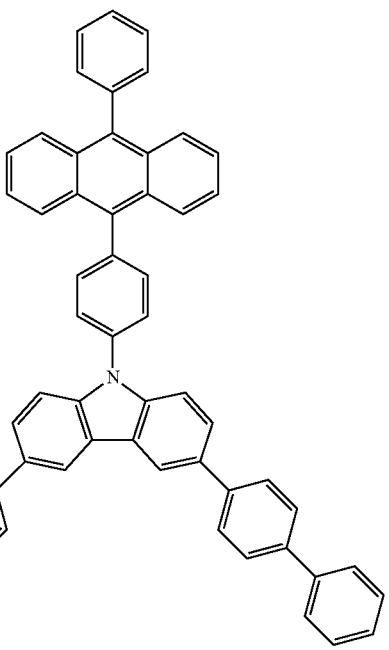

(85)
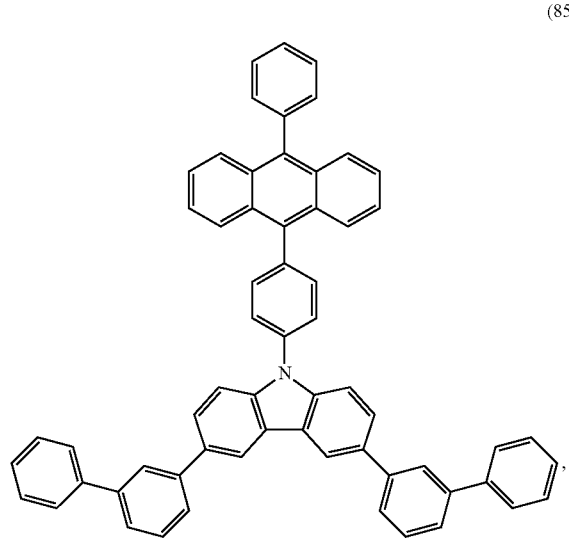
(86)
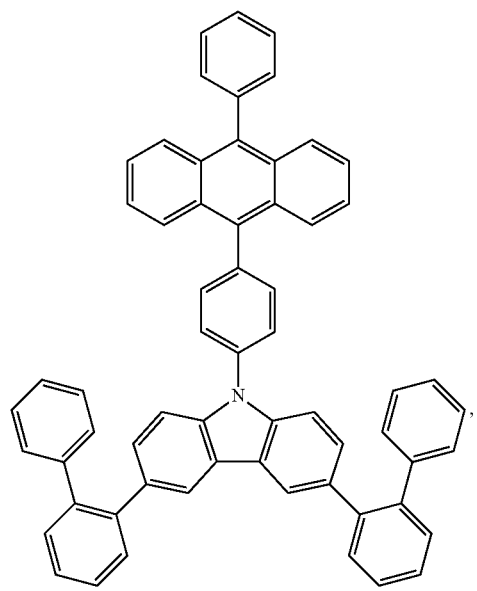
(87)
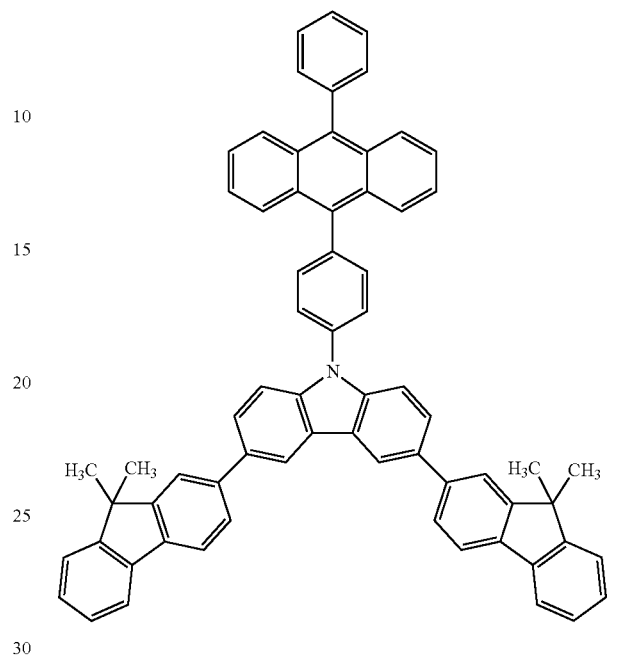
(88)
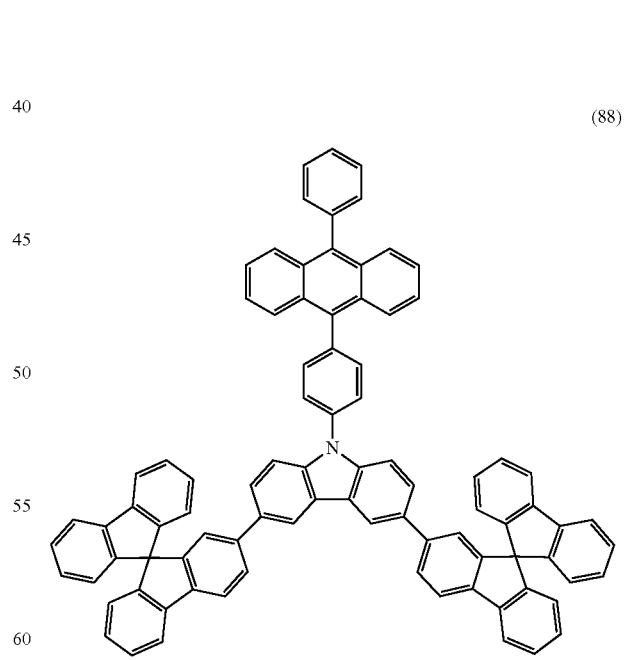

-continued (89)

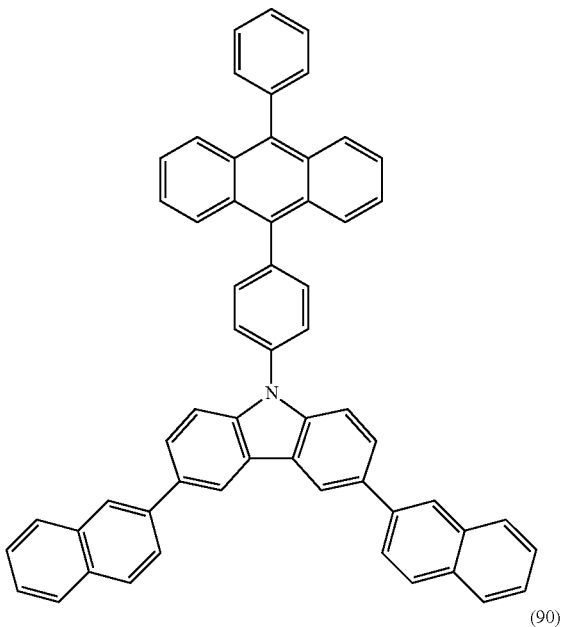

(90)

An anthracene derivative of the present invention has high electrochemical stability. Further, the anthracene derivative of the present invention has high thermal stability. Further, the anthracene derivative of the present invention has an extremely large band gap; accordingly, when it is used as a host in a light-emitting layer of a light-emitting element, blue light emission with high color purity can be obtained. Further, the anthracene derivative of the present invention has an extremely large band gap; accordingly, when it is used as a dopant in a light-emitting layer of a light-emitting element, blue light emission with high color purity can be obtained. A light-emitting element using an anthracene derivative of the present invention can be highly reliable. Especially, when an anthracene derivative of the present invention is used as both a host and a dopant in a light-emitting layer of a light-emitting element, the light-emitting element with extremely high reliability can be obtained.

The anthracene derivative represented by the above structural formulas (11) to (53), structural formulas (61) to (76), and structural formulas (81) to (90) can be synthesized using the synthesis method described in Embodiment Mode 1.

Embodiment Mode 3

In this embodiment mode, a mode of a light-emitting element using an anthracene derivative of the present invention will be described with reference to FIGS. 1A to 1C and FIG. 2.

A light-emitting element of the present invention has a plurality of layers between a pair of electrodes. The plurality of layers are stacked by combining layers formed from a substance with a high carrier injecting property or a substance with a high carrier transporting property, so that a light-emitting region is formed in a place separated from the electrodes, in other words, carriers are recombined in a portion separated from the electrodes. In the present specification, a plurality of layers formed between a pair of electrodes is hereinafter, referred to as an EL layer.

In this embodiment mode, a light-emitting element includes a first electrode 102, a first layer 103, a second layer 104, a third layer 105, a fourth layer 106, and a second electrode 107, which are sequentially stacked. It is to be noted that description will be made below in this embodiment mode under the condition that the first electrode 102 serves as an anode and the second electrode 107 serves as a cathode.

A substrate 101 is used as a supporting base of the light-emitting element. For the substrate 101, glass, plastic, or the like can be used, for example. It is to be noted that another material may be used as long as it serves as a supporting base in a manufacturing process of the light-emitting element.

As the first electrode 102, a metal, an alloy, an electrically conductive compound, a mixture thereof, or the like having a high work function (specifically, 4.0 eV or more) is preferably used. Specifically, indium oxide-tin oxide (ITO: Indium Tin Oxide), indium oxide-tin oxide containing silicon or silicon oxide, indium oxide-zinc oxide (IZO: Indium Zinc Oxide), indium oxide containing tungsten oxide and zinc oxide (IWZO), or the like can be given. Although these conductive metal oxide films are generally formed by sputtering, they may be formed by applying a sol-gel method or the like. For example, a film of indium oxide-zinc oxide (IZO) can be formed by a sputtering method using a target in which 1 to 20 wt % of zinc oxide is added to indium oxide. A film of indium oxide containing tungsten oxide and zinc oxide (IWZO) can be formed by a sputtering method using a target in which 0.5 to 5 wt % of tungsten oxide and 0.1 to 1 wt % of zinc oxide are contained in indium oxide. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride: TiN), or the like can be given.

The first layer 103 is a layer including a substance having a high hole injecting property. Molybdenum oxide (MoOx), vanadium oxide (VOx), ruthenium oxide (RuOx), tungsten oxide (WOx), manganese oxide (MnOx), or the like can be used. Alternatively, the first layer 103 can be formed using phthalocyanine (abbreviation: H$_2$Pc); a phthalocyanine-based compound such as copper phthalocyanine (abbreviation: CuPc); an aromatic amine compound such as 4,4'-bis[N-(4-diphenylaminophenyl)-N-phenylamino]biphenyl (abbreviation: DPAB) or 4,4'-bis(N-{4-[N-(3-methylphenyl)-N-phenylamino]phenyl}-N-phenylamino)biphenyl (abbreviation: DNTPD); or a high molecular material such as poly(ethylene dioxythiophene)/poly(styrenesulfonic acid) (PEDOT/PSS), or the like.

Alternatively, a composite material formed by combining an organic compound and an inorganic compound can be used for the first layer 103. In particular, a composite material including an organic compound and an inorganic compound having an electron accepting property with respect to the organic compound has an excellent hole injecting property and hole transporting property because the electrons are transferred between the organic compound and the inorganic compound, and the carrier density is increased.

In a case of using a composite material formed by combining an organic compound and an inorganic compound for the first layer 103, the first layer 103 can achieve an ohmic contact with the first electrode 102; therefore, a material of the first electrode can be selected regardless of work function.

As the inorganic compound used for the composite material, an oxide of a transition metal is preferably used. Moreover, oxides of metals belonging to Groups 4 to 8 in the periodic table can be given. Specifically, it is preferable to use vanadium oxide, niobium oxide, tantalum oxide, chromium oxide, molybdenum oxide, tungsten oxide, manganese oxide, and rhenium oxide, because of their high electron accepting properties. Among them, molybdenum oxide is particularly preferable because it is stable under air, has a low moisture absorption property, and is easily handled.

As the organic compound used for the composite material, various compounds such as an aromatic amine compound, a carbazole derivative, an aromatic hydrocarbon, and a high molecular compound (such as oligomer, dendrimer, or polymer) can be used. The organic compound used for the composite material is preferably an organic compound having a high hole transporting property. Specifically, a substance having a hole mobility of greater than or equal to $10^{-6}$ cm$^2$/Vs is preferably used. However, other materials than these materials may also be used as long as the hole transporting properties thereof are higher than the electron transporting properties thereof. The organic compounds that can be used for the composite material will be specifically shown below.

For example, the following can be given as the aromatic amine compound: N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N-(3-methylphenyl)-N-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); and the like.

As the carbazole derivatives that can be used for the composite material, the following can be provided specifically: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphtyl)-N-(9-phenylcarbazol-3-yl)amino]-9-phenylcarbazole (abbreviation: PCzPCN1); and the like.

Moreover, as the carbazole derivative that can be used for the composite material, the following can be given: 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; or the like.

As the aromatic hydrocarbon that can be used for the composite material, the following can be given for example: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides these compounds, pentacene, coronene, or the like can also be used. In particular, an aromatic hydrocarbon which has a hole mobility of greater than or equal to $1 \times 10^{-6}$ cm$^2$/Vs and which has 14 to 42 carbon atoms is more preferable.

The aromatic hydrocarbon that can be used for the composite material may have a vinyl skeleton. As the aromatic hydrocarbon having a vinyl group, the following are given for example: 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

Moreover, a high molecular compound such as poly(N-vinylcarbazole) (abbreviation: PVK) or poly(4-vinyltriphenylamine) (abbreviation: PVTPA) can also be used.

As a substance forming the second layer 104, a substance having a high hole transporting property, specifically, an aromatic amine compound (that is, a compound having a benzene ring-nitrogen bond) is preferable. As a material that is widely used, 4,4'-bis[N-(3-methylphenyl)-N-phenylamino] biphenyl, derivatives thereof such as 4,4'-bis[N-(1-naphthyl)-N-phenylamino]biphenyl (hereinafter referred to as NPB), and star burst aromatic amine compounds such as 4,4',4"-tris (N,N-diphenyl-amino)triphenylamine and 4,4',4"-tris[N-(3-methylphenyl)-N-phenylamino]triphenylamine can be given. These materials described here are mainly substances each having a hole mobility of greater than or equal to $10^{-6}$ cm$^2$/Vs. However, other materials than these compounds may also be used as long as the hole transporting properties thereof are higher than the electron transporting properties thereof. The second layer 104 is not limited to a single layer, and a mixed layer of the aforementioned substances, or a stacked layer which comprises two or more layers each including the aforementioned substance may be used.

The third layer 105 is a layer including a light-emitting substance. In this embodiment mode, the third layer 105 includes the anthracene derivative of the present invention described in Embodiment Mode 1. The anthracene derivative of the present invention can favorably be applied to a light-emitting element as a light-emitting substance because the anthracene derivative of the present invention is capable of emitting light with a short wavelength and exhibits blue light emission with high color purity.

As the fourth layer 106, a substance having a high electron transporting property can be used. For example, a layer including a metal complex or the like having a quinoline or benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq) can be used. Alternatively, a metal complex or the like having an oxazole-based or thiazole-based ligand, such as bis[2-(2-hydroxyphenyl)benzoxazolato]zinc (abbreviation: $Zn(BOX)_2$) or bis[2-(2-hydroxyphenyl)-benzothiazolato]zinc (abbreviation: $Zn(BTZ)_2$) can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here are mainly substances each having an electron mobility of greater than or equal to $10^{-6}$ cm$^2$/Vs. The electron transporting layer may be formed using other materials than those described above as long as the materials have higher electron transporting properties than hole transporting properties. Furthermore, the electron transporting layer is not limited to a single layer, and two or more layers in which each layer is made of the aforementioned substance may be stacked.

As a substance forming the second electrode 107, a metal, an alloy, an electrically conductive compound, a mixture thereof, or the like having a low work function (specifically, 3.8 eV or less) is preferably used. As a specific example of such a cathode material, an element belonging to Group 1 or Group 2 in the periodic table, that is, an alkali metal such as lithium (Li) or cesium (Cs), an alkaline earth metal such as magnesium (Mg), calcium (Ca), or strontium (Sr), an alloy including these metals (MgAg, AlLi) can be employed. A rare earth metal such as europium (Eu) or ytterbium (Yb), an alloy including these rare earth metals, or the like is also suitable. However, by providing a layer having a function of promoting electron injection between the second electrode 107 and the fourth layer 106 so that it is stacked with the second electrode, various conductive materials such as Al, Ag, ITO, or ITO containing silicon or silicon oxide can be used for the second electrode 107 regardless of the magnitude of the work function.

As the layer having a function of promoting electron injection, an alkali metal, an alkaline earth metal, or a compound thereof such as lithium fluoride (LiF), cesium fluoride (CsF), or calcium fluoride ($CaF_2$) can be used. For example, a layer which contains substance having an electron transporting property and an alkali metal, an alkaline earth metal, or a compound thereof (Alq including magnesium (Mg) for example) can be used. It is preferable to use such a layer because electron injection from the second electrode 107 proceeds efficiently.

Various methods can be used for forming the first layer 103, the second layer 104, the third layer 105, and the fourth layer 106. For example, an evaporation method, an ink-jet method, a spin coating method, or the like may be used. Furthermore, each electrode or each layer may be formed by a different film formation method.

By making current flow due to a potential difference generated between the first electrode 102 and the second electrode 107, holes and electrons are recombined in the third layer 105 including a substance with a high light-emitting property, which results in a light-emission from the light-emitting element of the present invention. That is, the light-emitting element of the present invention has a structure in which a light-emitting region is formed in the third layer 105.

Figure 1B:
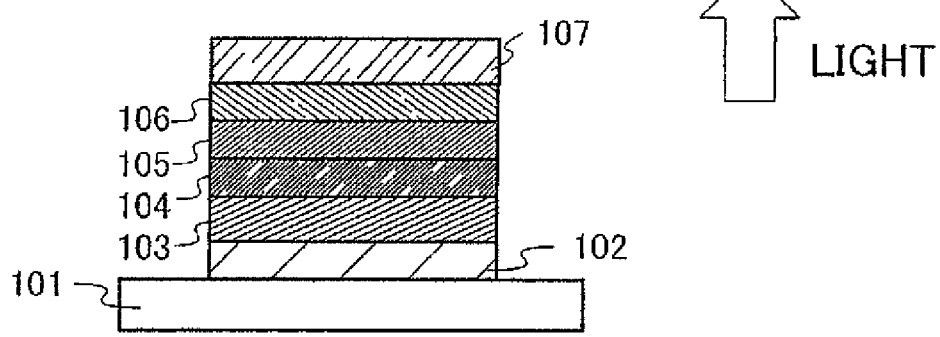
Figure 1C:
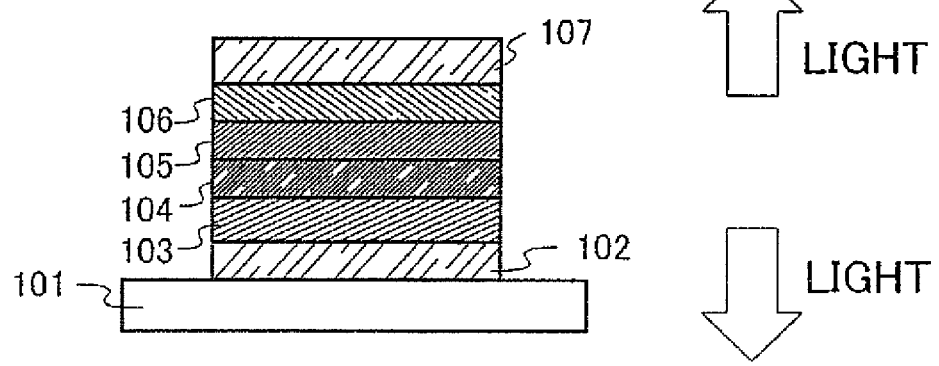

Light emission is extracted outside through one or both of the first electrode 102 and the second electrode 107. Therefore, one or both of the first electrode 102 and the second electrode 107 is/are formed using an electrode having a light transmitting property. In a case where only the first electrode 102 is an electrode having a light transmitting property, light emission is extracted from a substrate side through the first electrode 102 as shown in FIG. 1A. Alternatively, in a case where only the second electrode 107 is an electrode having a light transmitting property, light emission is extracted from the side opposite to the substrate through the second electrode 107 as shown in FIG. 1B. In a case where both of the first electrode 102 and the second electrode 107 are the electrodes having a light transmitting property, light emission is extracted from both of the substrate side and the side opposite to the substrate through the first electrode 102 and the second electrode 107, as shown in FIG. 1C.

A structure of layers provided between the first electrode 102 and the second electrode 107 is not limited to the above-described structure. A structure other than the above-described structure may be used as long as the light-emitting region, in which holes and electrons are recombined, is located away from the first electrode 102 and the second electrode 107, so as to prevent the quenching due to proximity of the light-emitting region and the metal.

In other words, a stacked structure of the layer is not particularly limited to the abovementioned structure, and a layer formed using a substance having a high electron transporting property, a substance having a high hole transporting property, a substance having a high electron injecting property, a substance having a high hole injecting property, a bipolar substance (substance having a high electron transporting property and a high hole transporting property), a hole blocking material, or the like may be freely combined with the anthracene derivative of the present invention.

Figure 2:
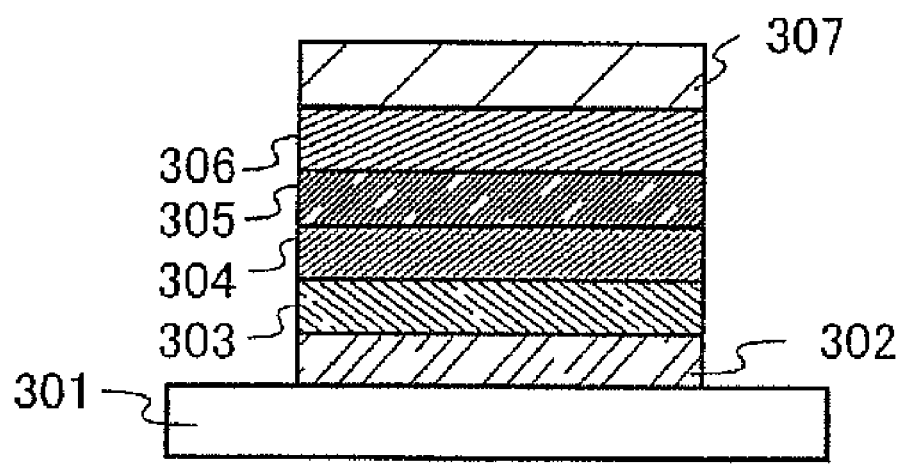
FIG. 2 is a view explaining a light-emitting element of the present invention.

A light-emitting element shown in FIG. 2 has a structure in which a first electrode 302 serving as a cathode, a first layer 303 formed using a substance having a high electron transporting property, a second layer 304 including a light-emitting substance, a third layer 305 formed using a substance having a high hole transporting property, a fourth layer 306 formed using a substance having a high hole injecting property, and a second electrode 307 serving as an anode are sequentially stacked over a substrate 301.

In this embodiment mode, a light-emitting element is manufactured over a substrate made of glass, plastic, or the like. By manufacturing a plurality of the light-emitting elements described above over one substrate, a passive-matrix light-emitting device can be manufactured. Alternatively, for example, a thin film transistor (TFT) may be formed over a substrate made of glass, plastic, or the like, and the light-emitting elements may be manufactured over an electrode electrically connected to the TFT. Accordingly, an active matrix light-emitting device can be manufactured, in which driving of the light-emitting element is controlled by the TFT. The structure of the TFT is not strictly limited, and the TFT may be a staggered TFT or an inverted staggered TFT. Crystallinity of a semiconductor used for the TFT is also not limited, and an amorphous semiconductor or a crystalline semiconductor may be used. In addition, a driving circuit formed over a TFT substrate may be formed using an N-type TFT and a P-type TFT, or may be formed using any one of an N-type TFT and a P-type TFT.

As shown in this embodiment mode, an anthracene derivative of the present invention can be used for a light-emitting layer as shown in this embodiment mode without adding any other light-emitting substance, because the anthracene derivative emits blue light with high purity.

Since the anthracene derivative of the present invention has high luminous efficiency, a light-emitting element with high luminous efficiency can be obtained by using the anthracene derivative of the present invention in a light-emitting element. Also, by using the anthracene derivative of the present invention in a light-emitting element, a light-emitting element with high reliability can be obtained.

Since the light-emitting element using the anthracene derivative of the present invention is capable of emitting blue light with high color purity, it can be favorably used for a full-color display. Further, the ability of the light-emitting element using the anthracene derivative of the present invention to achieve emit blue light with high reliability allows its application in a full-color display.

Embodiment Mode 4

In this embodiment mode, a light-emitting element having a different structure from that shown in Embodiment Mode 3 will be described.

The third layer 105 shown in Embodiment Mode 3 is formed to have a structure in which an anthracene derivative of the present invention is dispersed into another substance, whereby light emission can be obtained from the anthracene derivative of the present invention. Since the anthracene derivative of the present invention exhibits blue light emission with high color purity, a light-emitting element exhibiting blue light emission with high color purity can be obtained.

Here, as a substance for dispersing an anthracene derivative of the present invention, a substance with a larger band gap than the anthracene derivative of the present invention is preferably used. Specifically, a low molecular compound such as 4,4',4"-tri(N-carbazolyl)triphenylamine (abbreviation: TCTA), 1,1-bis[4-(diphenylamino)phenyl]cyclohexane (abbreviation: TPAC), 9,9-bis[4-(diphenylamino)phenyl]fluorene (abbreviation: TPAF), 4,4'-di(N-carbazolyl)biphenyl (abbreviation: CBP), 1,3-bis[5-(p-tert-butylphenyl)-1,3,4-oxadiazol-2-yl]benzene (abbreviation: OXD-7), 2,2',2"-(1,3,5-benzenetriyl)tris(1-phenyl-1H-benzimidazole) (abbreviation: TPBI), 3-(4-tert-butylphenyl)-4-phenyl-5-(4-biphenylyl)-1,2,4-triazole (abbreviation: TAZ), or 9,9',9"-[1,3,5-triazine-2,4,6-triyl]tricarbazole (abbreviation: TCzTRZ), or a high molecular compound such as poly(N-vinylcarbazole) (abbreviation: PVK), poly(4-vinyltriphenylamine) (abbreviation: PVTPA), or poly(2,5-pyridine-diyl) (abbreviation: PPy) can be used.

Since the anthracene derivative of the present invention is capable of emitting blue light with high color purity, by using the anthracene derivative for a light-emitting element, a light-emitting element exhibiting blue light emission with high color purity can be obtained.

Since the anthracene derivative of the present invention has high luminous efficiency, a light-emitting element with high luminous efficiency can be obtained by using the anthracene derivative of the present invention in a light-emitting element. Also, by using the anthracene derivative of the present invention in a light-emitting element, a light-emitting element with high reliability can be obtained.

Since the light-emitting element using the anthracene derivative of the present invention is capable of emitting blue light with high color purity, it can be favorably used for a full-color display. Further, the ability of the light-emitting element using the anthracene derivative of the present invention to achieve emit blue light with high reliability allows its application in a full-color display.

It is to be noted that the structure shown in Embodiment Mode 2 except for the third layer 105 can be used as appropriate.

Embodiment Mode 5

In this embodiment mode, a light-emitting element having a different structure from those shown in Embodiment Modes 3 and 4 will be described.

The third layer 105 shown in Embodiment Mode 3 is formed to have a structure in which a light-emitting substance is dispersed into the anthracene derivative of the present invention, whereby light emission from the light-emitting substance can be obtained.

In a case where the anthracene derivative of the present invention is used as a material for dispersing another light-emitting substance, a light emission color derived from the light-emitting substance can be obtained. Further, a mixed light emission color resulted from the anthracene derivative of the present invention and the light-emitting substance dispersed in the anthracene derivative can also be obtained.

Here, a substance having a smaller band gap than the anthracene derivative of the present invention is preferably used as a light-emitting substance that is dispersed in the anthracene derivative of the present invention. Specifically, the following substances can be given, such as N,N'-bis[4-(9H-carbazol-9-yl)phenyl]-N,N'-diphenylstilbene-4,4'-diamine (abbreviation: YGA2S), 2,5,8,11-tetra(tert-butyl)perylene (abbreviation: TBP), perylene, coumarin 30, coumarin 6, coumarin 545T, N,N'-dimethylquinacridone (abbreviation: DMQd), N,N'-diphenylquinacridone (abbreviation: DPQd), N,N,9-triphenylanthracen-9-amine (abbreviation: DPhAPhA), 5,12-bis(1,1'-biphenyl-4-yl)-6,11-diphenyltetracene (abbreviation: BPT), rubrene, N,N,N',N'-tetrakis(4-methylphenyl)tetracene-5,11-diamine (abbreviation: p-mPhTD), or 7,13-diphenyl-N,N,N',N'-tetrakis(4-methylphenyl)acenaphtho[1,2-a]fluoranthene-3,10-diamine (abbreviation: p-mPhAFD).

Since the anthracene derivative of the present invention has a large band gap, a light-emitting substance dispersed into the anthracene derivative of the present invention is selected from a wide selection range. For example, a light-emitting substance exhibiting blue light emission with high color purity can be dispersed. Specifically, a light-emitting substance having a band gap of greater than or equal to 2.7 eV and less than or equal to 3.0 eV or a light-emitting substance having a maximum emission wavelength between 400 to 500 nm is dispersed into the anthracene derivative of the present invention because such a light-emitting substance exhibits blue light emission with high color purity, whereby a light-emitting element exhibiting blue light emission with high color purity can be obtained.

It is to be noted that the structure shown in Embodiment Mode 3 except for the third layer 105 can be used as appropriate.

Embodiment Mode 6

In this embodiment mode, a light-emitting element having a different structure from those shown in Embodiment Modes 3 to 5 will be described.

By combining the anthracene derivative of the present invention and an inorganic compound having an electron accepting property with respect to the anthracene derivative of the present invention, a layer including the anthracene derivative of the present invention can be used between an anode and a light-emitting layer. Specifically, the layer including the anthracene derivative can be used for the first layer 103 or the second layer 104 shown in Embodiment Mode 3. By using such a composite material, carrier density is increased, which contributes to improvement of the hole injecting property and hole transporting property. Also, in a case of using the composite material in the first layer 103, the first layer 103 can achieve an ohmic contact with the first electrode 102; therefore, a material of the first electrode can be selected regardless of work function.

As the inorganic compound used for the composite material, an oxide of a transition metal is preferably used. Moreover, oxides of metals belonging to Groups 4 to 8 in the periodic table can be given. Specifically, it is preferable to use vanadium oxide, niobium oxide, tantalum oxide, chromium oxide, molybdenum oxide, tungsten oxide, manganese oxide, and rhenium oxide, because of their high electron accepting properties. Among them, molybdenum oxide is particularly preferable because it is stable under air, has a low moisture absorption property, and is easily handled.

It is to be noted that this embodiment mode can be combined with any other embodiment modes as appropriate.

Embodiment Mode 7

In this embodiment mode, a light-emitting element in which a plurality of light-emitting units according to the present invention are stacked (hereinafter, referred to as a stacked type element) will be described with reference to FIG. 3. This light-emitting element is a stacked type light-emitting element that has a plurality of light-emitting units between a first electrode and a second electrode. A structure similar to those described in Embodiment Modes 3 to 6 can be used for each light-emitting unit. In other words, the light-emitting element described in Embodiment Mode 3 is a light-emitting element having one light-emitting unit. In this embodiment mode, a light-emitting element having a plurality of light-emitting units will be described.

Figure 3:
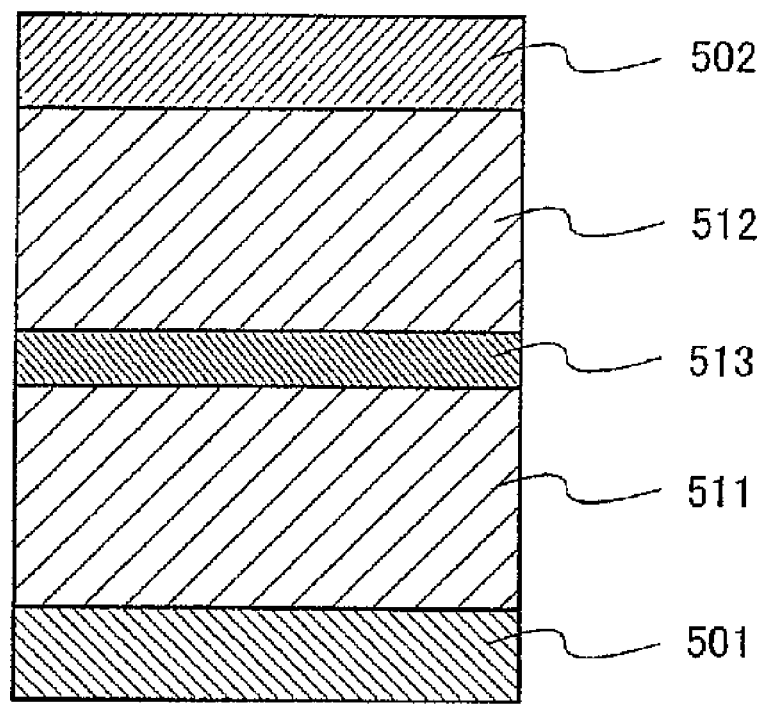
FIG. 3 is a view explaining a light-emitting element of the present invention.

In FIG. 3, a first light-emitting unit 511 and a second light-emitting unit 512 are stacked between a first electrode 501 and a second electrode 502. An electrode similar to that described in Embodiment Mode 2 can be applied to the first electrode 501 and the second electrode 502. The first light-emitting unit 511 and the second light-emitting unit 512 may have the same structure or different structures, and a structure similar to those described in Embodiment Modes 3 to 6 can be applied.

A charge generation layer 513 includes a composite material of an organic compound and metal oxide. The composite material of an organic compound and metal oxide is described in Embodiment Mode 2 or 5, and includes an organic compound and metal oxide such as vanadium oxide, molybdenum oxide, or tungsten oxide. As the organic compound, various compounds such as an aromatic amine compound, a carbazole derivative, an aromatic hydrocarbon, and a high molecular compound (such as oligomer, dendrimer, or polymer) can be used. An organic compound having a hole mobility of greater than or equal to $1\times10^{-6}$ cm$^2$/Vs is preferably applied as the organic compound having a hole transporting property. However, other substances than these compounds may also be used as long as the hole transporting properties thereof are higher than the electron transporting properties thereof. The composite material of an organic compound and metal oxide is superior in a carrier injecting property and a carrier transporting property, and accordingly, low-voltage driving and low-current driving can be realized.

It is to be noted that the charge generation layer 513 may be formed with a combination of a composite material of an organic compound and metal oxide and other materials. For example, the charge generation layer 513 may be formed with a combination of a layer including the composite material of an organic compound and metal oxide and a layer including one compound selected from electron donating substances and a compound having a high electron transporting property. Further, the charge generation layer 513 may be formed with a combination of a layer including the composite material of an organic compound and metal oxide and a transparent conductive film.

In any case, the charge generation layer 513 interposed between the first light-emitting unit 511 and the second light-emitting unit 512 is acceptable as long as electrons are injected to one light-emitting unit and holes are injected to the other light-emitting unit when a voltage is applied between the first electrode 501 and the second electrode 502. For example, in a case of applying a voltage so that a potential of the first electrode is higher than potential of the second electrode, any structure is acceptable for the charge generation layer 513 as long as the layer 513 injects electrons and holes into the first light-emitting unit 511 and the second light-emitting unit 512, respectively.

In this embodiment mode, the light-emitting element having two light-emitting units is described; however, the present invention can be applied to a light-emitting element in which three or more light-emitting units are stacked. By arranging a plurality of light-emitting units between a pair of electrodes in such a manner that the plurality of light-emitting units are partitioned with a charge generation layer as the light-emitting element of this embodiment mode, an element having a long lifetime in a high luminance region can be realized with keeping a low current density. In a case of applying the light-emitting element to a lightning system, voltage drop due to resistance of an electrode material can be decreased; therefore, uniform light emission in a large area is possible. Further, low voltage driving is possible, and a light-emitting device with low power consumption can be realized.

This embodiment mode can be combined with any other embodiment modes as appropriate.

Embodiment Mode 8

In this embodiment mode, a light-emitting device manufactured using an anthracene derivative of the present invention will be described.

Figure 4A:
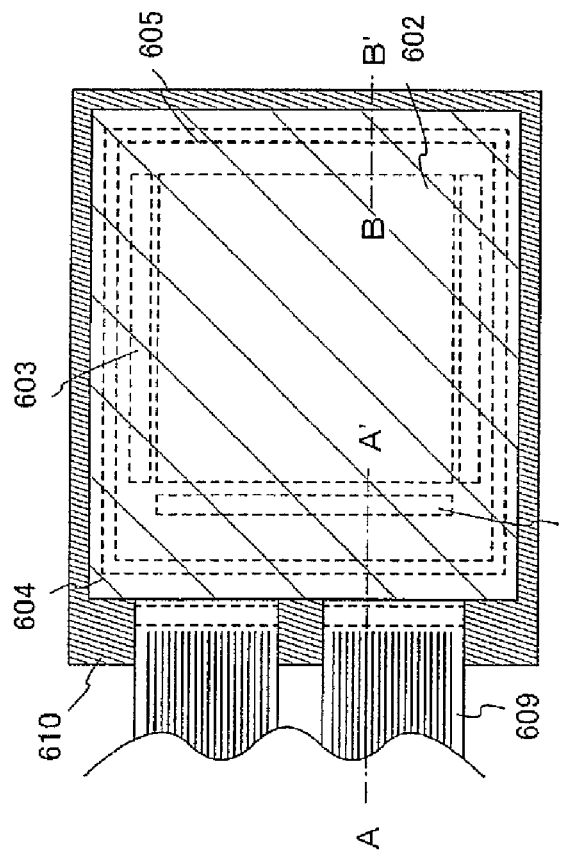
FIGS. 4A and 4B are views explaining a light-emitting device of the present invention.
Figure 4B:
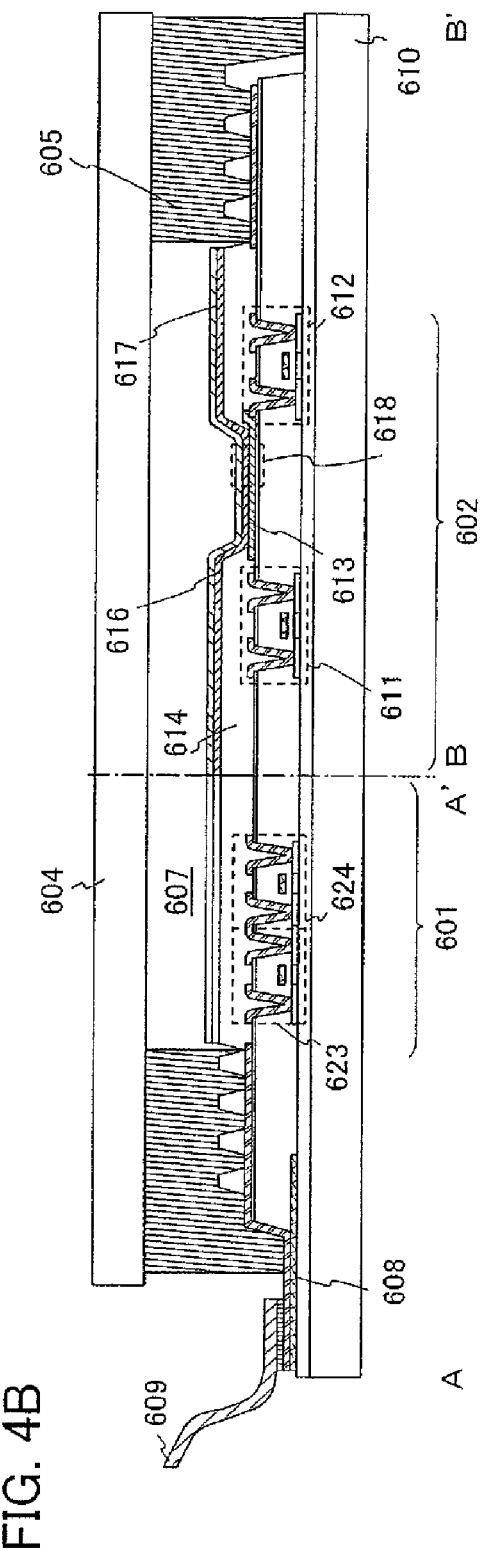

In this embodiment mode, a light-emitting device manufactured using the anthracene derivative of the present invention will be described with reference to FIGS. 4A and 4B. FIG. 4A is a top view showing a light-emitting device, and FIG. 4B is a cross-sectional view of FIG. 4A taken along lines A-A' and B-B'. A driver circuit portion (source driver circuit), a pixel portion, and a driver circuit portion (gate driver circuit) are denoted by reference numerals 601, 602, and 603, respectively, and are indicated by dotted lines. Also, a sealing substrate and a sealing material are denoted by reference numerals 604 and 605, respectively, and a portion surrounded by the sealing material 605 corresponds to a space 607.

A leading wiring 608 is a wiring for transmitting a signal to be inputted to the source driver circuit 601 and the gate driver circuit 603, and this wiring 608 receives a video signal, a clock signal, a start signal, a reset signal, and the like from an FPC (flexible printed circuit) 609 that is an external input terminal. It is to be noted that only the FPC is shown here; however, the FPC may be provided with a printed wiring board (PWB). The light-emitting device in the present specification includes not only a light-emitting device itself but also a light-emitting device attached with an FPC or a PWB.

Subsequently, a cross-sectional structure will be described with reference to FIG. 4B. The driver circuit portion and the pixel portion are formed over an element substrate 610. Here, the source driver circuit 601, which is the driver circuit portion, and one pixel in the pixel portion 602 are shown.

A CMOS circuit, which is a combination of an n-channel TFT 623 and a p-channel TFT 624, is formed as the source driver circuit 601. The driver circuit may be formed using various CMOS circuits, PMOS circuits, or NMOS circuits. Although a driver-integration type device, in which a driver circuit is formed over a substrate, is described in this embodiment mode, a driver circuit is not necessarily formed over a substrate and can be formed outside a substrate.

The pixel portion 602 has a plurality of pixels, each of which includes a switching TFT 611, a current control TFT 612, and a first electrode 613 that is electrically connected to a drain of the current control TFT 612. It is to be noted that an insulator 614 is formed so as to cover an end portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in a case of using a positive photosensitive acrylic resin as a material for the insulator 614, the insulator 614 is preferably formed so as to have a curved surface with a curvature radius (0.2 μm to 3 μm) only at the upper end portion thereof. Either a negative type resin which becomes insoluble in an etchant by irradiation with light or a positive type resin which becomes soluble in an etchant by irradiation with light can be used for the insulator 614.

An EL layer 616 and a second electrode 617 are formed over the first electrode 613. Here, a material having a high work function is preferably used as a material for the first electrode 613 serving as an anode. For example, the first electrode 613 can be formed by using stacked layers of a titanium nitride film and a film including aluminum as its main component; a three-layer structure of a titanium nitride film, a film including aluminum as its main component, and a titanium nitride film; or the like as well as a single-layer film such as an ITO film, an indium tin oxide film containing silicon, an indium oxide film containing 2 to 20 wt % of zinc oxide, a titanium nitride film, a chromium film, a tungsten film, a Zn film, or a Pt film. When the first electrode 613 has a stacked structure, the electrode 613 shows low resistance enough to serve as a wiring, giving favorable ohmic contact.

In addition, the EL layer 616 is formed by various methods such as an evaporation method using an evaporation mask, an ink-jet method, and a spin coating method. The EL layer 616 includes the anthracene derivative of the present invention described in Embodiment Mode 2. Further, the EL layer 166 may be formed using another material including a low molecular compound or a high molecular compound (including oligomer and dendrimer).

As a material used for the second electrode 617, which is formed over the EL layer 616 and serves as a cathode, a material having a low work function (Al, Mg, Li, Ca, or an alloy or a compound thereof such as MgAg, MgIn, AlLi, LiF, or $CaF_2$) is preferably used. In a case where light generated in the EL layer 616 is transmitted through the second electrode 617, stacked layers of a metal thin film and a transparent conductive film (ITO, indium oxide containing 2 to 20 wt % of zinc oxide, indium oxide-tin oxide containing silicon or silicon oxide, zinc oxide (ZnO), or the like) are preferably used as the second electrode 617.

By attachment of the sealing substrate 604 to the element substrate 610 with the sealing material 605, a light-emitting element 618 that is included in the invention shown in Embodiment Modes 3 to 7 is provided in the space 607 surrounded by the element substrate 610, the sealing substrate 604, and the sealing material 605. It is to be noted that the space 607 is filled with an inert gas (nitrogen, argon, or the like). There is also a case where the space 607 is filled with the sealing material 605.

It is to be noted that an epoxy-based resin is preferably used as the sealing material 605. It is desired that the material allows as little moisture and oxygen as possible to penetrate. As the sealing substrate 604, a plastic substrate formed using FRP (Fiberglass-Reinforced Plastics), PVF (polyvinyl fluoride), polyester, acrylic resin, or the like can be used as well as a glass substrate or a quartz substrate.

As described above, a light-emitting device including the anthracene derivative of the present invention can be obtained.

Since the anthracene derivative described in Embodiment Mode 2 is used for the light-emitting device of the present invention, a light-emitting device having high performance can be obtained. Specifically, a light-emitting device having a long lifetime can be obtained.

Also, since the anthracene derivative of the present invention has high luminous efficiency, a light-emitting device with low power consumption can be obtained.

Further, since an anthracene derivative of the present invention is capable of emitting blue light with high color purity, the anthracene derivative can be favorably used for a full-color display. Further, since the anthracene derivative of the present invention is capable of emitting blue light with high reliability and low power consumption, it can be favorably used for a full-color display.

Further, since the anthracene derivative of the present invention is capable of blue light emission with high color purity, a light-emitting device with high color reproducibility can be obtained.

Figure 5A:
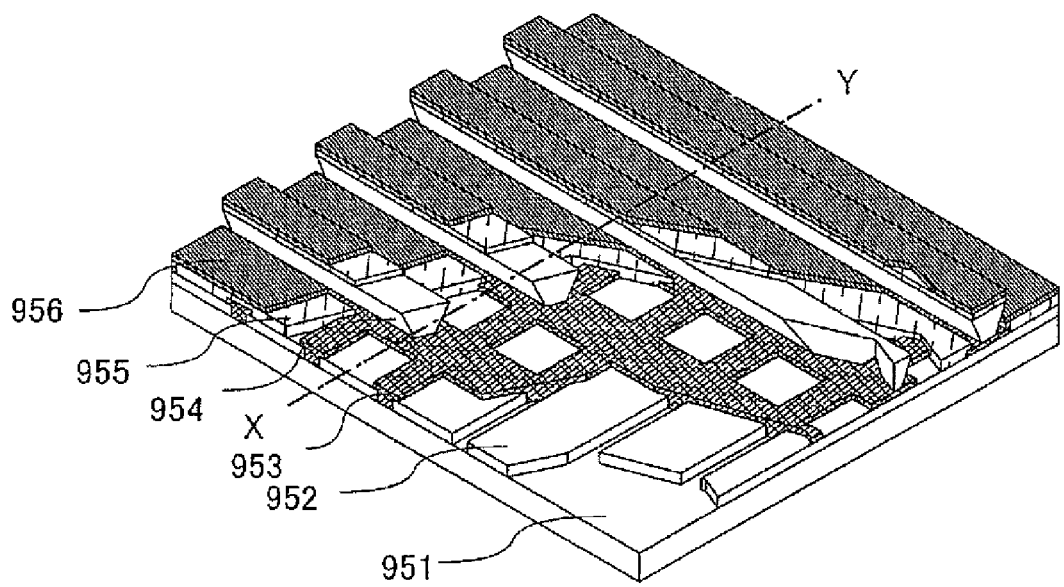
FIGS. 5A and 5B are views explaining a light-emitting device of the present invention.
Figure 5B:
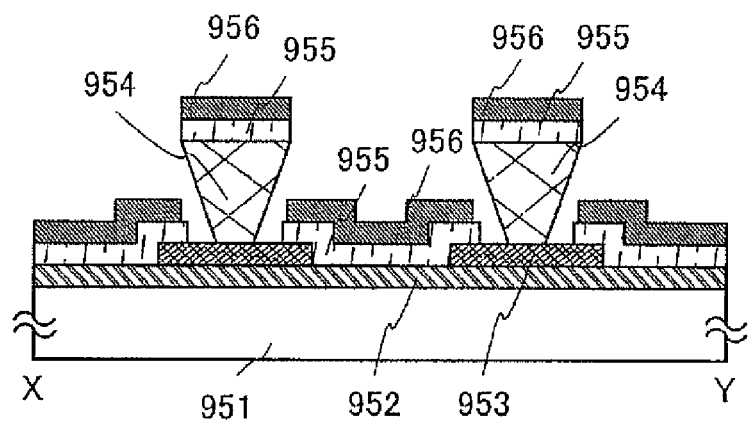

As described above, an active-matrix light-emitting device that controls driving a light-emitting element with a transistor is described in this embodiment mode; however, a passive-matrix light-emitting device may be used. A perspective view of a passive-matrix light-emitting device manufactured to which the present invention is applied is shown in FIG. 5A. FIG. 5A is a perspective view of a light-emitting device, and FIG. 5B is a cross-sectional view of FIG. 5A taken along a line X-Y. In FIGS. 5A and 5B, an EL layer 955 is provided between an electrode 952 and an electrode 956 over a substrate 951. An end of the electrode 952 is covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a short side is trapezoidal, and a base (a side expanding in a similar direction as a plane direction of the insulating layer 953 and in contact with the insulating layer 953) is shorter than an upper side (a side expanding in a similar direction as the plane direction of the insulating layer 953 and not in contact with the insulating layer 953). The partition layer 954 provided in this manner allows prevention of defects of a light-emitting element due to static electricity. A light-emitting device with high reliability and a long lifetime can be also obtained in the case of the passive-matrix light-emitting device by using the light-emitting element of the present invention. Further, a light-emitting device with low power consumption can be obtained.

Embodiment Mode 9

In this embodiment mode, an electronic device of the present invention partially including the light-emitting device described in Embodiment Mode 8 will be described. The electronic device of the present invention includes the anthracene derivative described in Embodiment Mode 2, and has a display portion with high reliability and a long lifetime.

Also, the electronic device of the present invention has a display portion with low power consumption.

As an electronic device including a light-emitting element manufactured using the anthracene derivative of the present invention, a camera such as a video camera or a digital camera, a goggle type display, a navigation system, an audio reproducing device (car audio component stereo, audio component stereo, or the like), a computer, a game machine, a portable information terminal (mobile computer, mobile phone, portable game machine, electronic book, or the like), and an image reproducing device provided with a recording medium (specifically, a device capable of reproducing a recording medium such as a Digital Versatile Disc (DVD) and provided with a display device that can display the image), and the like are given. Specific examples of these electronic devices are shown in FIGS. 6A to 6D.

Figure 6A:
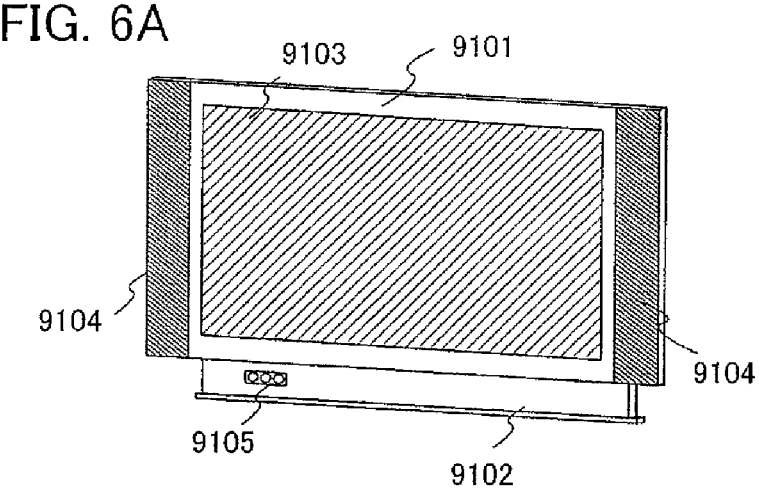
FIGS. 6A to 6D are views each explaining an electronic device of the present invention.

FIG. 6A shows a television device according to the present invention, which includes a housing 9101, a supporting base 9102, a display portion 9103, a speaker portion 9104, a video input terminal 9105, and the like. In the television device, the display portion 9103 has light-emitting elements similar to those described in Embodiment Modes 3 to 7, and the light-emitting elements are arranged in matrix. The features of the light-emitting element are exemplified by high luminous efficiency and long lifetime. The display portion 9103 which includes the light-emitting elements has similar features. Therefore, in the television device, image quality is scarcely deteriorated and low power consumption is achieved. Owing to these features, deterioration compensation function and power supply circuits can be significantly reduced or downsized in the television device, which enables reduction of the size and weight of the housing 9101 and supporting base 9102. In the television device according to the present invention, low power consumption, high image quality, and small size and lightweight are achieved; therefore, a product which is suitable for living environment can be provided. Also, since the anthracene derivative described in Embodiment Mode 1 is capable of blue light emission with high color purity, a full-color display is possible, and a television device having a display portion with high color reproducibility can be obtained. Further, a television device having a display portion with a long lifetime can be obtained.

Figure 6B:
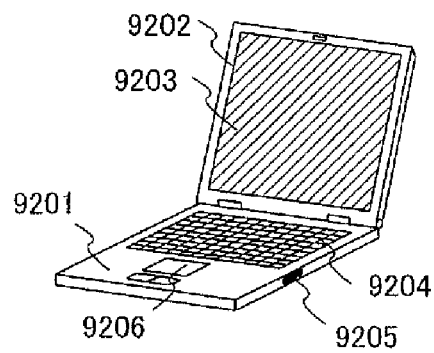

FIG. 6B shows a computer according to the present invention, which includes a main body 9201, a housing 9202, a display portion 9203, a keyboard 9204, an external connection port 9205, a pointing device 9206, and the like. In the computer, the display portion 9203 has light-emitting elements similar to those described in Embodiment Modes 3 to 7, and the light-emitting elements are arranged in matrix. The features of the light-emitting element are exemplified by high luminous efficiency and long lifetime. The display portion 9203 which includes the light-emitting elements has similar features. Therefore, in the computer, image quality is scarcely deteriorated and lower power consumption is achieved. Owing to these features, deterioration compensation function and power supply circuits can be significantly reduced or downsized in the computer; therefore, small sized and lightweight main body 9201 and housing 9202 can be achieved. In the computer according to the present invention, low power consumption, high image quality, and small size and lightweight are achieved; therefore, a product which is suitable for an environment can be supplied. Further, since the anthracene derivative described in Embodiment Mode 1 is capable of blue light emission with high color purity, a full-color display is possible, and a computer having a display portion with high color reproducibility can be obtained. Further, a computer having a display portion with a long lifetime can be obtained.

Figure 6C:
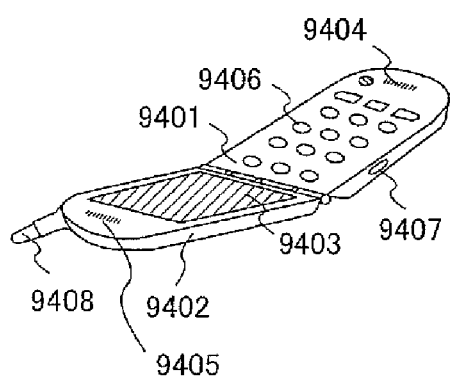

FIG. 6C shows a mobile phone according to the present invention, which includes a main body 9401, a housing 9402, a display portion 9403, an audio input portion 9404, an audio output portion 9405, an operation key 9406, an external connection port 9407, an antenna 9408, and the like. In the mobile phone, the display portion 9403 has light-emitting elements similar to those described in Embodiment Modes 3 to 7, and the light-emitting elements are arranged in matrix. The features of the light-emitting element are exemplified by high luminous efficiency and long lifetime. The display portion 9403 which includes the light-emitting elements has similar features. Therefore, in the mobile phone, image quality is scarcely deteriorated and lower power consumption is achieved. Owing to these features, deterioration compensation function and power supply circuits can be significantly reduced or downsized in the mobile phone; therefore, small sized and lightweight main body 9401 and housing 9402 can be achieved. In the mobile phone according to the present invention, low power consumption, high image quality, and a small size and lightweight are achieved; therefore, a product which is suitable for carrying can be provided. Further, since the anthracene derivative described in Embodiment Mode 1 is capable of blue light emission with high color purity, a full-color display is possible, and a mobile phone having a display portion with high color reproducibility can be obtained. Further, a mobile phone having a display portion with a long lifetime can be obtained.

Figure 6D:
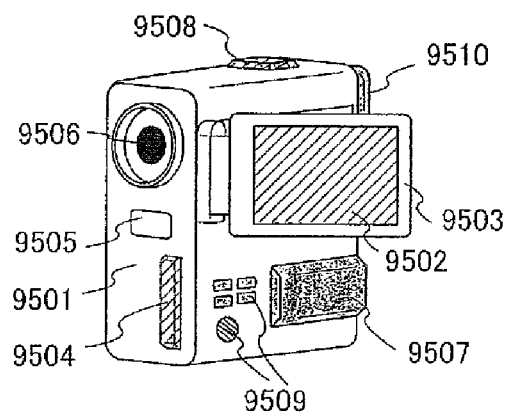

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has light-emitting elements similar to those described in Embodiment Modes 3 to 7, and the light-emitting elements are arranged in matrix. The features of the light-emitting element are exemplified by high luminous efficiency and long lifetime. The display portion 9502 which includes the light-emitting elements has similar features. Therefore, in the camera, image quality is scarcely deteriorated and lower power consumption can be achieved. Owing to these features, deterioration compensation function and power supply circuits can be significantly reduced or downsized in the camera; therefore, a small sized and lightweight main body 9501 can be achieved. In the camera according to the present invention, low power consumption, high image quality, and small size and lightweight are achieved; therefore, a product which is suitable for carrying can be provided. Further, since the anthracene derivative described in Embodiment Mode 1 is capable of blue light emission with high color purity, a full-color display is possible, and a camera having a display portion with high color reproducibility can be obtained. Further, a camera having a display portion with a long lifetime can be obtained.

As described above, the applicable range of the light-emitting device of the present invention is so wide that the light-emitting device can be applied to electronic devices in various fields. By using the anthracene derivative of the present invention, electronic devices which have display portions with a long lifetime can be provided. Further, electronic devices which have display portions with high color reproducibility can be obtained.

The light-emitting device of the present invention can also be used as a lighting system. One mode using the light-emitting element of the present invention as the lighting system will be described with reference to FIG. 7.

Figure 7:
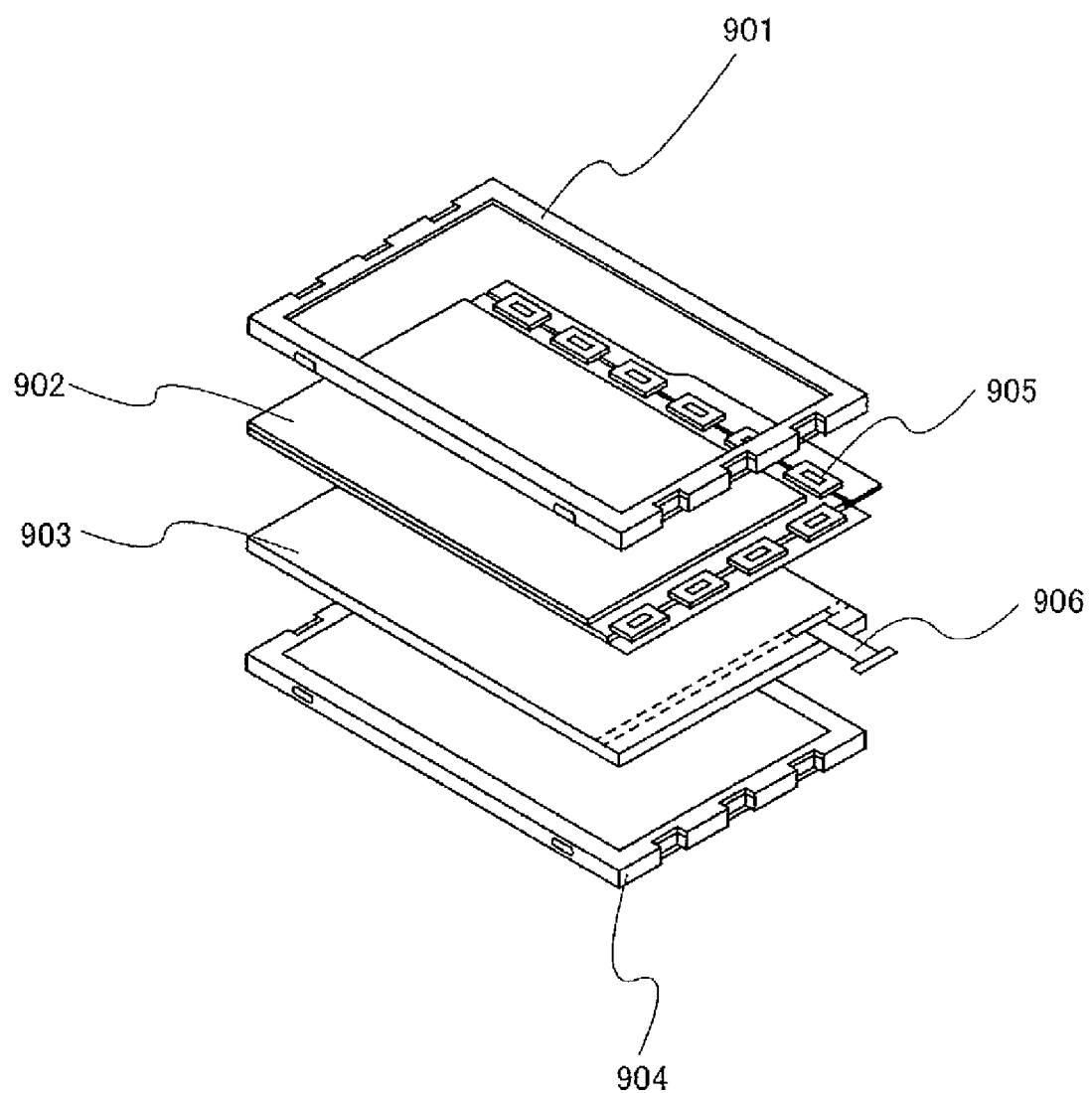
FIG. 7 is a view explaining an electronic device of the present invention.

FIG. 7 shows an example of a liquid crystal display device using the light-emitting device of the present invention as a backlight. The liquid crystal display device shown in FIG. 7 includes a housing 901, a liquid crystal layer 902, a backlight 903, and a housing 904, and the liquid crystal layer 902 is connected to a driver IC 905. The light-emitting device of the present invention is used for the backlight 903, and current is supplied through a terminal 906.

By using the light-emitting device of the present invention as the backlight of the liquid crystal display device, a backlight with reduced power consumption and high luminous efficiency can be obtained. The light-emitting device of the present invention is a lighting system with plane light emission, and can have a large area. Therefore, the backlight can have a large area, and a liquid crystal display device having a large area can be obtained. Furthermore, the light-emitting device of the present invention has a thin shape and has low power consumption; therefore, a thin shape and low power consumption of a display device can also be achieved. Since the light-emitting device of the present invention has a long lifetime, a liquid crystal display device using the light-emitting device of the present invention also has a long lifetime.

Figure 8:
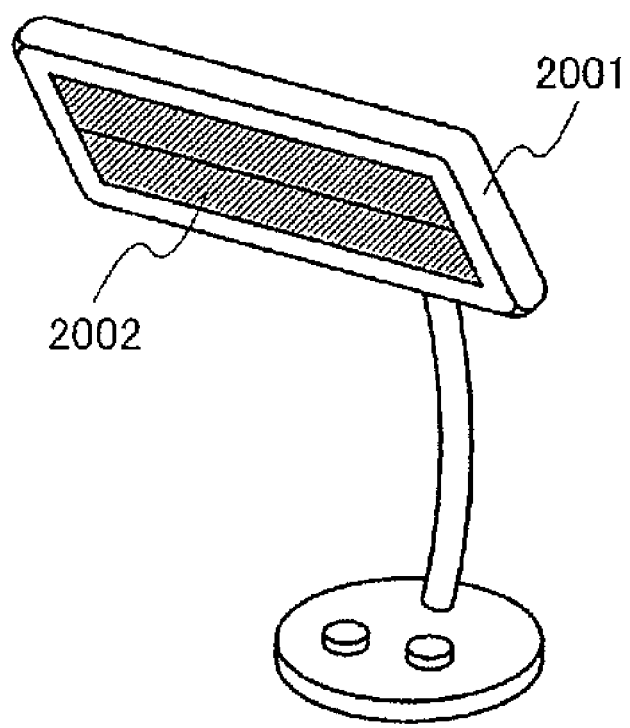
FIG. 8 is a view explaining a lighting system of the present invention.

FIG. 8 shows an example of the light-emitting device to which the present invention is applied. In FIG. 8, an example for the application to a table lamp as a lighting system is illustrated. A table lamp shown in FIG. 8 includes a housing 2001 and a light source 2002, and the light-emitting device of the present invention is used as the light source 2002. The light-emitting device of the present invention has high luminous efficiency and has a long lifetime; therefore, a table lamp also has high luminous efficiency and a long lifetime.

Figure 9:
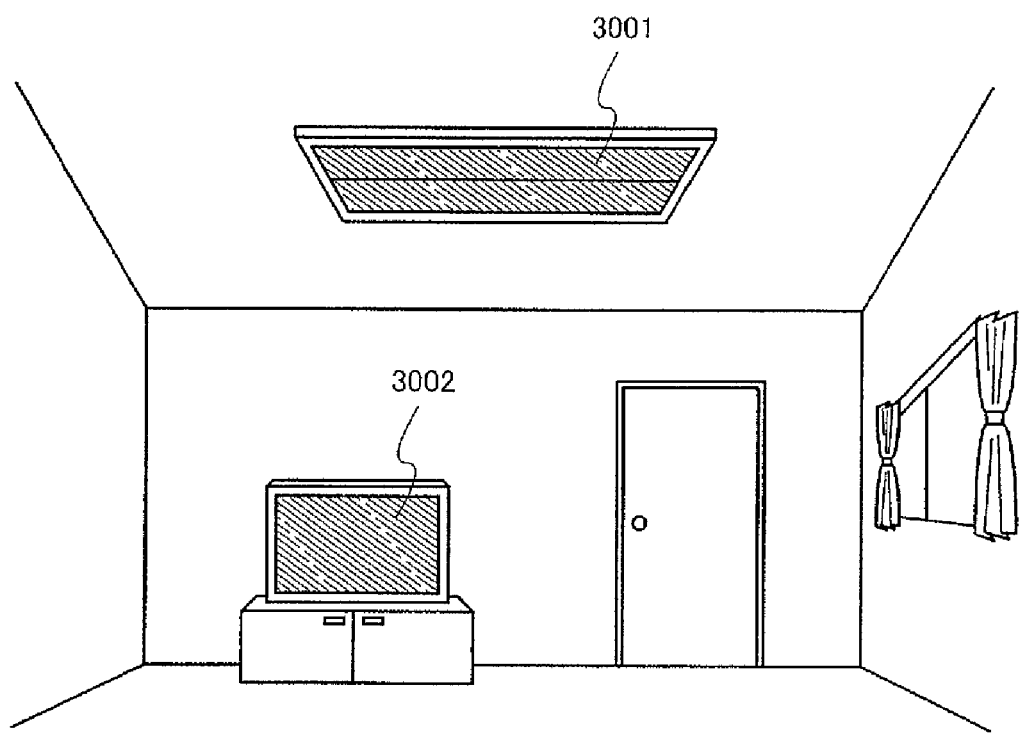
FIG. 9 is a view explaining a lighting system of the present invention.

FIG. 9 shows an example of a light-emitting device to which the present invention is applied. FIG. 9 shows an example for the application to an indoor lighting system 3001. Since the light-emitting device of the present invention can also have a large area, the light-emitting device of the present invention can be used as a lighting system having a large emission area. Further, the light-emitting device of the present invention has a thin shape and consumes low power; therefore, the light-emitting device of the present invention can be used as a lighting system having a thin shape and low-power consumption. A television device 3002 according to the present invention as described in FIG. 6A is placed in a room in which the light-emitting device to which the present invention is applied is used as the indoor lighting device 3001, and public broadcasting and movies can be watched. In such a case, since both of the devices consume low power, a powerful image can be watched in a bright room without concern about electricity charges.

Embodiment 1

In this embodiment, a synthesis method of 9-[4-(N-carbazolyl)]phenyl-10-phenylanthracene (abbreviation: CzPA) represented by a structural formula (11) will be described.

(11)

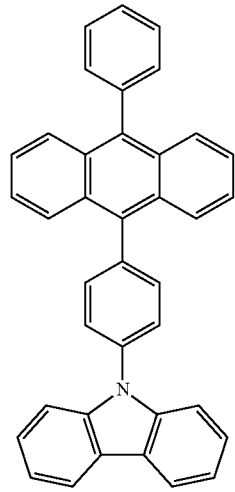

[Step 1] Synthesis of 9-bromo-10-phenylanthracene (i) Synthesis of 9-phenylanthracene A synthesis scheme of 9-phenylanthracene is shown in (B-1).

(B-1)

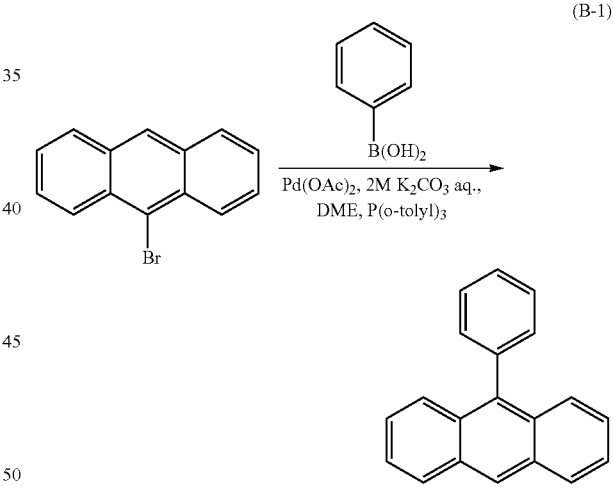

25.7 g (100 mmol) of 9-bromoanthracene, 12.8 g (105 mmol) of phenylboronic acid, 233 mg (1.0 mmol) of palladium acetate(II), and 913 mg (3.0 mmol) of tri(o-tolyl)phosphine were put into a 500-mL three-neck flask and nitrogen substitution was carried out. Then, 100 mL of ethylene glycol dimethyl ether and 75 mL (190 mmol) of a sodium carbonate aqueous solution (2.0 mol/L) were added thereto, and the reaction mixture was stirred at 90° C. for 5 hours. After the reaction, the reaction mixture was subjected to suction filtration to collect a precipitated solid. The obtained solid was dissolved into toluene, and the resulting solution was subjected to suction filtration through Florisil, celite, and then alumina. The filtrate was washed with water and saturated saline, and then an organic layer was dried with magnesium sulfate. This mixture is naturally filtrated, and the filtrate was condensed to obtain 25.0 g of a light-brown solid that was a target matter with the yield of 98%.

(ii) Synthesis of 9-bromo-10-phenylanthracene

A synthesis scheme of 9-bromo-10-phenylanthracene is shown in (B-2).

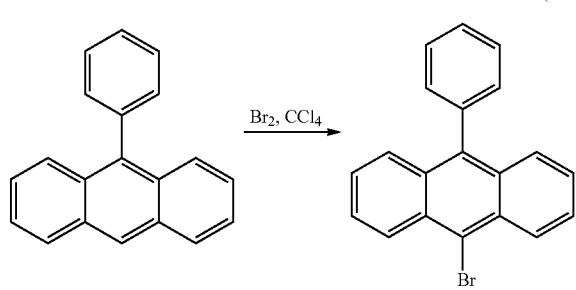

(B-2)

25.0 g (98.3 mmol) of 9-phenylanthracene was put into a 1-L three-neck flask, and 300 mL of carbon tetrachloride was added thereto. A solution in which 15.6 g (98.3 mmol) of bromine was dissolved in 40 mL of carbon tetrachloride was dropped in the reaction solution at the room temperature. After the dropping, the reaction solution was stirred at the room temperature for 1 hour. Thereafter, the reaction is completed by adding a sodium thiosulfate aqueous solution, and the solution was further stirred for 1 hour. An organic layer of the reaction mixture was washed with aqueous sodium hydroxide (2.0 mol/L) and saturated saline and dried with magnesium sulfate. This mixture was filtrated naturally, and the filtrate was condensed to obtain a solid. The solid was dissolved in toluene, and the solution was subjected to suction filtration through Florisil, celite, and then alumina. The filtrate was concentrated to obtain a solid, and the solid was recrystallized with a mixture solution of dichloromethane and hexane, whereby 27.8 g of a light yellow powdery solid that was a target matter was obtained with the yield of 85%.

[Step 2] Synthesis of 4-(carbazol-9-yl)phenylboronic acid

(i) Synthesis of N-(4-bromophenyl)carbazole

A synthesis scheme of N-(4-bromophenyl)carbazole is shown in (B-3).

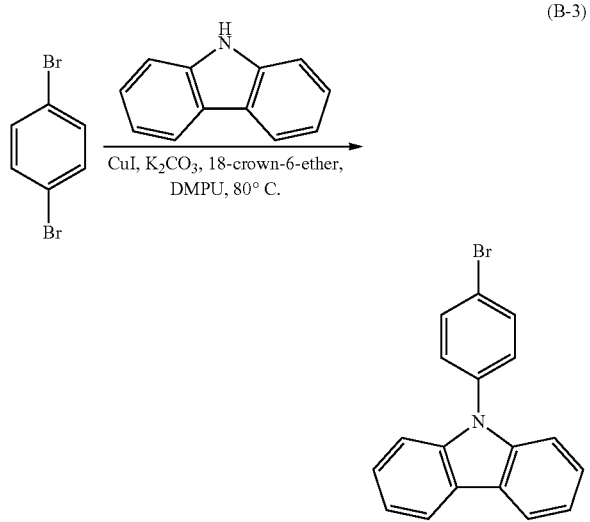

(B-3)

56.3 g (0.24 mol) of 1,4-dibromobenzene, 31.3 g (0.18 mol) of carbazole, 4.6 g (0.024 mol) of copper iodide(I), 66.3 g (0.48 mol) of potassium carbonate, and 2.1 g (0.008 mol) of 18-crown-6-ether were put into a 300-mL three-neck flask, and nitrogen substitution was carried out. Then, 8 mL of 1,3-dimethyl-3,4,5,6-tetrahydro-2(1H)-pyrimidinone (DMPU) was added thereto, and the reaction mixture was stirred at 180° C. for 6 hours. After the reaction mixture was cooled to the room temperature, a precipitate was removed by suction filtration. The filtrate was washed with a diluted hydrochloric acid, a saturated sodium hydrogen-carbonate aqueous solution, and a saturated saline solution in this order. An organic layer was dried with magnesium sulfate. After drying, the mixture was filtered naturally, and the filtrate was concentrated to obtain an oily substance. The substance was purified by silica gel column chromatography (hexane:ethyl acetate=9:1 as a developing solvent). The resulting solid was recrystallized with a mixture solvent of chloroform and hexane, whereby 20.7 g of a light brown plate-shaped crystal that was a target matter was obtained with the yield of 35%.

(ii) Synthesis of 4-(carbazol-9-yl)phenylboronic acid

A synthesis scheme of 4-(carbazol-9-yl)phenylboronic acid is shown in (B-4).

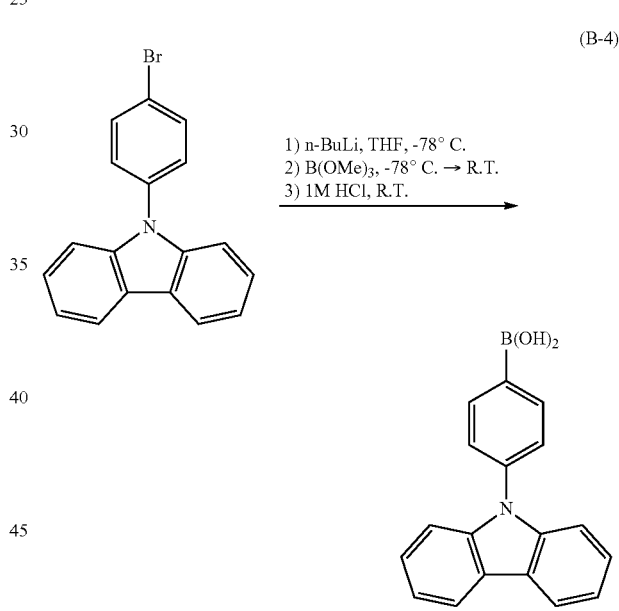

(B-4)

21.8 g (67.5 mmol) of N-(4-bromophenyl)carbazole was put into a 500-mL three-neck flask and nitrogen substitution was carried out. After that, 200 mL of tetrahydrofuran (THF) was added to keep the reaction system at −78° C. inside. 48.9 mL (74.3 mmol) of n-butyllithium (1.52 mol/L hexane solution) was dropped to this reaction solution, and the solution was stirred at the same temperature for 2 hours. 17.4 mL (155 mmol) of trimethyl borate was added and the solution was stirred at −78° C. for 1 hour, and thereafter, the solution was stirred for 12 hours while the reaction temperature was allowed to gradually increase to the room temperature. After reaction, 200 mL of hydrochloric acid (1 mol/L) was added to the reaction solution, and the solution was stirred at the room temperature for 1 hour. The reaction mixture was washed with water to extract a water layer with ethyl acetate. The extracted solution and an organic layer were washed with saturated saline together and dried with magnesium sulfate. After drying, the mixture was subjected to suction filtration, and the filtrate was condensed to obtain a solid. The solid was recrystallized with a mixed solution of chloroform and hexane, whereby 12.8 g of a white powdery solid that was a target matter was obtained with the yield of 66%.

[Step 3] Synthesis of
9-[4-(N-carbazolyl)]phenyl-10-phenylanthracene
(abbreviation: CzPA)

A synthesis scheme of CzPA is shown in (B-5).

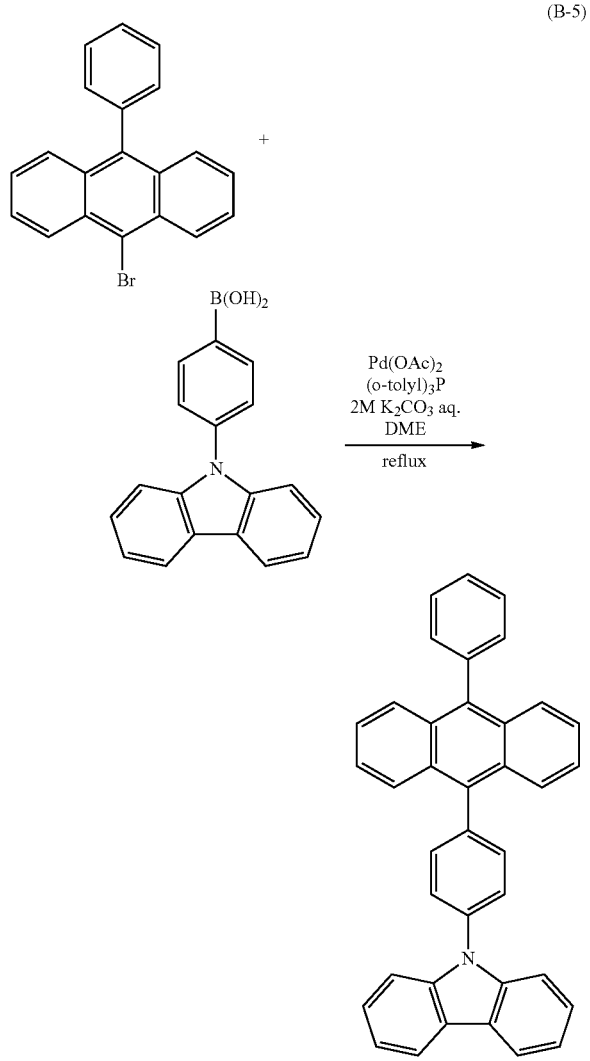

(B-5)

1.44 g (4.32 mmol) of 9-bromo-10-phenylanthracene, 1.49 g (5.19 mmol) of 4-(carbazol-9-yl)phenylboronic acid, 38.0 mg (0.17 mmol) of palladium acetate(II), and 0.36 g (1.21 mmol) of tris(o-tolyl)phosphine were put into a 100-mL three-neck flask and nitrogen substitution was carried out. Then, 10 mL of ethylene glycol dimethyl ether (DME) and 6.5 mL (13.0 mmol) of a sodium carbonate aqueous solution (2.0 mol/L) were added and the solution was stirred at 90° C. for 4 hours. After that, the reaction mixture was subjected to suction filtration to collect a precipitated solid. The obtained solid was dissolved into chloroform, and the solution was subjected to suction filtration through Florisil, celite, and then alumina. The filtrate was condensed to obtain a solid, and the solid was recrystallized with a mixture solvent of chloroform and hexane, whereby 1.81 g of a light yellow powdery solid that was a target matter was obtained with the yield of 85%. By a nuclear magnetic resonance measurement (NMR), it was confirmed that this compound was 9-[4-(N-carbazolyl)] phenyl-10-phenylanthracene (abbreviation: CzPA).

Figure 10A:
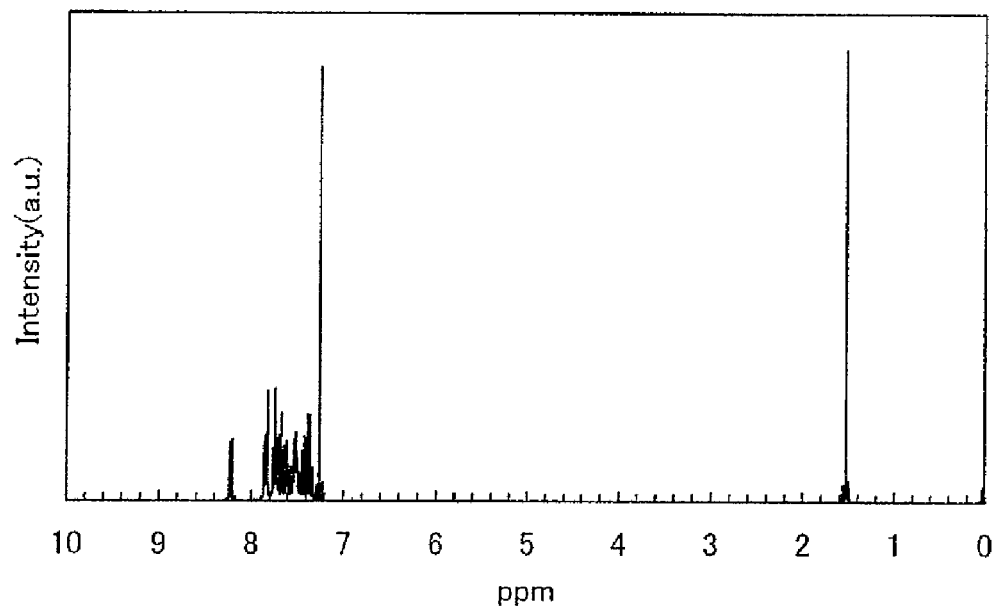
FIGS. 10A and 10B are graphs each showing $^1$H NMR of 9-[4-(N-carbazolyl)phenyl]-10-phenylanthracene.
Figure 10B:
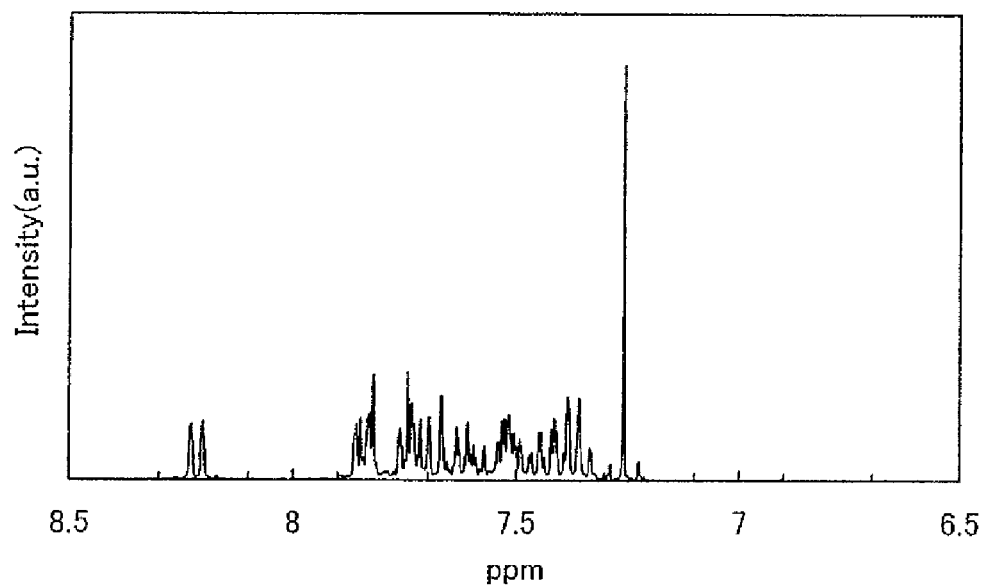

$^1$H NMR data of CzPA is shown below. $^1$H NMR (300 MHz, CDCl$_3$); δ=8.22 (d, J=7.8 Hz, 2H), 7.86-7.82 (m, 3H), 7.61-7.36 (m, 20H). The $^1$H NMR chart is shown in FIGS. 10A and 10B. It is to be noted that the range of 6.5 ppm to 8.5 ppm in FIG. 10A, which is expanded, is shown in FIG. 10B.

The thermogravimetry-differential thermal analysis (TG-DTA) of CzPA was performed using a thermo-gravimetric/differential thermal analyzer (TG/DTA 320, product of Seiko Instruments Inc.). The thermophysical properties were evaluated under a nitrogen atmosphere at a rate of temperature rise of 10° C./min. As a result, based on the relationship between gravity and temperature (thermogravimetric measurement), the temperature under normal pressure was 348° C. that is the temperature at which the gravity is 95% or less of the gravity at the starting point of the measurement. The glass transition temperature and the melting point of CzPA, which were measured with a differential scanning calorimeter (Pyris 1 DSC, product of Perkin Elmer Co., Ltd.), were 125° C. and 305° C. respectively; thus, it was found that CzPA was thermally stable.

Figure 11:
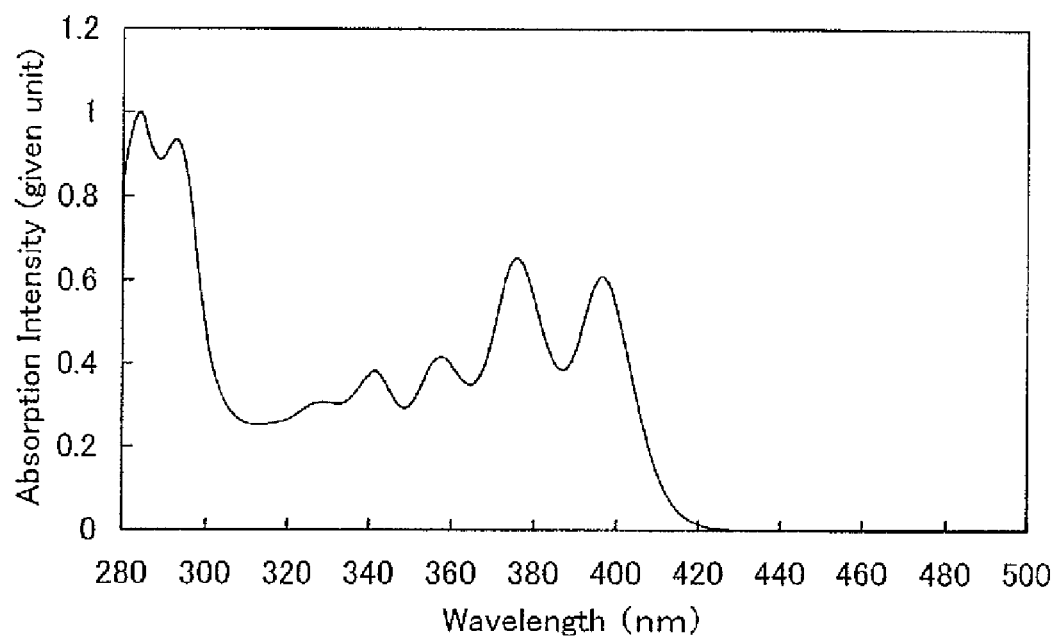
FIG. 11 is a graph showing an absorption spectrum of a toluene solution of 9-[4-(N-carbazolyl)phenyl]-10-phenylanthracene.
Figure 12:
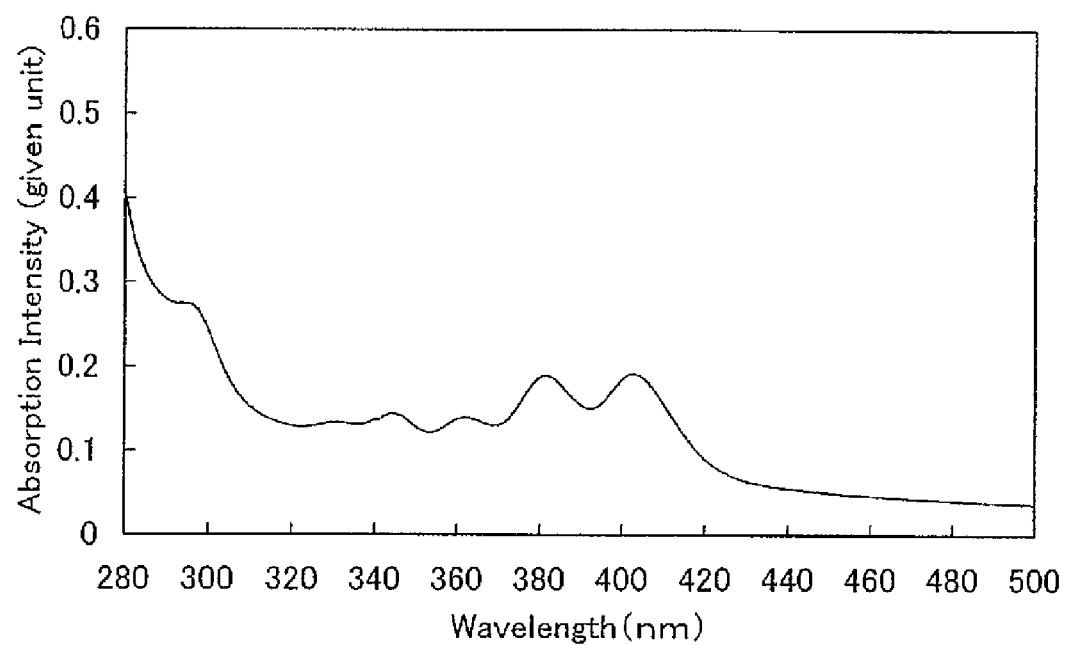
FIG. 12 is a graph showing an absorption spectrum of a thin film of 9-[4-(N-carbazolyl)phenyl]-10-phenylanthracene.
Figure 13:
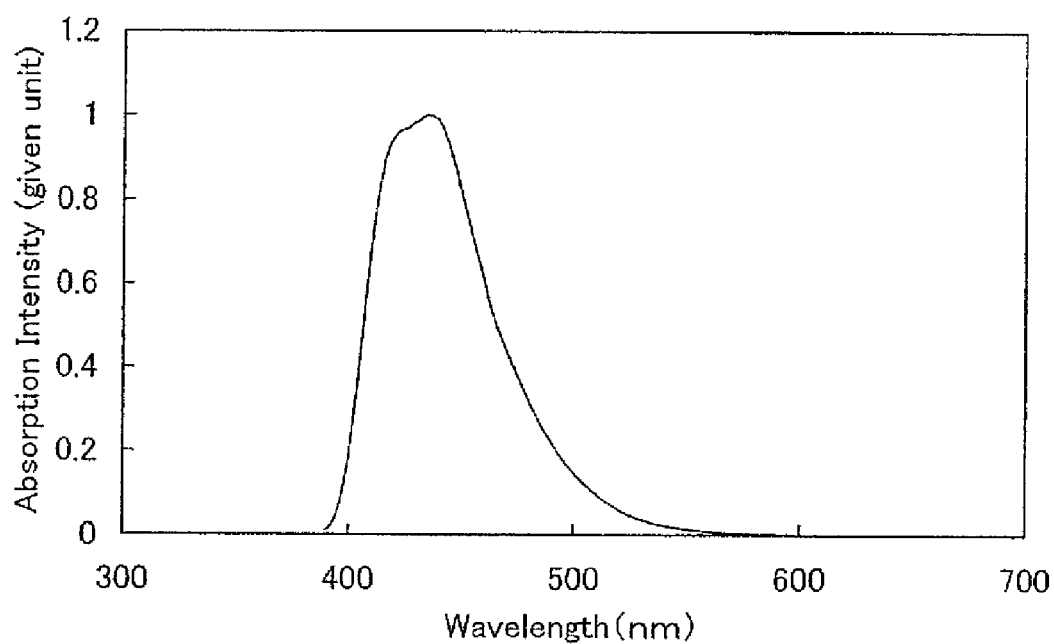
FIG. 13 is a graph showing an emission spectrum of a toluene solution of 9-[4-(N-carbazolyl)phenyl]-10-phenylanthracene.
Figure 14:
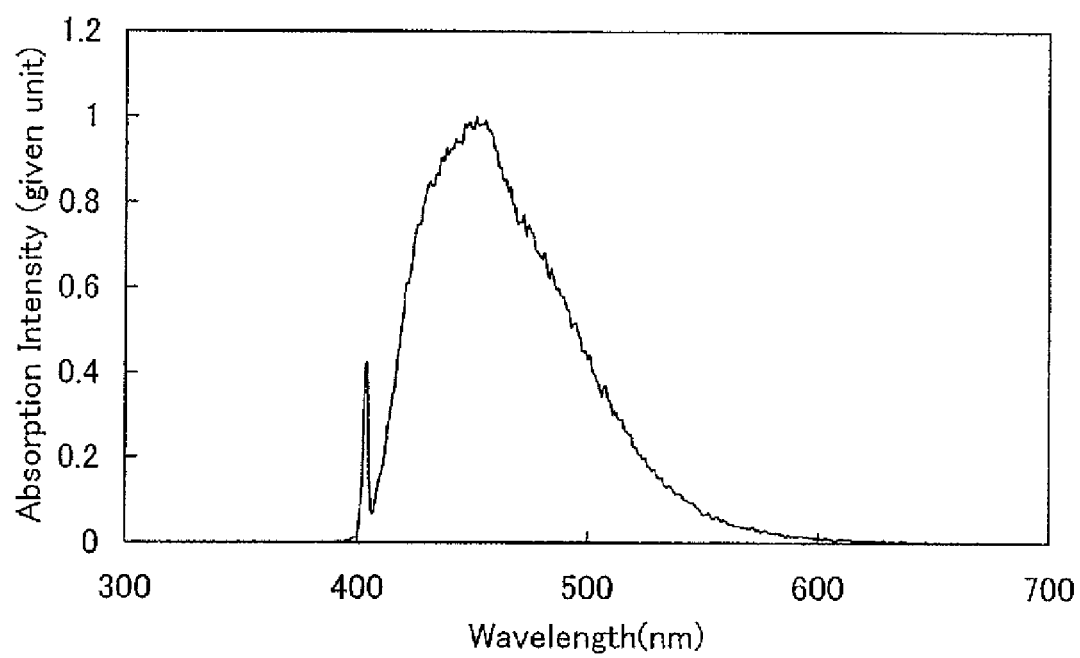
FIG. 14 is a graph showing an emission spectrum of a thin film of 9-[4-(N-carbazolyl)phenyl]-10-phenylanthracene.

FIG. 11 shows an absorption spectrum of a toluene solution of CzPA. FIG. 12 shows an absorption spectrum of a thin film of CzPA. An ultraviolet-visible spectrophotometer (V-550, manufactured by JASCO Corporation) was used for the measurement. The solution was put into a quartz cell and the thin film sample was evaporated on a quartz substrate to form the samples. The absorption spectra thereof, from each of which the absorption spectrum of quartz was subtracted, are shown in FIGS. 11 and 12. In FIGS. 11 and 12, the horizontal axis indicates the wavelength (nm) and the vertical axis indicates the absorption intensity (given unit). In the case of the toluene solution, absorption based on an anthracene skeleton was observed at around 376 nm and 396 nm, and absorption based on an anthracene skeleton was observed at around 381 nm and 403 nm in the case of the thin film. The emission spectrum of the toluene solution of CzPA (excitation wavelength: 370 nm) is shown in FIG. 13. The emission spectrum of the thin film of CzPA (excitation wavelength: 390 nm) is shown in FIG. 14. In FIGS. 13 and 14, the horizontal axis indicates the wavelength (nm), and the vertical axis indicates the emission intensity (given unit). The maximum emission wavelength was 448 nm (the excitation wavelength: 370 nm) in the case of the toluene solution, and at 451 nm (the excitation wavelength: 390 nm) in the case of the thin film. It was found that blue light emission was obtained.

In addition, the HOMO level of CzPA in the thin film state was −5.64 eV which was measured by a photoelectron spectrometer (AC-2, manufactured by Riken Keiki Co., Ltd.) in the air. Moreover, the absorption edge was obtained from Tauc plot using data on the absorption spectrum of the thin film of CzPA in FIG. 12. When the absorption edge was estimated as an optical energy gap, the energy gap was 2.95 eV. Therefore, the LUMO level was −2.69 eV.

Moreover, the oxidation-reduction reaction characteristic of CzPA was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Aldrich, 99.8%, catalog number: 22705-6) was used as a solvent. Tetra-n- butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode. The measurement was conducted at the room temperature. It is to be noted that the scanning speed of the CV measurement was set to be 0.1 V/s, and scanning of 100 cycles were conducted on each of the oxide side and the reduction side.

Figure 56:
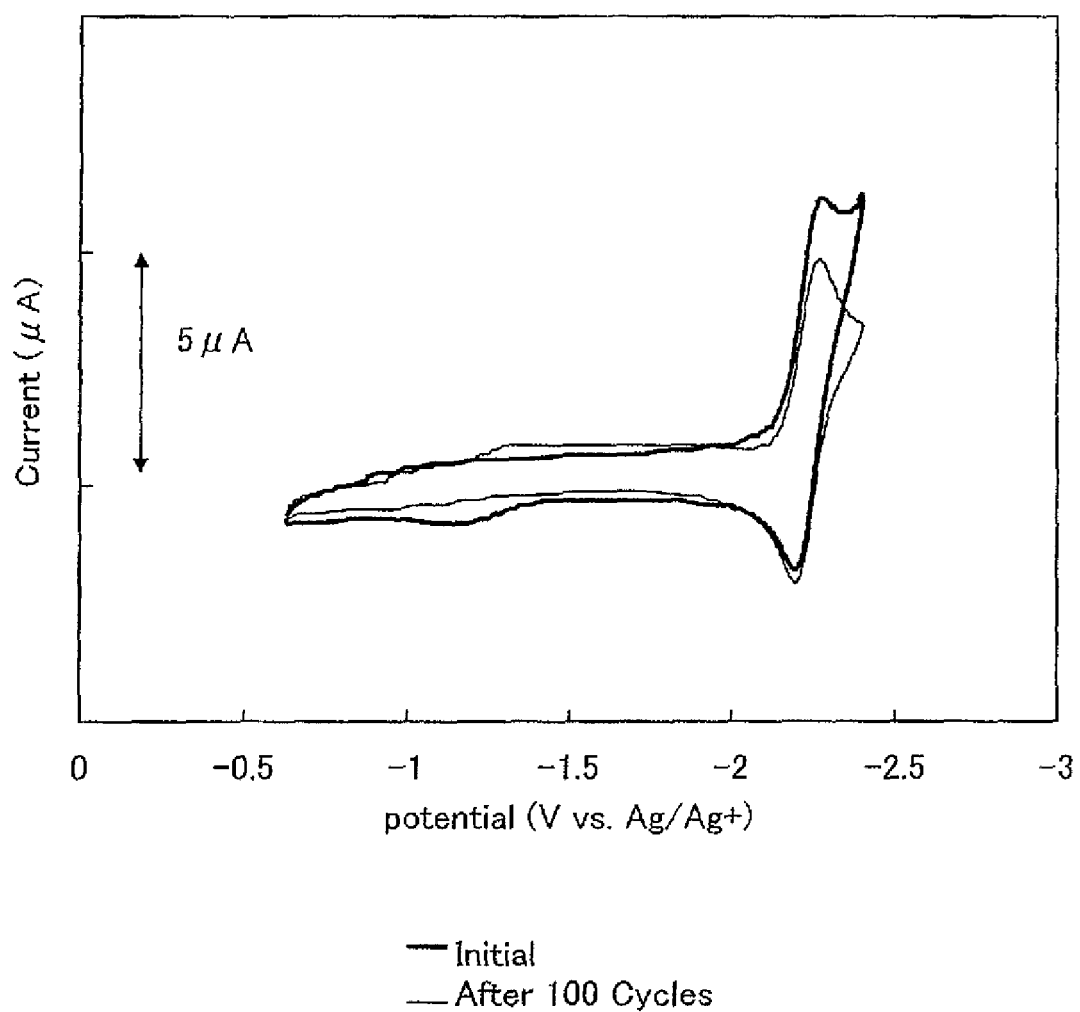
FIG. 56 is a graph showing a CV measurement result of a reduction side of 9-[4-(N-carbazolyl)phenyl]-10-phenylanthracene.
Figure 57:
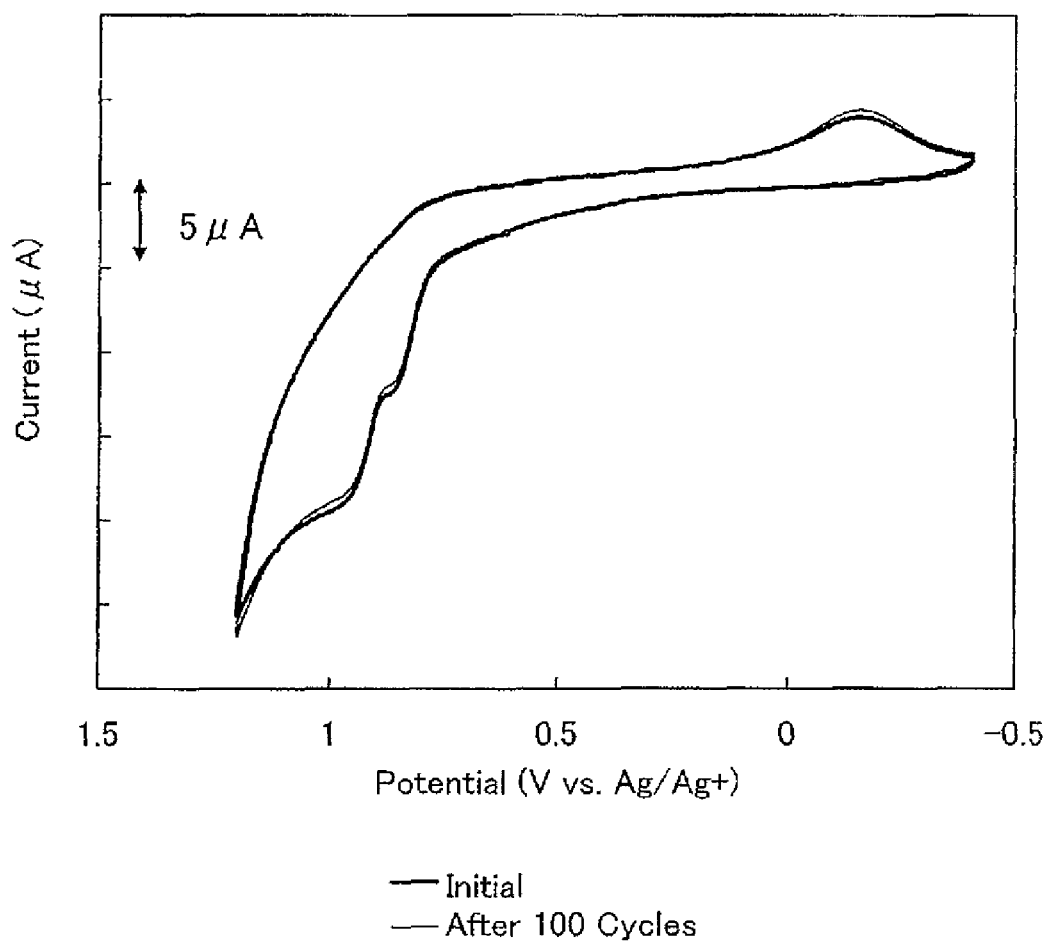
FIG. 57 is a graph showing a CV measurement result of an oxidation side of 9-[4-(N-carbazolyl)phenyl]-10-phenylanthracene.

FIG. 56 shows a result of the CV measurement on the reduction side of CzPA, and FIG. 57 shows a result of the CV measurement on the oxidation side of CzPA. In FIG. 56 and FIG. 57, the horizontal axis indicates the potential (V) of the work electrode with respect to the reference electrode, while the vertical axis indicates a value (μA) of current flowing between the work electrode and the auxiliary electrode.

From FIG. 56 and FIG. 57, in the case of CzPA, reversible peaks are shown on the oxide side and the reduction side. In addition, even when 100 cycles of oxidation to reduction or reduction to oxidation are repeated, peak intensity is hardly changed. From the above, it was found that the anthracene derivative of the present invention is extremely stable to the repetition of oxidation-reduction reaction.

Embodiment 2

In this embodiment, a synthesis method of 9-(biphenyl-4-yl)-10-[4-(carbazol-9-yl)phenyl]anthracene (abbreviation: PPCzPA) represented by a structural formula (12) will be described.

(12)

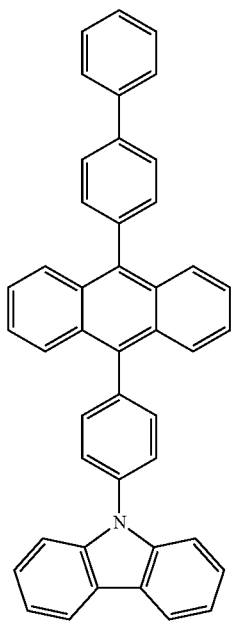

[Step 1] Synthesis of 9-(4-biphenyl)-10-bromoanthracene (i) Synthesis of 9-(biphenyl-4-yl)anthracene A synthesis scheme of 9-(biphenyl-4-yl)anthracene is shown in (C-1).

(C-1)

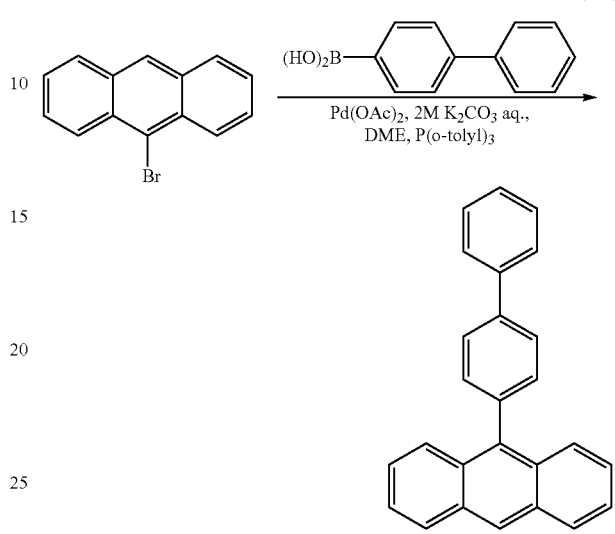

5.1 g (20 mmol) of 9-bromoanthracene, 4.0 g (20 mmol) of 4-biphenylboronic acid, and 246 mg (0.80 mmol) of tri(ortho-tolyl)phosphine were put into a 100-mL three neck flask and nitrogen substitution in the system was carried out. 20 mL of ethylene glycol dimethyl ether (DME) was added to this mixture, and the mixture was stirred under reduced pressure and degassed. After that, 45 mg (0.20 mmol) of palladium acetate(II) and 10 mL (2.0 mol/L) of a potassium carbonate solution were added. This reaction mixture was stirred at 80° C. for 3 hours under nitrogen gas stream. Then, the reaction mixture was cooled to the room temperature, and a solid that was precipitated was collected by suction filtration. The collected solid was dissolved in toluene, and the solution was subjected to suction filtration through Florisil, celite, and then alumina. The filtrate was condensed to obtain a solid, and the solid was recrystallized with ethanol, whereby 5.4 g of a white powdery solid, which was a target matter, was obtained with the yield of 81%.

(ii) Synthesis of 9-(biphenyl-4-yl)-10-bromoanthracene

A synthesis scheme of 9-(biphenyl-4-yl)-10-bromoanthracene is shown in (C-2).

(C-2)

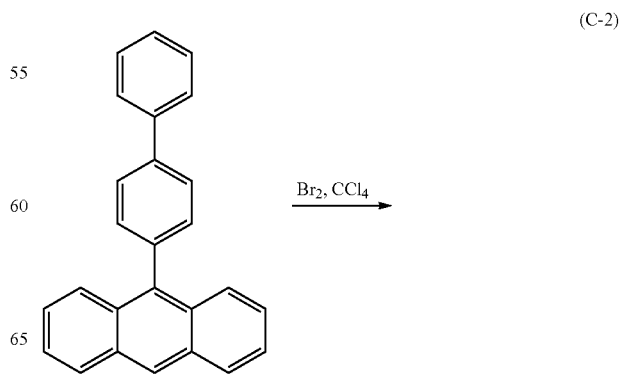

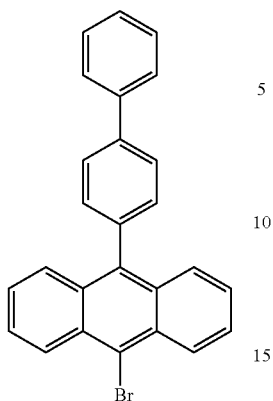

5.3 g (16 mmol) of 9-(biphenyl-4-yl)anthracene and 90 mL of carbon tetrachloride were put into a 200-mL three-neck flask and were stirred. A solution in which 2.8 g (18 mmol) of bromine was dissolved in 10 mL of carbon tetrachloride was dropped into the above solution through a dropping funnel. After that, the solution was stirred at the room temperature for 1 hour, and a sodium thiosulfate aqueous solution was added to the reaction solution to complete the reaction. A water layer of the reaction mixture was extracted by chloroform, and the extracted solution and an organic layer were together washed with a saturated sodium hydrogen carbonate solution and saturated saline in this order. The organic layer was dried with magnesium sulfate, and the mixture was filtrated naturally to remove the magnesium sulfate. Then, the filtrate was condensed to obtain a solid. The obtained solid was recrystallized with ethanol, whereby 5.4 g of a yellow powdery solid, which was a target matter, was obtained with the yield of 82%.

[Step 2] Synthesis of 9-(biphenyl-4-yl)-10-[4-(carbazol-9-yl)phenyl]anthracene (abbreviation: PPCzPA)

A synthesis scheme of PPCzPA is shown in (C-3).

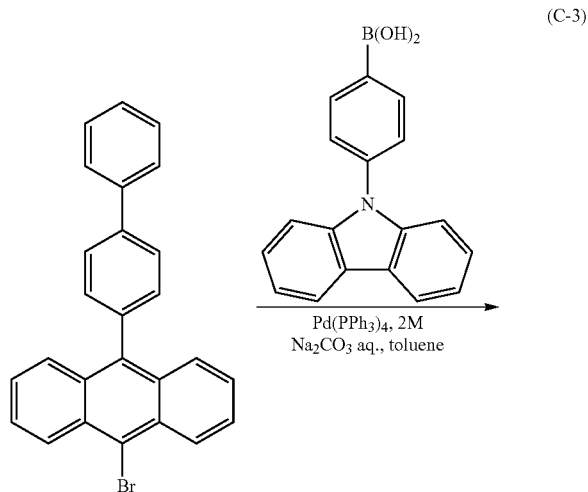

(C-3)

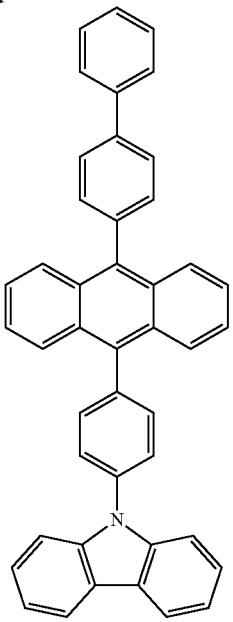

3.0 g (7.3 mmol) of 9-(biphenyl-4-yl)-10-bromoanthracene and 2.1 g (7.3 mmol) of 4-(carbazol-9-yl)phenylboronic acid were put into a 100-mL three-neck flask, and nitrogen substitution in the system was carried out. 25 mL of ethylene glycol dimethyl ether (DME) and 10 mL (2.0 mol/L) of a potassium carbonate solution were added to this mixture, and the mixture was stirred under reduced pressure and degassed. After that, 85 mg (0.017 mmol) of tetrakis(triphenylphosphine)palladium(0) was added. This reaction mixture was stirred at 80° C. for 12 hours under nitrogen gas stream. Then, the reaction mixture was cooled to the room temperature, and a solid that was precipitated was collected by suction filtration. The collected solid was dissolved in toluene, and the solution was subjected to suction filtration through Florisil, celite, and then alumina. The filtrate was condensed to obtain a solid, and the solid was recrystallized with a mixture solvent of chloroform and hexane, whereby 2.9 g of a light yellow powdery solid, which was a target matter, was obtained with the yield of 72%. By a nuclear magnetic resonance measurement (NMR), it was confirmed that this compound was 9-(biphenyl-4-yl)-10-[4-(carbazol-9-yl)phenyl]anthracene (abbreviation: PPCzPA).

Figure 15A:
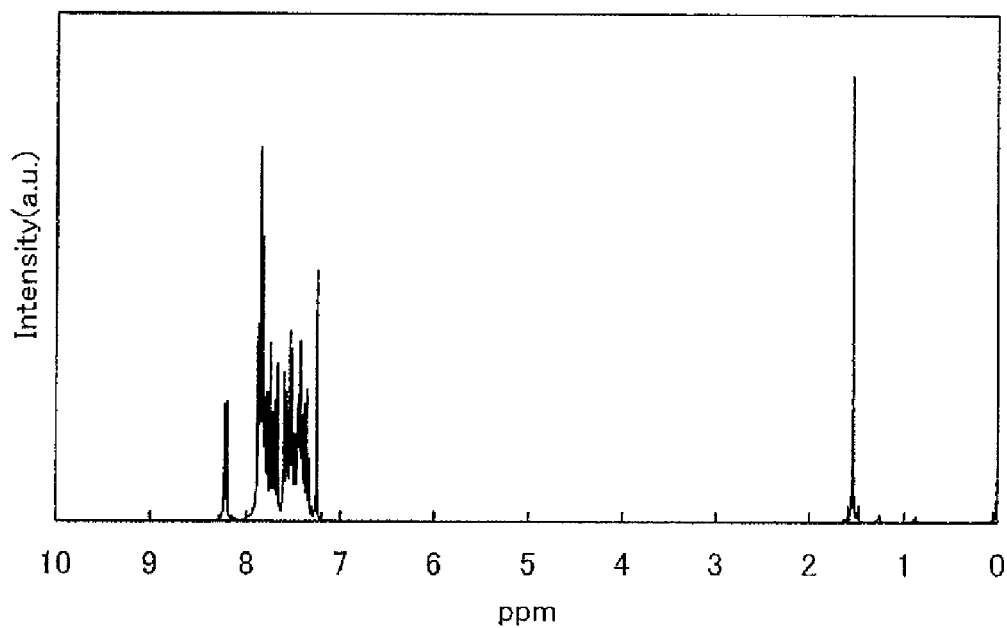
FIGS. 15A and 15B are graphs each showing $^1$H NMR of 9-(biphenyl-4-yl)-10-[4-(carbazol-9-yl)phenyl]anthracene.
Figure 15B:
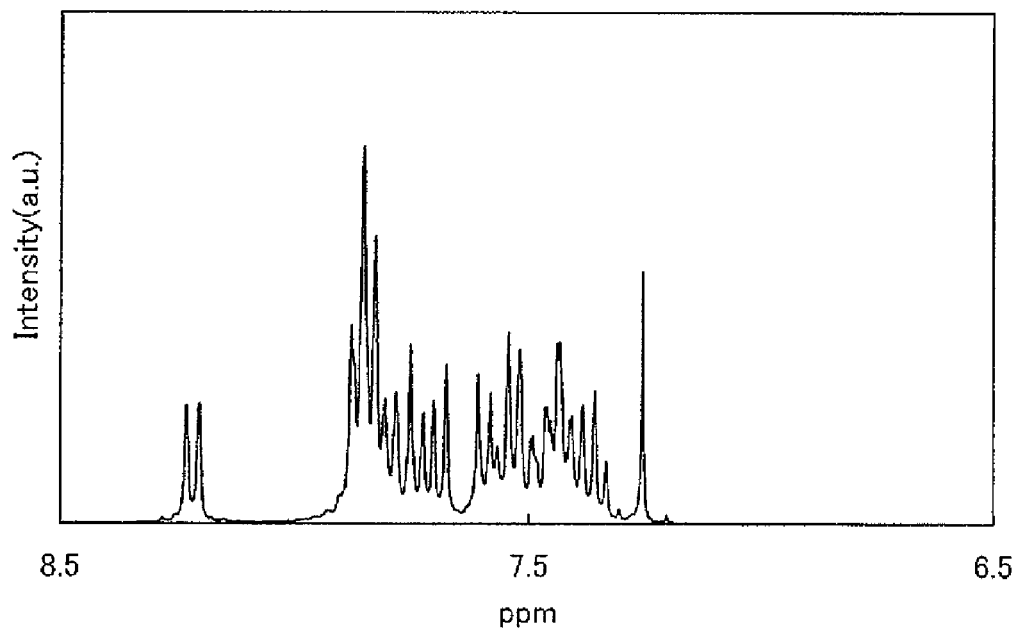

$^1$H NMR data of PPCzPA is shown below. $^1$H NMR (300 MHz, CDCl$_3$); δ=7.33-7.61 (m, 13H), 7.68-7.88 (m, 14H), 8.21 (d, J=7.8 Hz, 2H). The $^1$H NMR chart is shown in FIGS. 15A and 15B. It is to be noted that the range of 6.5 ppm to 8.5 ppm in FIG. 15A, which is expanded, is shown in FIG. 15B.

When 2.18 g of the PPCzPA obtained by the above synthesis method was purified by sublimation for 12 hours under such condition that the flow of argon was 3.0 mL/min, the pressure was 7.0 Pa, and the heating temperature was 290° C., 1.61 g of a light yellow needle crystal of PPCzPA was obtained with the yield of 74%.

The thermogravimetry-differential thermal analysis (TG-DTA) of PPCzPA was performed using a thereto-gravimetric/differential thermal analyzer (TG/DTA 320, product of Seiko Instruments Inc.). As a result, based on the relationship between gravity and temperature (thermogravimetric measurement), the temperature under normal pressure was 390° C., which is the temperature at which the gravity is 95% or less of the gravity at the starting point of the measurement. It was found that PPCzPA had favorable heat resistance.

Figure 16:
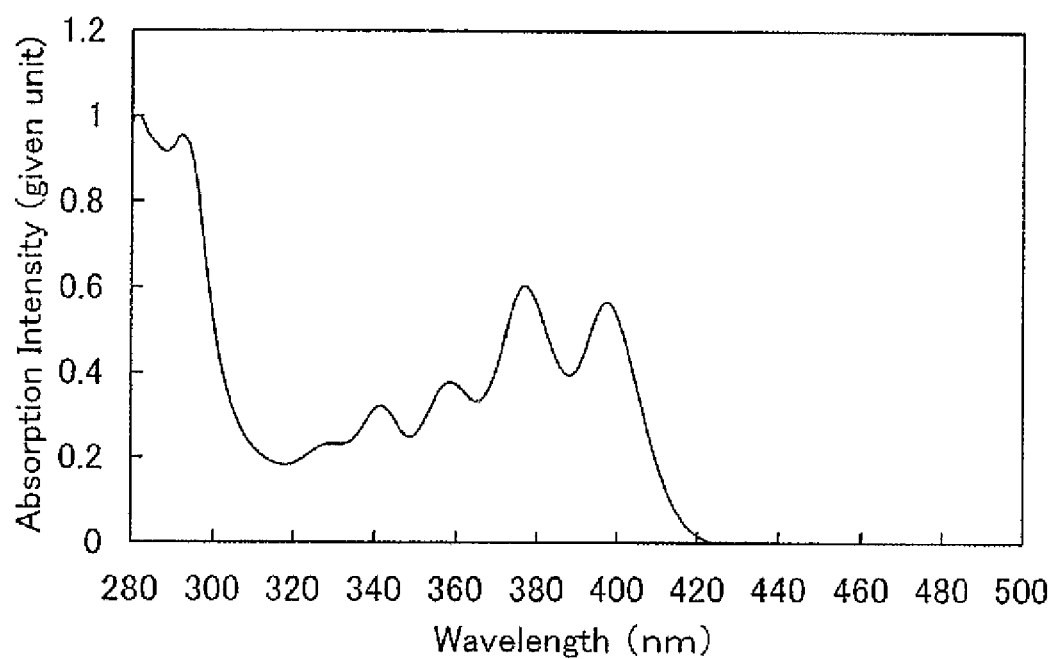
FIG. 16 is a graph showing an absorption spectrum of a toluene solution of 9-(biphenyl-4-yl)-10-[4-(carbazol-9-yl)phenyl]anthracene.
Figure 17:
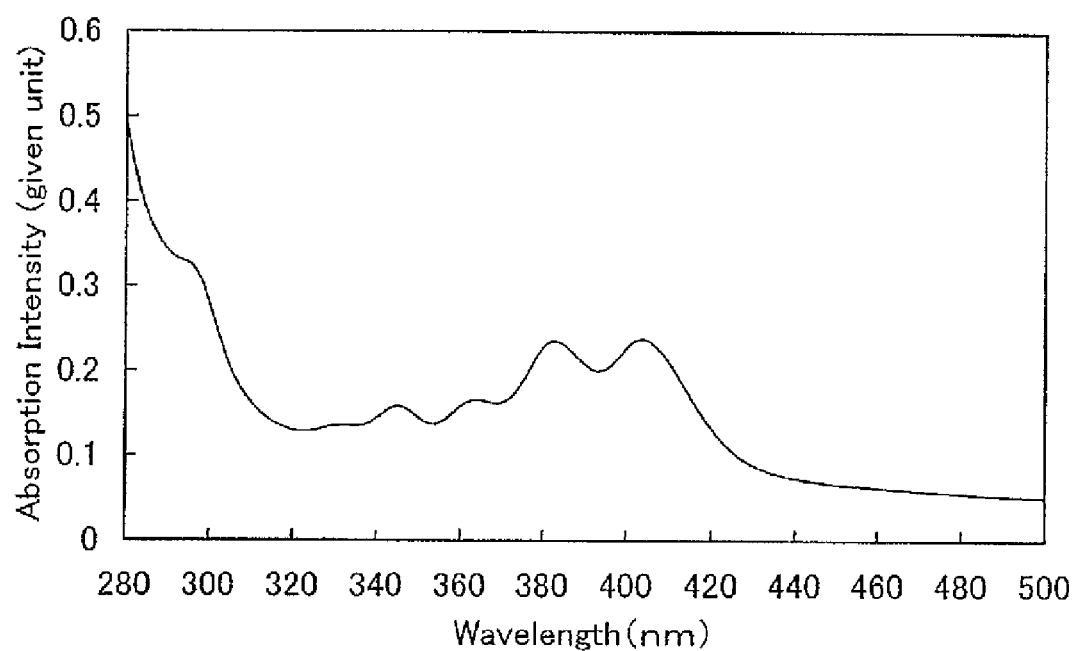
FIG. 17 is a graph showing an absorption spectrum of a thin film of 9-(biphenyl-4-yl)-10-[4-(carbazol-9-yl)phenyl]anthracene.
Figure 18:
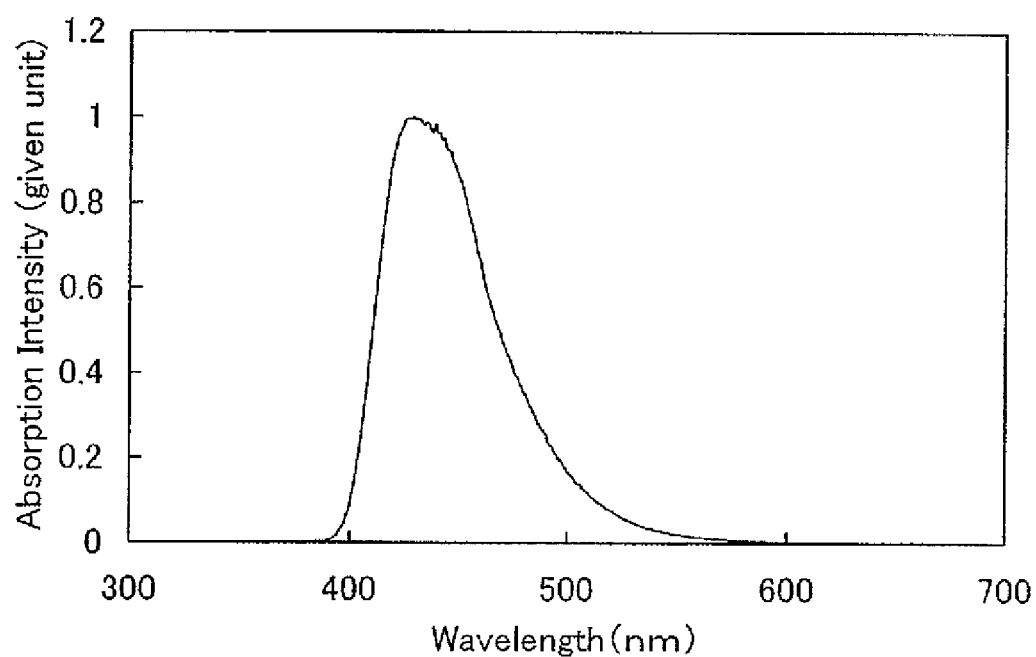
FIG. 18 is a graph showing an emission spectrum of a toluene solution of 9-(biphenyl-4-yl)-10-[4-(carbazol-9-yl)phenyl]anthracene.
Figure 19:
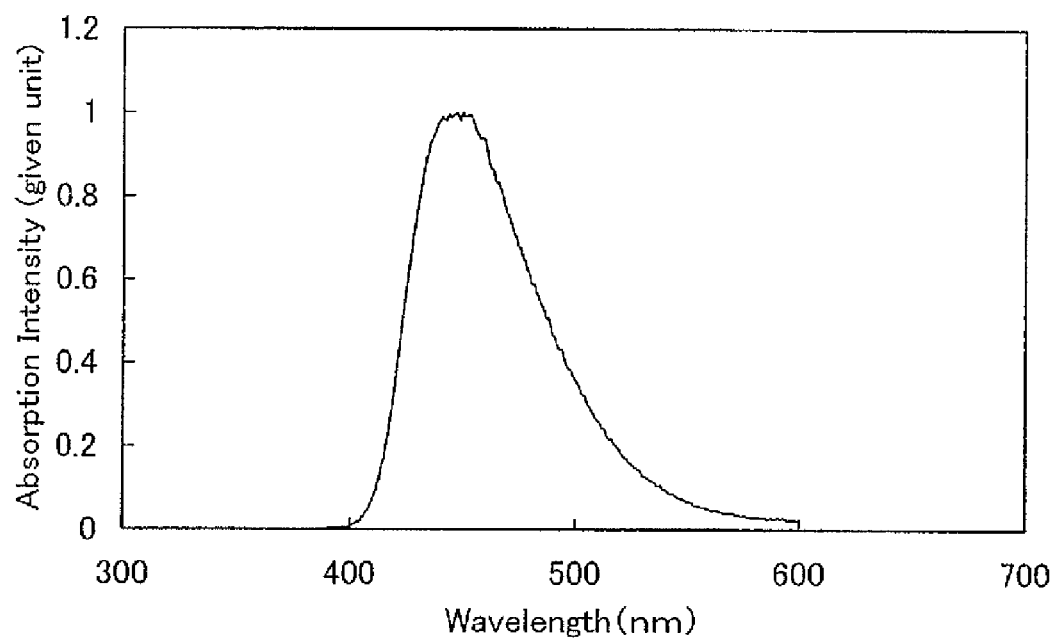
FIG. 19 is a graph showing an emission spectrum of a thin film of 9-(biphenyl-4-yl)-10-[4-(carbazol-9-yl)phenyl]anthracene.

FIG. 16 shows an absorption spectrum of a toluene solution of PPCzPA. FIG. 17 shows an absorption spectrum of a thin film of PPCzPA. The measurement was conducted by using a UV-visible spectrophotometer (V-550, manufactured by JASCO Corporation). The solution was put in a quartz cell, and the thin film was evaporated on a quartz substrate to form the samples. The absorption spectra thereof, from each of which the absorption spectrum of quartz was subtracted, are shown in FIGS. 16 and 17. In FIGS. 16 and 17, the horizontal axis indicates a wavelength (nm) while the vertical axis indicates absorption intensity (given unit). In the case of the toluene solution, absorption based on an anthracene skeleton was observed at around 376 nm and 398 nm, and in the case of the thin film, absorption based on an anthracene skeleton was observed at around 382 nm and 404 nm. The light emission spectrum of the toluene solution of PPCzPA (excitation wavelength: 370 nm) is shown in FIG. 18, while that of the thin film of PPCzPA (excitation wavelength: 380 nm) is shown in FIG. 19. In FIGS. 18 and 19, the horizontal axis indicates s a wavelength (nm) and the vertical axis indicates light emission intensity (given unit). The maximum light emission wavelength was 429 nm in the case of the toluene solution (excitation wavelength: 370 nm), and 450 nm in the case of the thin film (excitation wavelength: 380 nm).

In addition, the HOMO level of PPCzPA in the thin film state was −5.59 eV, which was measured by a photoelectron spectrometer (AC-2, manufactured by Riken Keiki Co., Ltd.) in the air. Moreover, the absorption edge was obtained from Tauc plot using data on the absorption spectrum of the thin film of PPCzPA in FIG. 17. When the absorption edge was estimated as an optical energy gap, the energy gap was 2.92 eV. Therefore, the LUMO level was −2.67 eV.

Moreover, the oxidation-reduction reaction characteristic of PPCzPA was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Aldrich, 99.8%, catalog number: 22705-6) was used as a solvent. Tetra-n-butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode. It is to be noted that the measurement was conducted at the room temperature.

The reduction reaction characteristic of PPCzPA was measured as follows. A scan for changing the potential of the work electrode with respect to the reference electrode from −2.50 V to −0.47 V after changing the potential from −0.47 V to −2.50 V was set as one cycle, and 100 cycles were measured. Further, the oxidation reaction characteristic of PPCzPA was measured as follows. A scan for changing the potential of the work electrode with respect to the reference electrode from 1.30 V to −0.33 V after changing the potential from −0.33 V to 1.30 V was set as one cycle, and 100 cycles were measured. Further, the scanning speed of the CV measurement was set to be 0.1 V/s.

Figure 58:
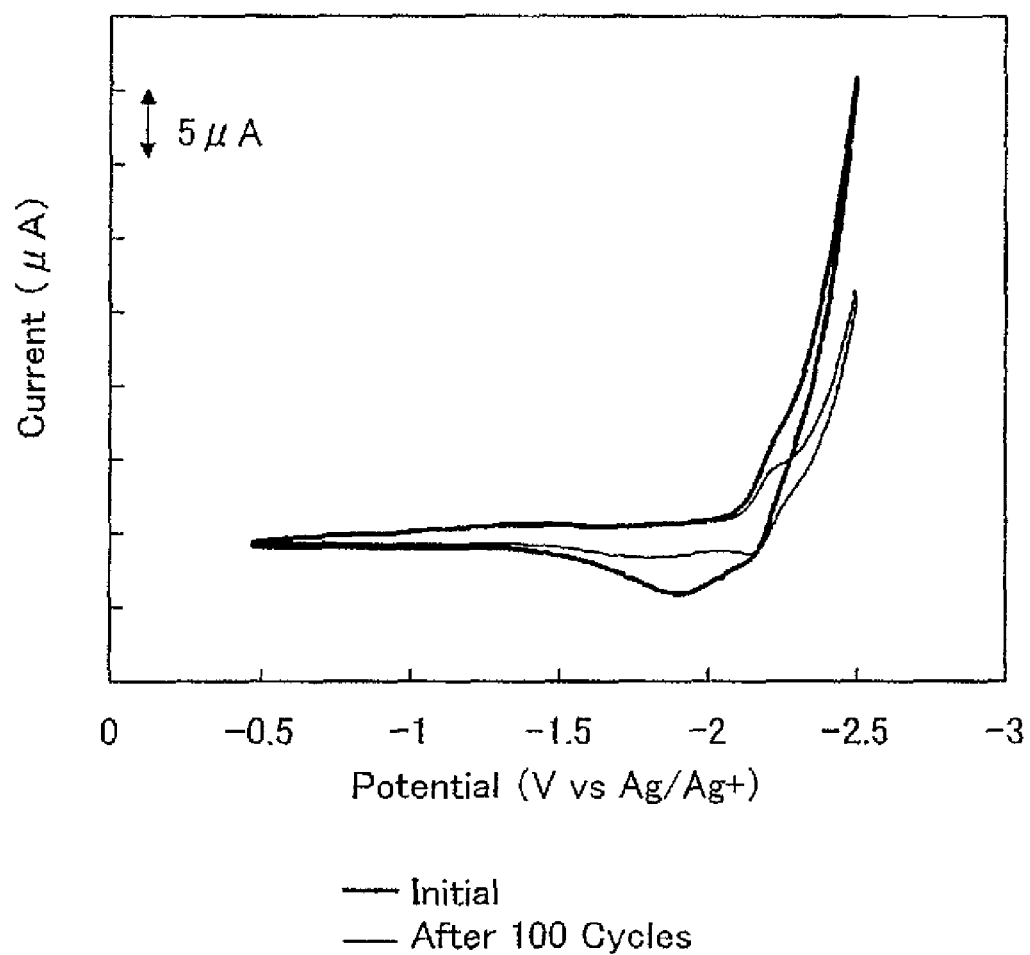
FIG. 58 is a graph showing a CV measurement result of a reduction side of 9-(biphenyl-4-yl)-10-[4-(carbazol-9-yl)phenyl]anthracene.
Figure 59:
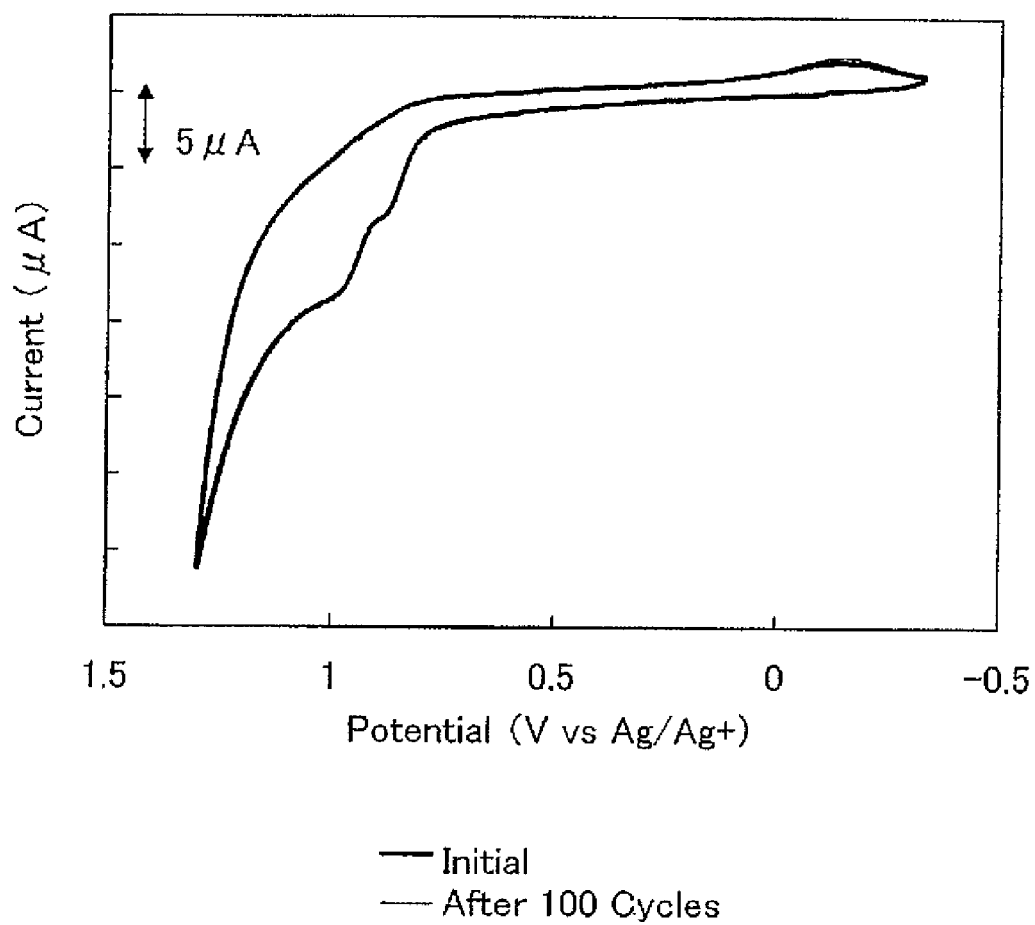
FIG. 59 is a graph showing a CV measurement result of an oxidation side of 9-(biphenyl-4-yl)-10-[4-(carbazol-9-yl)phenyl]anthracene.

FIG. 58 shows a result of the CV measurement on the reduction side of PPCzPA, and FIG. 59 shows a result of the CV measurement on the oxidation side of PPCzPA. In FIG. 58 and FIG. 59, the horizontal axis shows the potential (V) of the work electrode with respect to the reference electrode, while the vertical axis shows a value (μA) of current flowing between the work electrode and the auxiliary electrode.

From FIG. 58 and FIG. 59, in the case of PPCzPA, reversible peaks are shown on the oxide side and the reduction side. In addition, even when 100 cycles of oxidation to reduction or reduction to oxidation are repeated, peak intensity is hardly changed. From the above, it was found that the anthracene derivative of the present invention is extremely stable to the repetition of oxidation-reduction reaction.

Embodiment 3

In this embodiment, a synthesis method of 9-(4-tert-butylphenyl)-10-[4-(carbazol-9-yl)]phenylanthracene (abbreviation: PTBCzPA) represented by a structural formula (20) will be described.

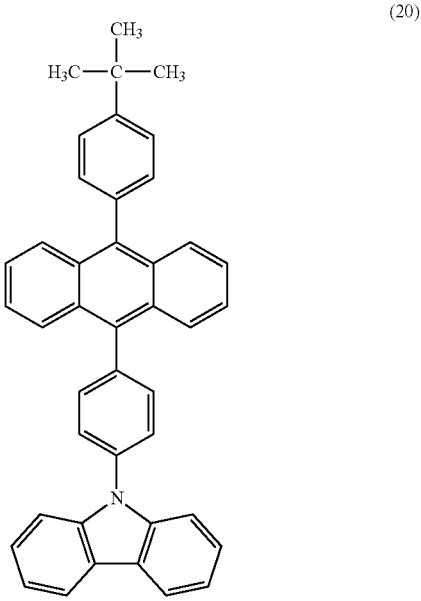

(20)

[Step 1] Synthesis of 9-bromo-10-(4-tert-butylphenyl)anthracene (i) Synthesis of 9-(4-tert-butylphenyl)anthracene A synthesis scheme of 9-(4-tert-butylphenyl)anthracene is shown in (D-1).

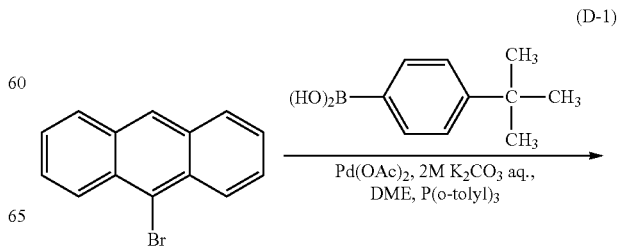

(D-1)

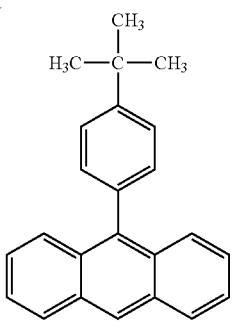

5.1 g (20 mmol) of 9-bromoanthracene, 3.6 g (20 mmol) of 4-tert-butylphenylboronic acid, and 244 mg (0.80 mmol) of tri(o-tolyl)phosphine were put into a 100-mL three-neck flask, and nitrogen substitution in the system was carried out. 20 mL of ethylene glycol dimethyl ether (DME) was added to this mixture, and the mixture was stirred under reduced pressure and degassed. After that, 45 mg (0.20 mmol) of palladium acetate(II) and 10 mL (2.0 mol/L) of a potassium carbonate solution were added. This reaction mixture was stirred at 80° C. for 3 hours under nitrogen gas stream. Then, the reaction mixture was cooled to the room temperature, and a solid that was precipitated was collected by suction filtration. The collected solid was dissolved in toluene, and the solution was subjected to suction filtration through Florisil, celite, and then alumina. The filtrate was condensed to obtain a solid, and the solid was recrystallized with ethanol, whereby 5.0 g of a white powdery solid, which was a target matter, was obtained with the yield of 81%.

(ii) Synthesis of 9-bromo-10-(4-tert-butylphenyl)anthracene

A synthesis scheme of 9-bromo-10-(4-tert-butylphenyl)anthracene is shown in (D-2).

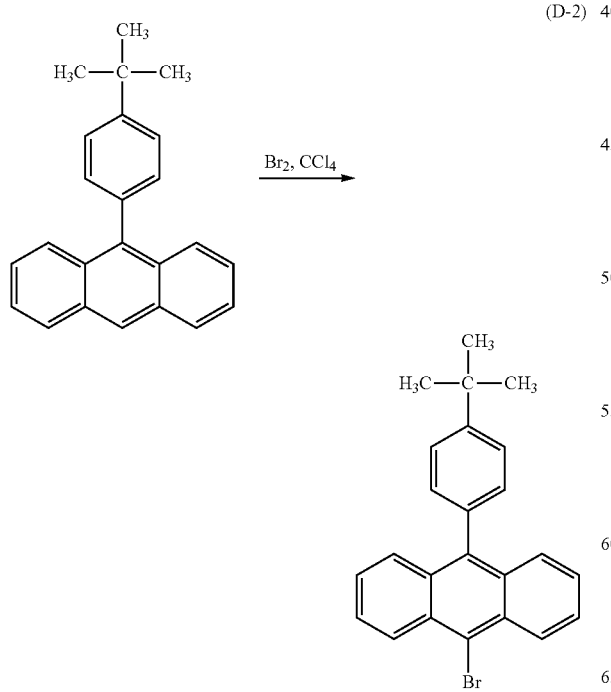

(D-2)

5.0 g (16.0 mmol) of 9-(4-tert-butylphenyl)anthracene and 90 mL of carbon tetrachloride were put into a 500-mL three-neck flask and were stirred. A solution in which 2.8 g (18 mmol) of bromine was dissolved in 10 mL of carbon tetrachloride was dropped into the above solution through a dropping funnel. After that, the solution was stirred at the room temperature for 1 hour, and a sodium thiosulfate aqueous solution was added to the reaction solution to complete the reaction. A water layer of the reaction mixture was extracted by chloroform, and the extracted solution and an organic layer were together washed with a saturated sodium hydrogen carbonate solution and saturated saline. The organic layer was dried with magnesium sulfate, and the mixture was filtrated naturally to remove the magnesium sulfate. Then, the filtrate was condensed to obtain a solid. The obtained solid was recrystallized with ethanol, whereby 6.3 g of a yellow powdery solid, which was a target matter, was obtained with the yield of 99%.

[Step 2] Synthesis of 9-(4-tert-butylphenyl)-10-[4-(carbazol-9-yl)]phenylanthracene (abbreviation: PTBCzPA)

A synthesis scheme of PTBCzPA is shown in (D-3).

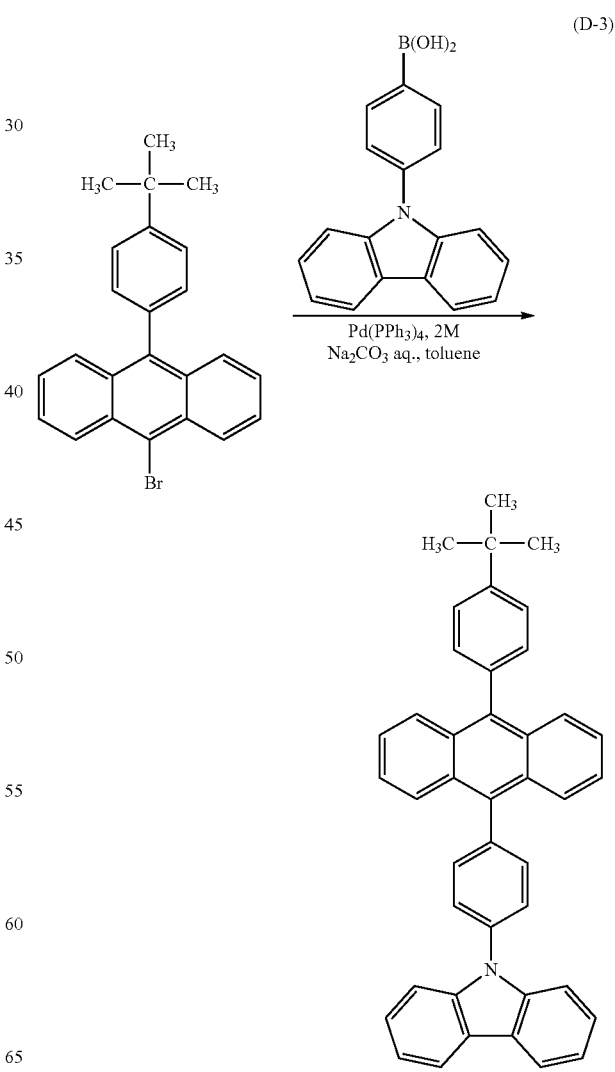

(D-3)

2.0 g (5.1 mmol) of 9-bromo-10-(4-tert-butylphenyl)anthracene and 1.5 g (5.1 mmol) of 4-(carbazol-9-yl)phenylboronic acid were put into a 100-mL three-neck flask, and nitrogen substitution in the system was carried out. 25 mL of ethylene glycol dimethyl ether (DME) and 10 mL (2.0 mol/L) of a potassium carbonate solution were added to this mixture, and the mixture was stirred under reduced pressure and degassed. After that, 85 mg (0.017 mmol) of tetrakis(triphenylphosphine)palladium(0) was added. This reaction mixture was stirred at 80° C. for 12 hours under nitrogen gas stream. Then, the reaction mixture was cooled to the room temperature, and a solid that was precipitated was collected by suction filtration. The collected solid was dissolved in toluene, and the solution was subjected to suction filtration through Florisil, celite, and then alumina. The filtrate was condensed to obtain a solid, and the solid was purified by silica gel column chromatography (hexane:toluene=7:3). The resulting solid was recrystallized with hexane, whereby 912 mg of a light yellow powdery solid, which was a target matter, was obtained with the yield of 32%. By a nuclear magnetic resonance measurement (NMR), it was confirmed that this compound was 9-(4-tert-butylphenyl)-10-[4-(carbazol-9-yl)]phenylanthracene (abbreviation: PTBCzPA).

Figure 20A:
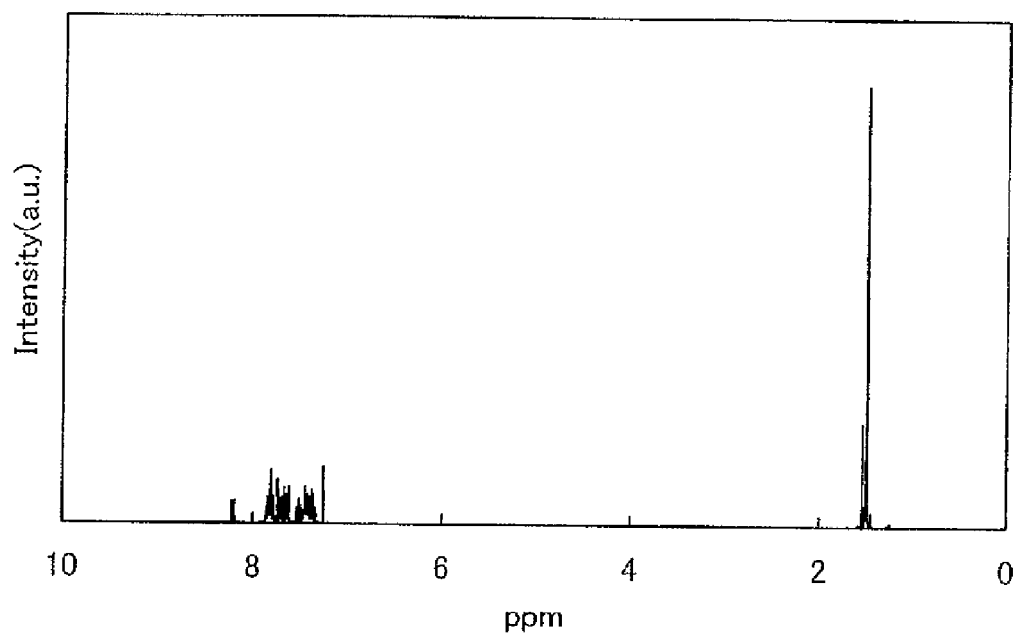
FIGS. 20A and 20B are graphs each showing $^1$H NMR of 9-(4-tert-butylphenyl)-10-[4-(carbazol-9-yl)]phenylanthracene.
Figure 20B:
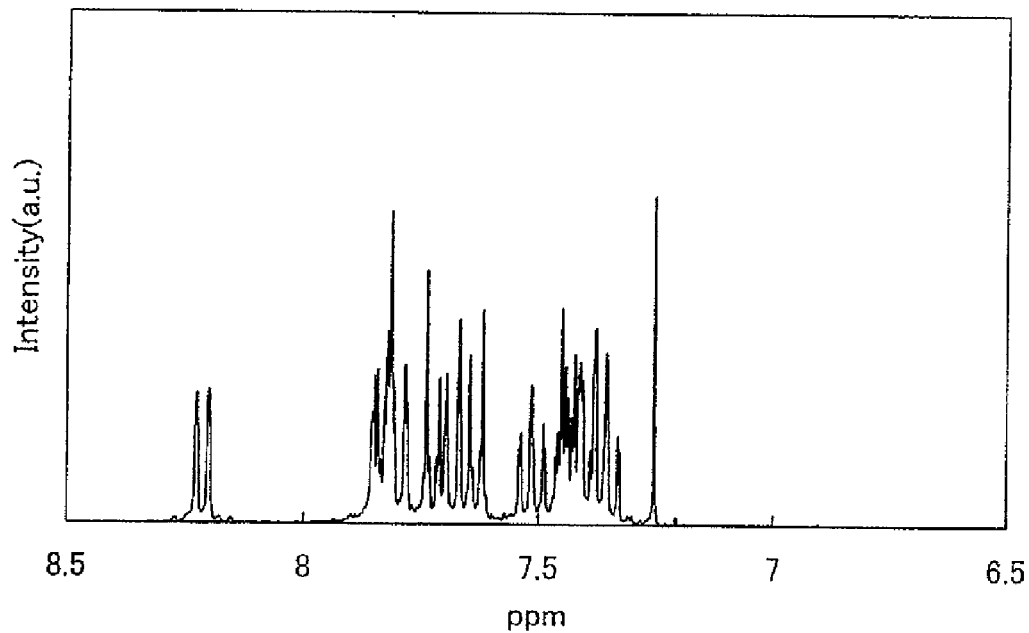

$^1$H NMR data of PTBCzPA is shown below. $^1$H NMR (300 MHz, CDCl$_3$); δ=1.50 (s, 9H), 7.33-7.54 (m, 10H), 7.62-7.85 (m, 12H), 8.21 (d, J=7.8 Hz, 2H). The $^1$H NMR chart is shown in FIGS. 20A and 20B. It is to be noted that the range of 6.5 ppm to 8.5 ppm in FIG. 20A, which is expanded, is shown in FIG. 20B.

When 901 mg of the obtained PTBCzPA by the above synthesis method was purified by sublimation for 12 hours under such condition that the flow of argon was 20.0 mL/min, the pressure was 200 Pa, and the heating temperature was 300° C., 839 mg of a light yellow needle crystal of PTBCzPA was obtained with the yield of 93%.

The thermogravimetry-differential thermal analysis (TG/DTA) of PTBCzPA was performed using a thermo-gravimetric/differential thermal analyzer (TG/DTA 320, product of Seiko Instruments Inc.). As a result, based on the relationship between gravity and temperature (thermogravimetric measurement), the temperature under normal pressure was 377° C. that is the temperature at which the gravity is 95% or less of the gravity at the starting point of the measurement. It was found that PTBCzPA had favorable heat resistance.

Figure 21:
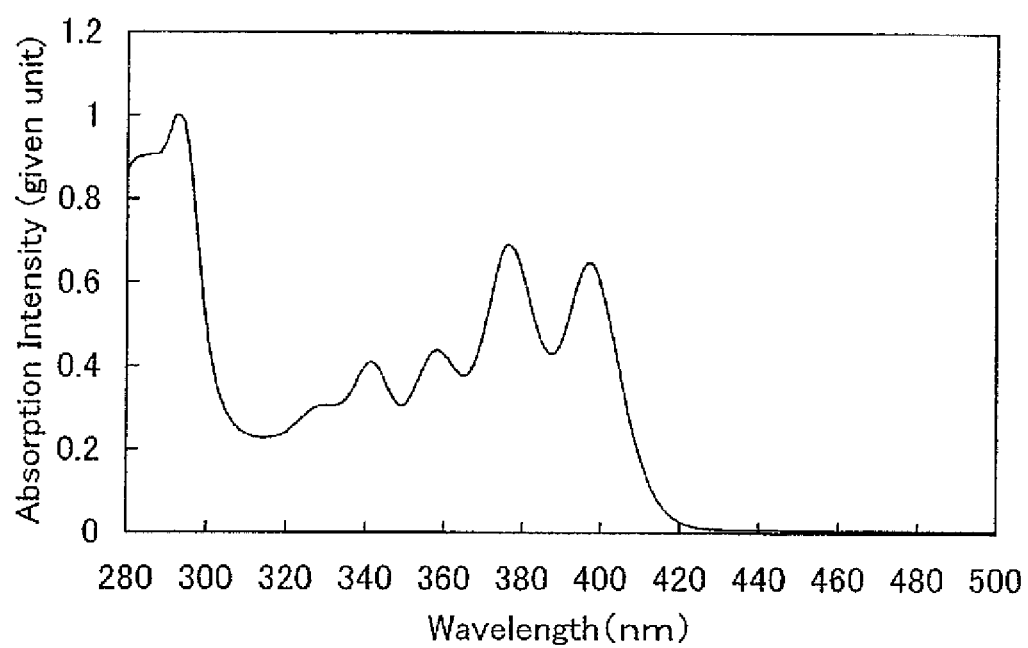
FIG. 21 is a graph showing an absorption spectrum of a toluene solution of 9-(4-tert-butylphenyl)-10-[4-(carbazol-9-yl)]phenylanthracene.
Figure 22:
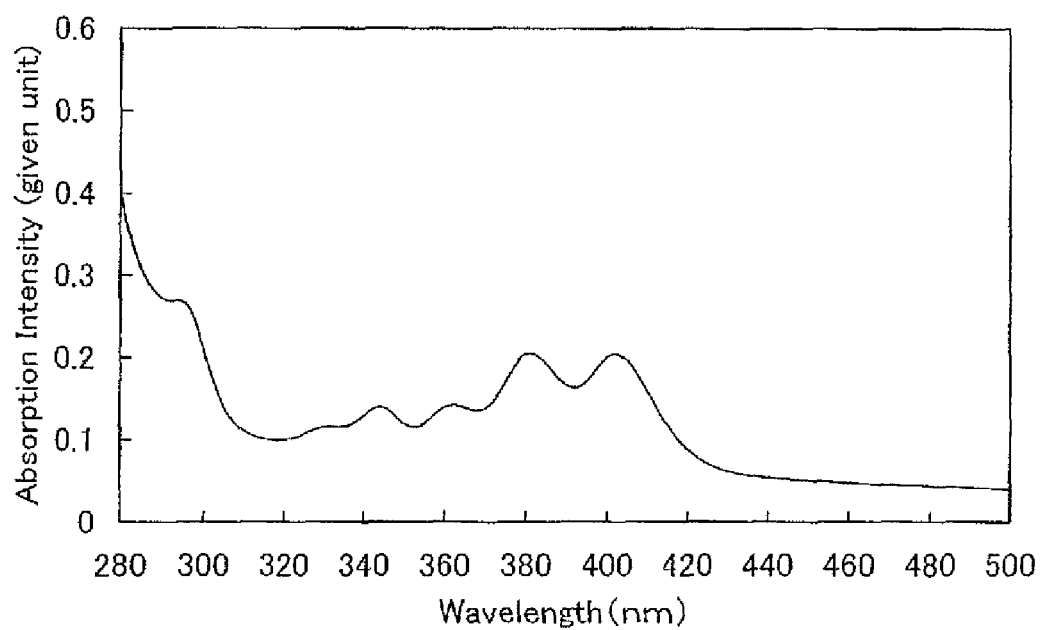
FIG. 22 is a graph showing an absorption spectrum of a thin film of 9-(4-tert-butylphenyl)-10-[4-(carbazol-9-yl)]phenylanthracene.
Figure 23:
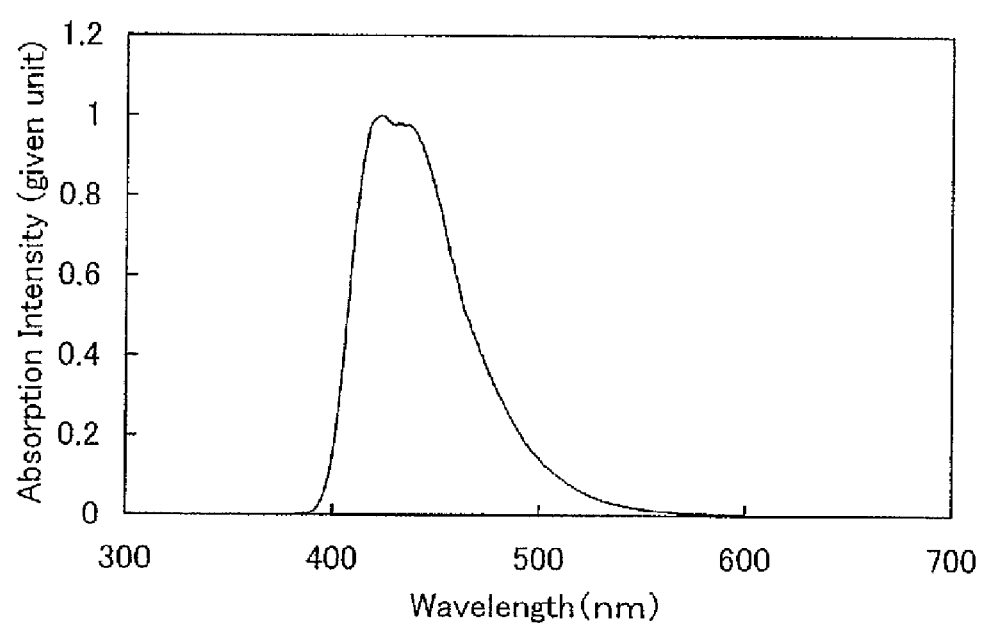
FIG. 23 is a graph showing an emission spectrum of a toluene solution of 9-(4-tert-butylphenyl)-10-[4-(carbazol-9-yl)]phenylanthracene.
Figure 24:
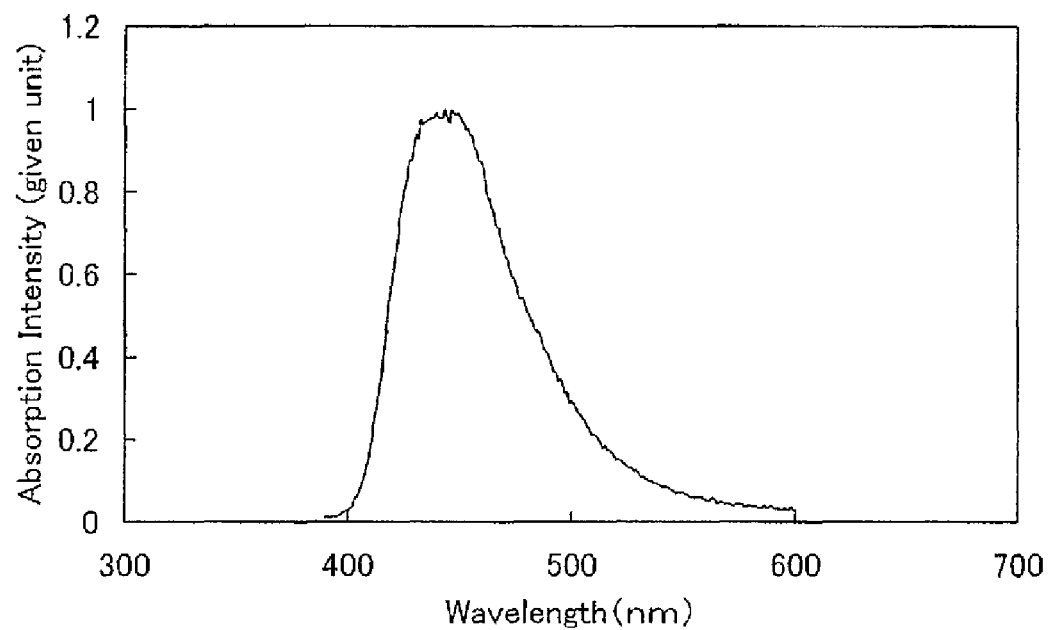
FIG. 24 is a graph showing an emission spectrum of a thin film of 9-(4-tert-butylphenyl)-10-[4-(carbazol-9-yl)]phenylanthracene.

FIG. 21 shows an absorption spectrum of a toluene solution of PTBCzPA. FIG. 22 shows an absorption spectrum of a thin film of PTBCzPA. The measurement was conducted by using a UV-visible spectrophotometer (V-550, manufactured by JASCO Corporation). The solution was put in a quartz cell, and the thin film was evaporated on a quartz substrate to form the samples. The absorption spectra thereof, from each of which the absorption spectrum of quartz was subtracted, are shown in FIGS. 21 and 22. In FIGS. 21 and 22, the horizontal axis indicates a wavelength (nm) while the vertical axis indicates absorption intensity (given unit). In the case of the toluene solution, absorption based on an anthracene skeleton was observed at around 376 and 396 nm, and in the case of the thin film, absorption based on an anthracene skeleton was observed at around 380 nm and 402 nm. The light emission spectrum of the toluene solution of PTBCzPA (excitation wavelength: 370 nm) is shown in FIG. 23, while that of the thin film of PTBCzPA (excitation wavelength: 380 nm) is shown in FIG. 24. In FIGS. 23 and 24, the horizontal axis indicates a wavelength (nm) and the vertical axis indicates light emission intensity (given unit). The maximum light emission wavelength was 423 nm in the case of the toluene solution (excitation wavelength: 370 nm), and 443 nm in the case of the thin film (excitation wavelength: 380 nm).

In addition, the HOMO level of PTBCzPA in the thin film state was −5.72 eV, which was measured by a photoelectron spectrometer (AC-2, manufactured by Riken Keiki Co., Ltd.) in the air. Moreover, the absorption edge was obtained from Tauc plot using data on the absorption spectrum of the thin film of PTBCzPA in FIG. 22. When the absorption edge was estimated as an optical energy gap, the energy gap was 2.95 eV. Therefore, the LUMO level was −2.77 eV.

Moreover, the oxidation-reduction reaction characteristic of PTBCzPA was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Aldrich, 99.8%, catalog number: 22705-6) was used as a solvent. Tetra-n-butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode. It is to be noted that the measurement was conducted at the room temperature.

The reduction reaction characteristic of PTBCzPA was measured as follows. A scan for changing the potential of the work electrode with respect to the reference electrode from −2.40 V to −0.25 V after changing the potential from −0.25 V to −2.40 V was set as one cycle, and 100 cycles were measured. Further, the oxidation reaction characteristic of PTBCzPA was measured as follows. A scan for changing the potential of the work electrode with respect to the reference electrode from 1.30 V to −0.33 V after changing the potential from −0.33 V to 1.30 V was set as one cycle, and 100 cycles were measured. Further, the scanning speed of the CV measurement was set to be 0.1 V/s.

Figure 60:
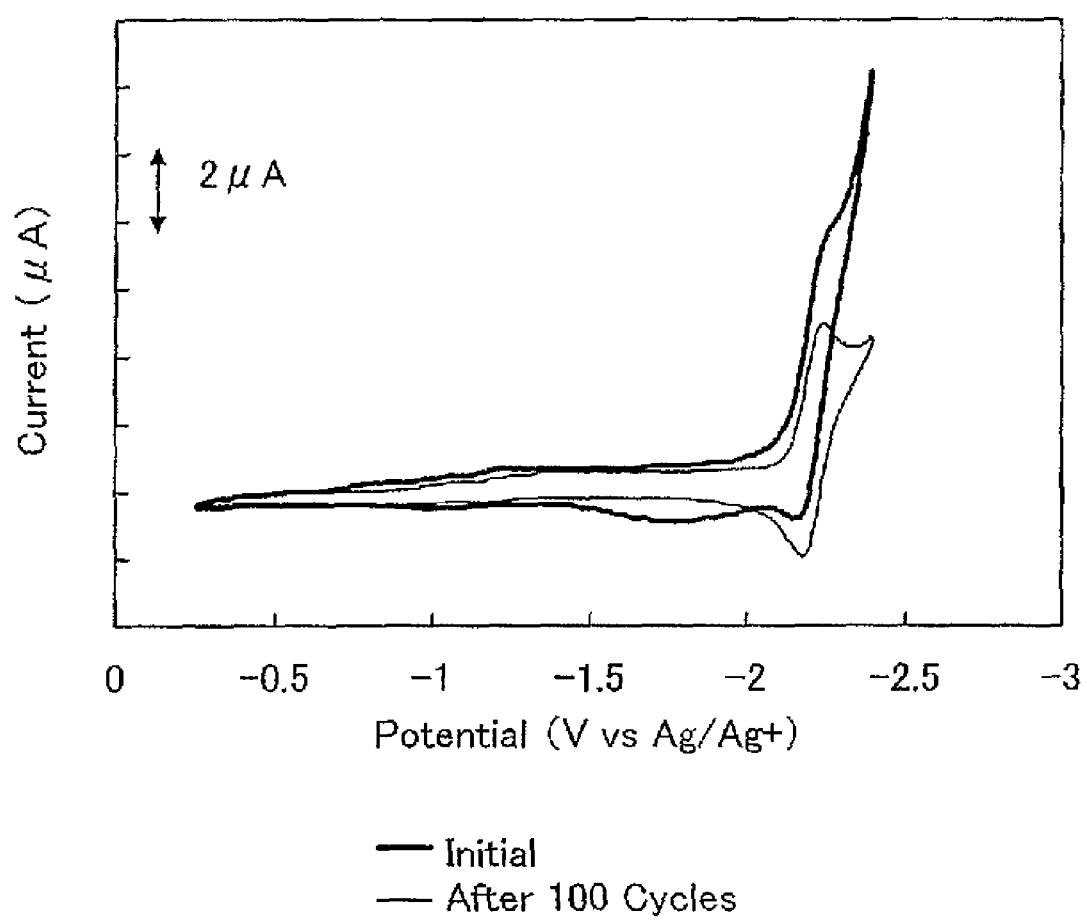
FIG. 60 is a graph showing a CV measurement result of a reduction side of 9-(4-tert-butylphenyl)-10-[4-(carbazol-9-yl)]phenylanthracene.
Figure 61:
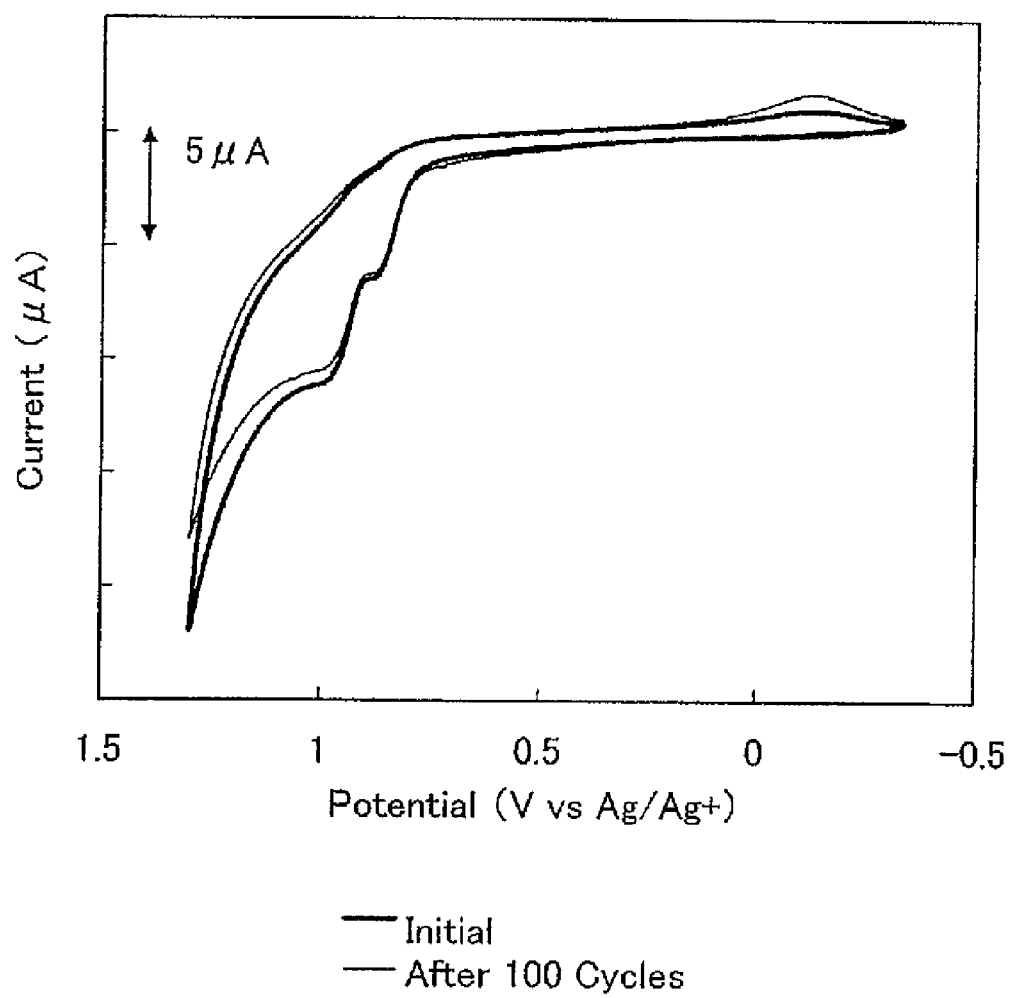
FIG. 61 is a graph showing a CV measurement result of an oxidation side of 9-(4-tert-butylphenyl)-10-[4-(carbazol-9-yl)]phenylanthracene.

FIG. 60 shows a result of the CV measurement on the reduction side of PTBCzPA, and FIG. 61 shows a result of the CV measurement on the oxidation side of PTBCzPA. In FIG. 60 and FIG. 61, the horizontal axis indicates the potential (V) of the work electrode with respect to the reference electrode, while the vertical axis indicates a value (μA) of current flowing between the work electrode and the auxiliary electrode.

From FIG. 60 and FIG. 61, in the case of PTBCzPA, reversible peaks are shown on the oxide side and the reduction side. In addition, even when 100 cycles of oxidation to reduction or reduction to oxidation were repeated, peak intensity is hardly changed. From the above, it is found that the anthracene derivative of the present invention is extremely stable to the repetition of oxidation-reduction reaction.

Embodiment 4

In this embodiment, a synthesis method of 9-[4-(carbazol-9-yl)phenyl]-10-(4-trifluoromethylphenyl)anthracene (CF3CzPA) represented by a structural formula (42) will be described.

(43)

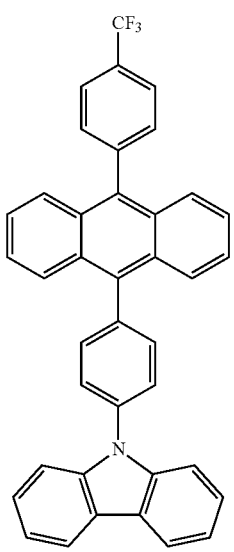

[Step 1] Synthesis of
9-bromo-10-(4-trifluoromethylphenyl)anthracene (i) Synthesis of 4-trifluoromethylphenylboronic acid A synthesis scheme of 4-trifluoromethylphenylboronic acid is shown in (E-1).

(E-4)

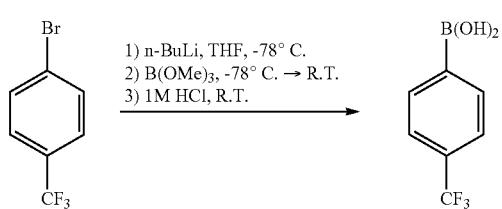

33 g (0.15 mol) of 4-bromotrifluoromethylbenzen was put into a 500-mL three-neck flask, and nitrogen substitution in the system was carried out. Then, 200 mL of tetrahydrofuran (THF) was added thereto, and the mixture was stirred. This mixture solution was stirred at −78° C., and 100 mL (0.16 mol) of n-butyllithium (1.6 mol/L) was dropped into the solution through a dropping funnel. After that, the obtained solution was stirred at the same temperature for 1 hour, and 22.3 mL (0.20 mol) of trimethyl borate was added to be stirred for about 12 hours while the reaction temperature was allowed to gradually increase to the room temperature. Then, 100 mL of dilute hydrochloric acid (1 mol/L) was added to the reaction solution, and the solution was stirred for 1 hour. A water layer of the mixture was extracted using ethyl acetate three times, the extracted solution and an organic layer were washed together one time using saturated saline, and the organic layer was dried with magnesium sulfate. The mixture was filtrated naturally to remove magnesium sulfate, and the filtrate was condensed to obtain a solid. The solid was washed with chloroform, whereby 15 g of a white solid, which was a target matter, was obtained with the yield of 54%.

(ii) Synthesis of
9-(4-trifluoromethylphenyl)anthracene

A synthesis scheme of 9-(4-trifluoromethylphenyl)anthracene is shown in (E-2).

(E-2)

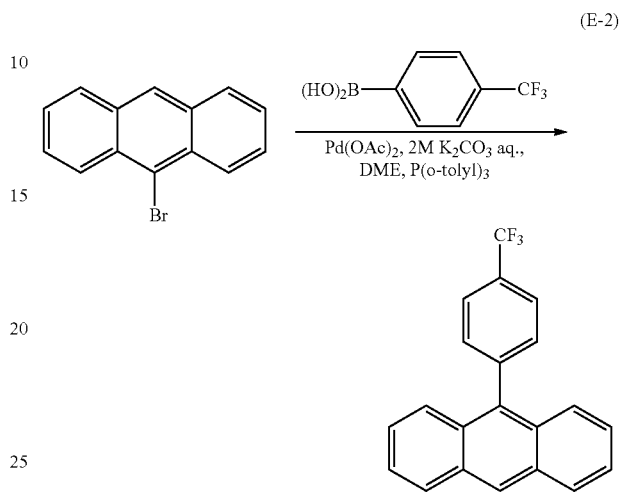

5.1 g (20 mmol) of 9-bromoanthracene, 3.8 g (20 mmol) of 4-trifluoromethylphenylboronic acid, and 244 mg (0.8 mmol) of tri(o-tolyl)phosphine were put into a 100-mL three-neck flask, and nitrogen substitution in the system was carried out. 20 mL of ethylene glycol dimethyl ether (DME) was added to this mixture, and the mixture was stirred under reduced pressure and degassed. After that, 45 mg (0.20 mmol) of palladium acetate(II) and 10 mL (2.0 mol/L) of a potassium carbonate solution were added. This reaction mixture was stirred at 80° C. for 3 hours under nitrogen gas stream. Then, the reaction mixture was cooled to the room temperature, and a solid that was precipitated was collected by suction filtration. The collected solid was dissolved in toluene, and the solution was subjected to suction filtration through Florisil, celite, and then alumina. The filtrate was condensed to obtain a solid, and the solid was recrystallized with ethanol, whereby 5.7 g of a white powdery solid, which was a target matter, was obtained with the yield of 88%.

(iii) Synthesis of
9-bromo-10-(4-trifluoromethylphenyl)anthracene

A synthesis scheme of 9-bromo-10-(4-trifluoromethylphenyl)anthracene is shown in (E-3).

(E-3)

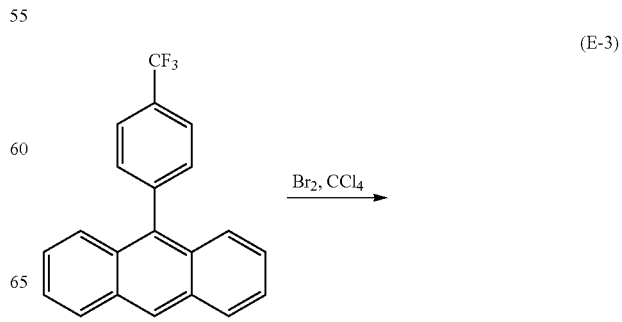

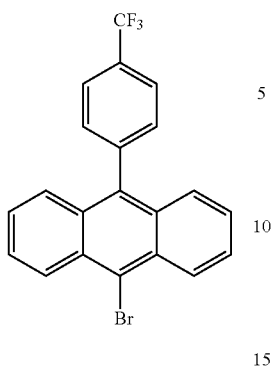

5.7 g (18 mmol) of 9-(4-trifluoromethylphenyl)anthracene and 90 mL of carbon tetrachloride were put into a 500-mL three-neck flask and stirred. A solution in which 3.2 g (20 mmol) of bromine was dissolved in 10 mL of carbon tetrachloride was dropped into the above solution through a dropping funnel. After that, the solution was stirred at the room temperature for 1 hour, and a sodium thiosulfate aqueous solution was added to the reaction solution to complete the reaction. A water layer of the reaction mixture was extracted by chloroform, and the extracted solution and an organic layer were together washed with a saturated sodium hydrogen carbonate solution and saturated saline. The organic layer was dried with magnesium sulfate, and the mixture was filtrated naturally to remove the magnesium sulfate. Then, the filtrate was condensed to obtain a solid. The obtained solid was recrystallized with ethanol, whereby 5.9 g of a yellow powdery solid, which was a target matter, was obtained with the yield of 84%.

[Step 2] Synthesis of 9-[4-(carbazol-9-yl)phenyl]-10-(4-trifluoromethylphenyl)anthracene (abbreviation: CF3CzPA)

A synthesis scheme of CF3CzPA is shown in (E-4).

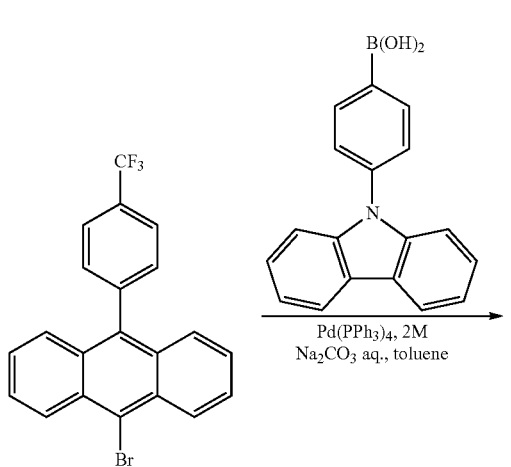
(E-4)

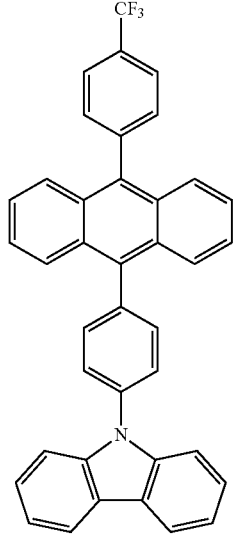

3.0 g (7.5 mmol) of 9-bromo-10-(4-trifluoromethylphenyl)anthracene, 2.2 g (7.5 mmol) of 4-(carbazol-9-yl)phenylboronic acid, and 200 mg (0.66 mmol) of tri(o-tolyl)phosphine were put into a 100-mL three-neck flask, and nitrogen substitution in the system was carried out. 25 mL of toluene and 10 mL (2.0 mol/L) of a potassium carbonate solution were added to this mixture, and the mixture was stirred under reduced pressure and degassed. After that, 60 mg (0.27 mmol) of palladium acetate(II) was added. This reaction mixture was stirred at 80° C. for 12 hours under nitrogen gas stream. Then, the reaction mixture was washed with water three times. A water layer of the mixture was extracted three times using ethyl acetate, the extracted solution and an organic layer were washed together using saturated saline, and the organic layer was dried with magnesium sulfate. The mixture was filtrated naturally to remove magnesium sulfate, and the filtrate was condensed to obtain a solid, and the obtain was purified by silica gel column chromatography (hexane:toluene=65:35). The resulting solid was recrystallized with hexane, whereby 1.6 g of a light yellow powdery solid, which was a target matter, was obtained with the yield of 38%. By a nuclear magnetic resonance measurement (NMR), it was confirmed that this compound was 9-[4-(carbazol-9-yl)phenyl]-10-(4-trifluoromethylphenyl)anthracene (abbreviation: CF3CzPA).

Figure 25A:
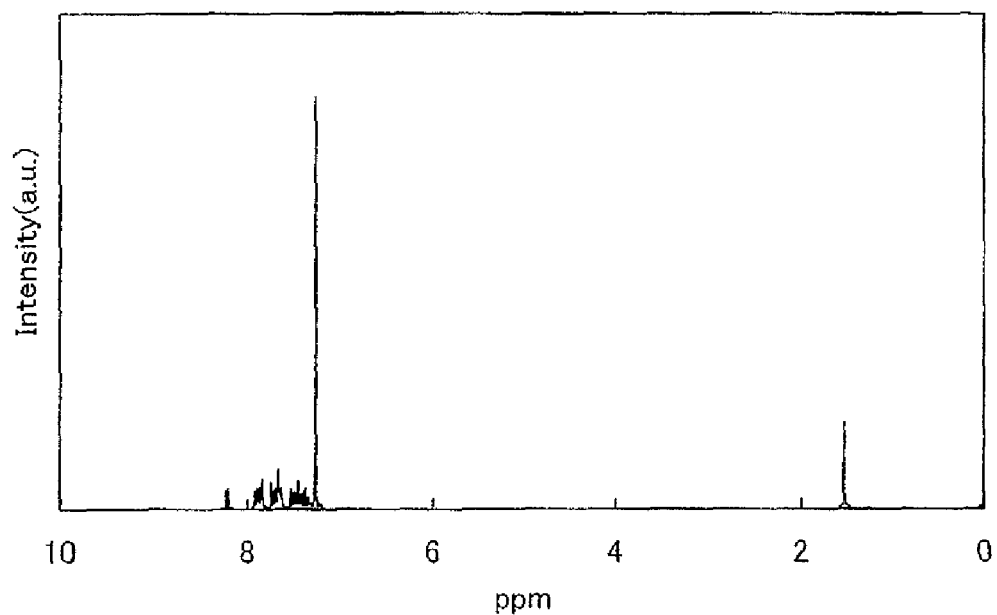
FIGS. 25A and 25B are graphs each showing $^1$H NMR of 9-[4-(carbazol-9-yl)phenyl]-10-(4-trifluoromethylphenyl)anthracene.
Figure 25B:
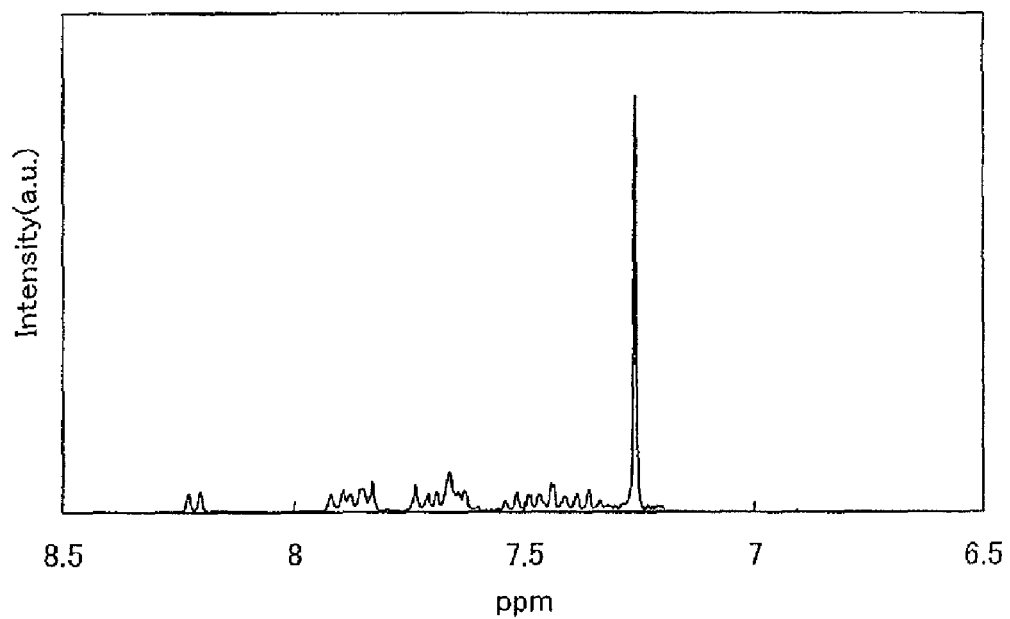

$^1$H NMR data of CF3CzPA is shown below. $^1$H NMR (300 MHz, CDCl$_3$); δ=7.33-7.54 (m, 8H), 7.60-7.74 (m, 8H), 7.83-7.92 (m, 6H), 8.22 (d, J=7.8 Hz, 2H). The $^1$H NMR chart is shown in FIGS. 25A and 25B. It is to be noted that the range of 6.5 ppm to 8.5 ppm in FIG. 25A, which is expanded, is shown in FIG. 25B.

When 1.5 g of the obtained CF3CzPA by the above synthesis method was purified for 12 hours by sublimation under such condition that the flow of argon was 20.0 mL/min, the pressure was 200 Pa, and the heating temperature was 300° C., 848 mg of a light yellow needle crystal of CF3CzPA was obtained with the yield of 56%.

The thermogravimetry-differential thermal analysis (TG/DTA) of CF3CzPA was performed using a thermo-gravimetric/differential thermal analyzer (TG/DTA 320, product of Seiko Instruments Inc.). As a result, based on the relationship between gravity and temperature (thermogravimetric measurement), the temperature under normal pressure was 328° C. that is the temperature at which the gravity is 95% or less of the gravity at the starting point of the measurement. It was found that had favorable heat resistance.

Figure 26:
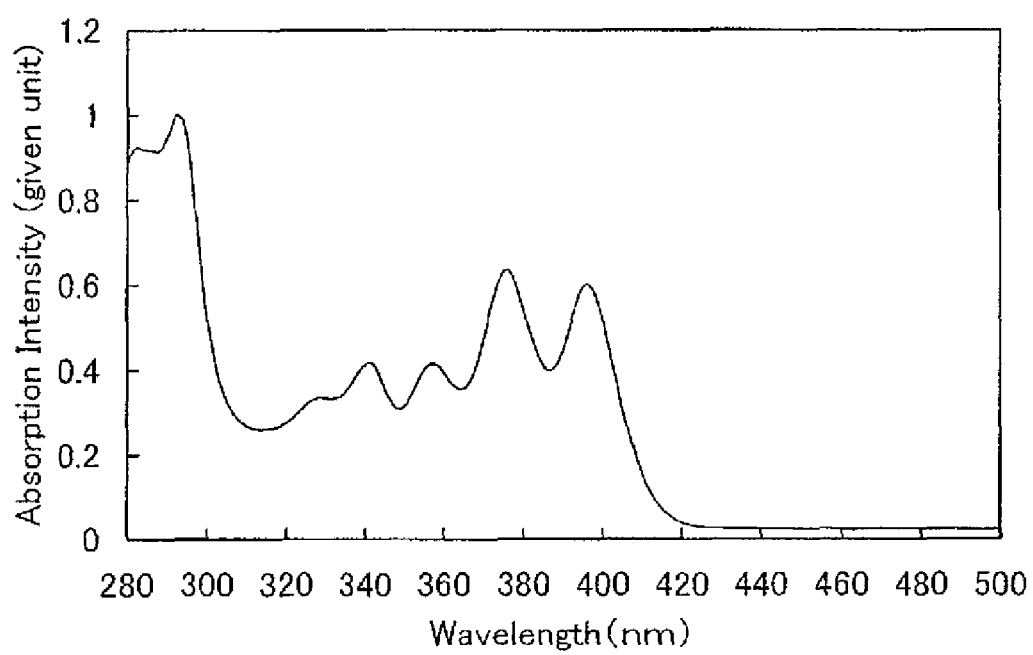
FIG. 26 is a graph showing an absorption spectrum of a toluene solution of 9-[4-(carbazol-9-yl)phenyl]-10-(4-trifluoromethylphenyl)anthracene.
Figure 27:
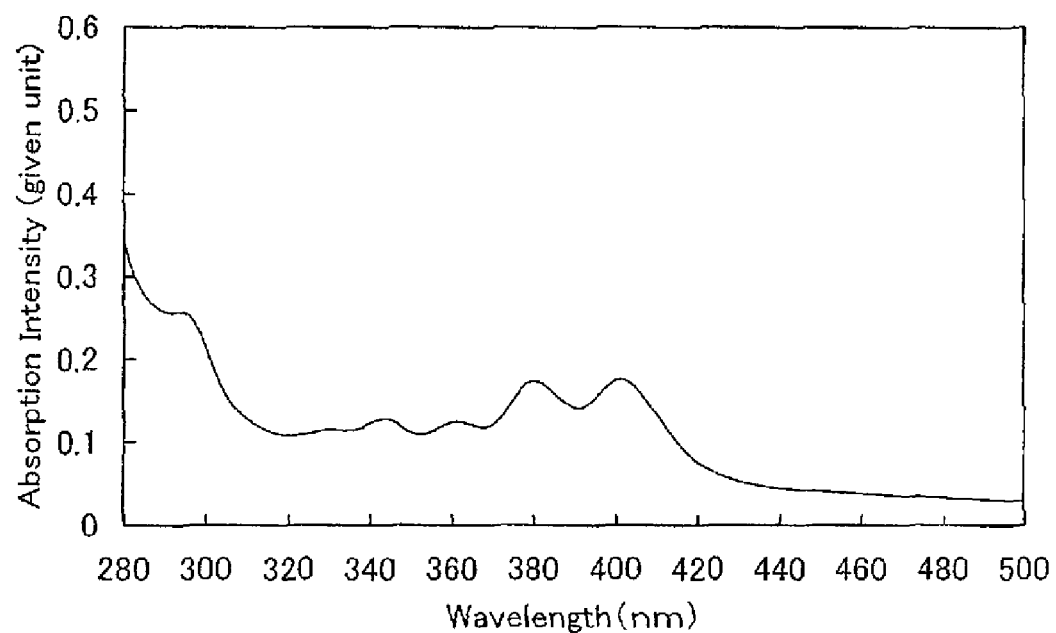
FIG. 27 is a graph showing an absorption of a thin film of 9-[4-(carbazol-9-yl)phenyl]-10-(4-trifluoromethylphenyl)anthracene.
Figure 28:
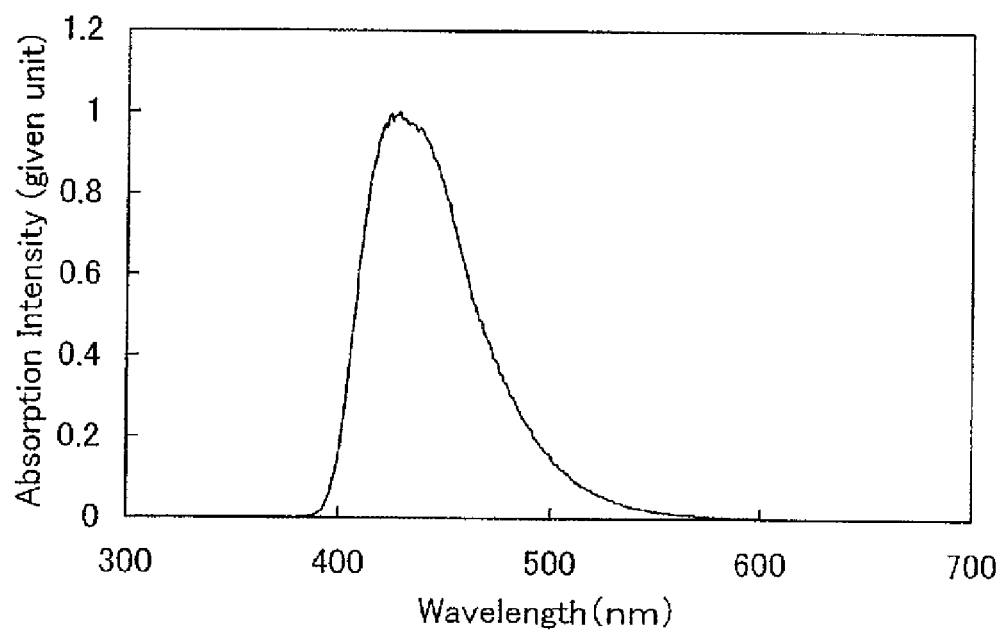
FIG. 28 is a graph showing an emission spectrum of a toluene solution of 9-[4-(carbazol-9-yl)phenyl]-10-(4-trifluoromethylphenyl)anthracene.
Figure 29:
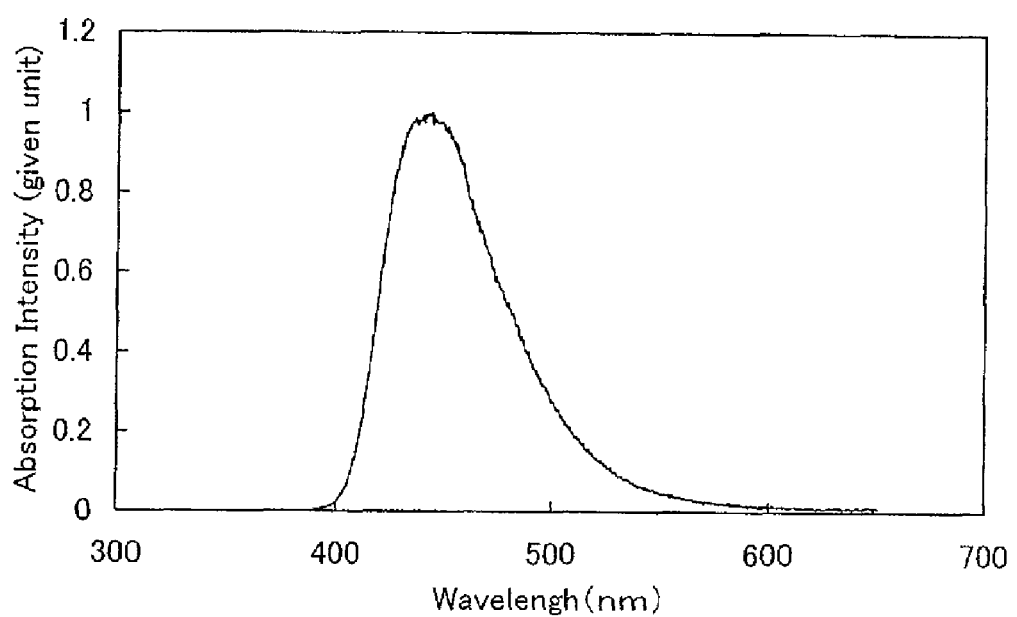
FIG. 29 is a graph showing an emission spectrum of a thin film of 9-[4-(carbazol-9-yl)phenyl]-10-(4-trifluoromethylphenyl)anthracene.

FIG. 26 shows an absorption spectrum of a toluene solution of CF3CzPA. FIG. 27 shows an absorption spectrum of a thin film of CF3CzPA. The measurement was conducted by using a UV-visible spectrophotometer (V-550, manufactured by JASCO Corporation). The solution was put in a quartz cell, and the thin film was evaporated on a quartz substrate to form the samples. The absorption spectra thereof, from each of which the absorption spectrum of quartz was subtracted, are shown in FIGS. 26 and 27. In FIGS. 26 and 27, the horizontal axis indicates a wavelength (nm) while the vertical axis indicates absorption intensity (given unit). In the case of the toluene solution, absorption based on an anthracene skeleton was observed at around 376 nm and 396 nm, and in the case of the thin film, absorption based on an anthracene skeleton was observed at around 380 nm and 402 nm. The light emission spectrum of the toluene solution of CF3CzPA (excitation wavelength: 370 nm) is shown in FIG. 28, while that of the thin film of CF3CzPA (excitation wavelength: 380 nm) is shown in FIG. 29. In FIGS. 28 and 29, the horizontal axis indicates a wavelength (nm) and the vertical axis indicates light emission intensity (given unit). The maximum light emission wavelength was 428 nm in the case of the toluene solution (excitation wavelength: 370 nm), and 444 nm in the case of the thin film (excitation wavelength: 380 nm).

In addition, the HOMO level of CF3CzPA in the thin film state was −6.01 eV, which was measured by a photoelectron spectrometer (AC-2, manufactured by Riken Keiki Co., Ltd.) in the air. Moreover, the absorption edge was obtained from Tauc plot using data on the absorption spectrum of the thin film of CF3CzPA in FIG. 27. When the absorption edge was estimated as an optical energy gap, the energy gap was 2.95 eV. Therefore, the LUMO level was −3.06 eV.

Moreover, the oxidation-reduction reaction characteristic of CF3CzPA was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Aldrich, 99.8%, catalog number: 22705-6) was used as a solvent. Tetra-n-butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode. It is to be noted that the measurement was conducted at the room temperature.

The reduction reaction characteristic of CF3CzPA was measured as follows. A scan for changing the potential of the work electrode with respect to the reference electrode from −2.23 V to −0.18V after changing the potential from −0.18 V to −2.23 V was set as one cycle, and 100 cycles were measured. Further, the oxidation reaction characteristic of CF3CzPA was measured as follows. A scan for changing the potential of the work electrode with respect to the reference electrode from 1.30 V to −0.27 V after changing the potential from −0.27 V to 1.30 V was set as one cycle, and 100 cycles were measured. Further, the scanning speed of the CV measurement was set to be 0.1 V/s.

Figure 62:
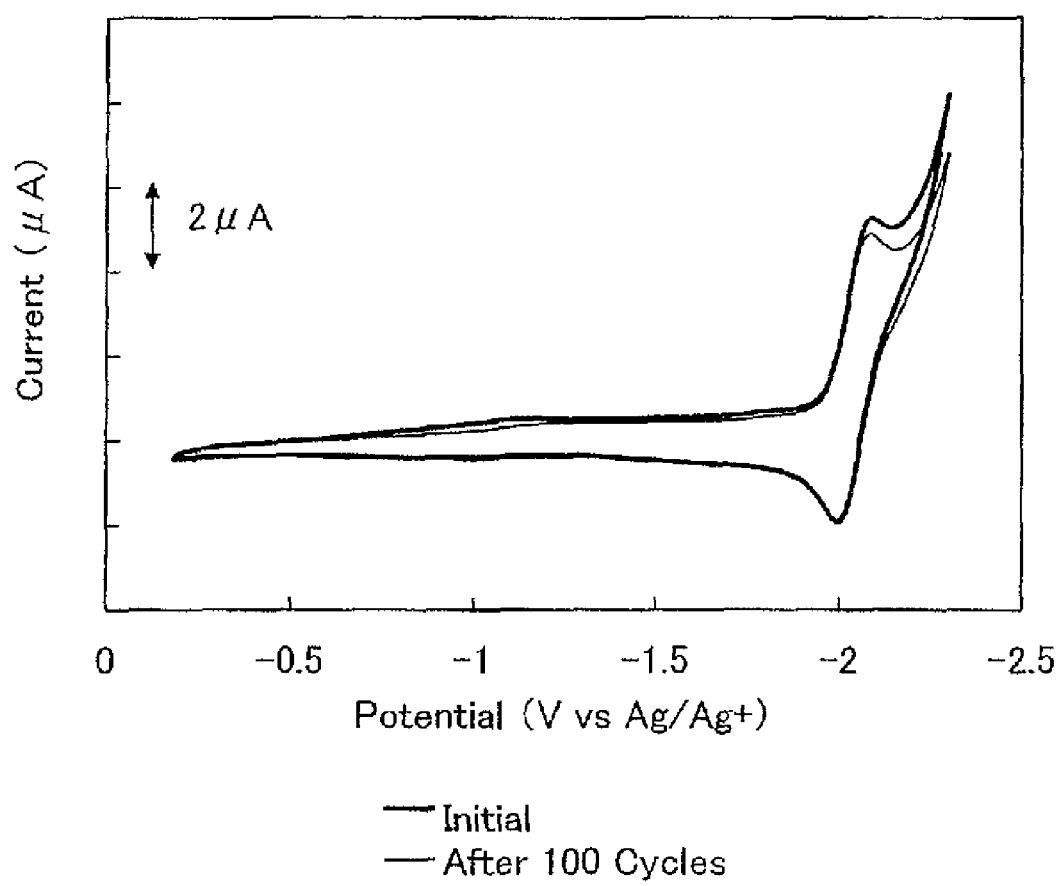
FIG. 62 is a graph showing a CV measurement result of a reduction side of 9-[4-(carbazol-9-yl)phenyl]-10-(4-trifluoromethylphenyl)anthracene.
Figure 63:
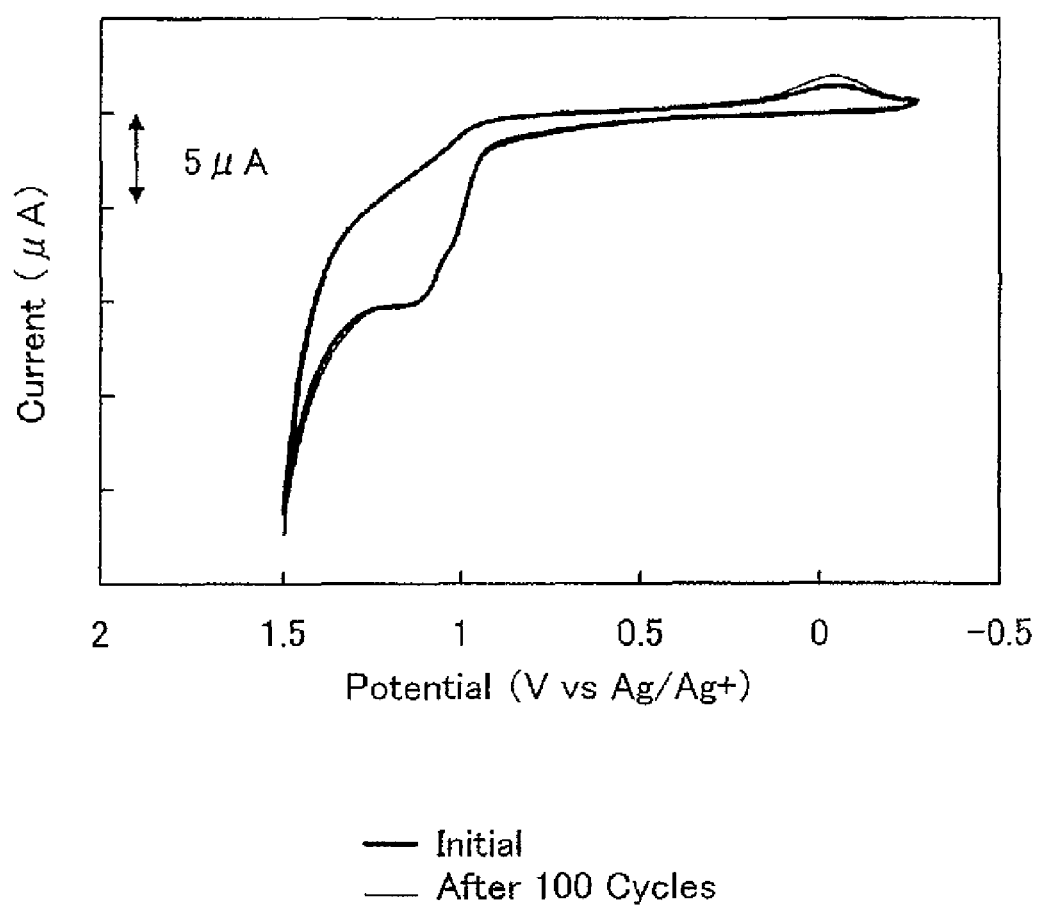
FIG. 63 is a graph showing a CV measurement result of an oxidation side of 9-[4-(carbazol-9-yl)phenyl]-10-(4-trifluoromethylphenyl)anthracene.

FIG. 62 shows a result of the CV measurement on the reduction side of CF3CzPA, and FIG. 63 shows a result of the CV measurement on the oxidation side of CF3CzPA. In FIG. 62 and FIG. 63, the horizontal axis indicates the potential (V) of the work electrode with respect to the reference electrode, while the vertical axis indicates a value (µA) of current flowing between the work electrode and the auxiliary electrode.

From FIG. 62 and FIG. 63, in the case of CF3CzPA, reversible peaks are shown on the oxide side and the reduction side. In addition, even when 100 cycles of oxidation to reduction or reduction to oxidation were repeated, peak intensity is hardly changed. From the above, it is found that the anthracene derivative of the present invention is extremely stable to the repetition of oxidation-reduction reaction.

Embodiment 5

In this embodiment, a synthesis method of 9-[4-(carbazol-9-yl)phenyl]-10-(2-naphthyl)anthracene (abbreviation: βNCzPA) represented by a structural formula (16) will be described.

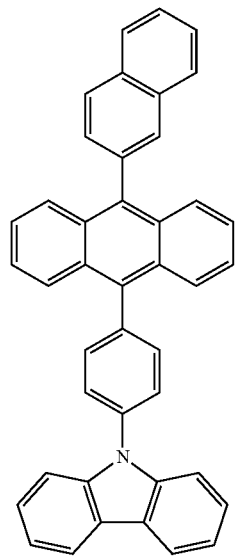

(16)

[Step 1] Synthesis of 9-bromo-10-(2-naphthyl)anthracene (i) Synthesis of 9-(2-naphthyl)anthracene A synthesis scheme of 9-(2-naphthyl)anthracene is shown in (F-1).

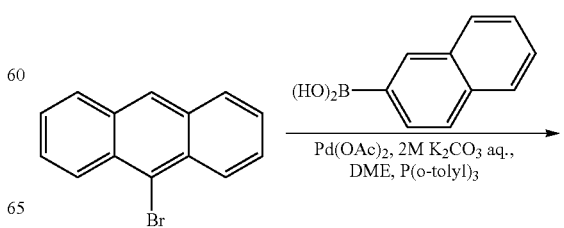

(F-1)

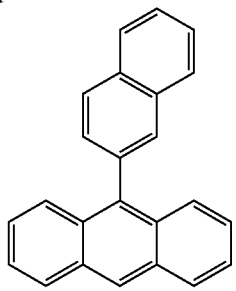

5.1 g (20 mmol) of 9-bromoanthracene, 3.4 g (20 mmol) of 2-naphthylboronic acid, and 244 mg (0.80 mmol) tri(ortho-tolyl)phosphine were put into a 100-mL three-neck flask, and nitrogen substitution in the system was carried out. 20 mL of ethylene glycol dimethyl ether (DME) was added to this mixture, and the mixture was stirred under reduced pressure and degassed. After that, 45 mg (0.20 mmol) of palladium acetate(II) and 10 mL (2.0 mol/L) of a potassium carbonate solution were added. This reaction mixture was stirred at 80° C. for 3 hours under nitrogen gas stream. Then, the reaction mixture was cooled to the room temperature, and a solid that was precipitated was collected by suction filtration. The collected solid was dissolved in toluene, and the solution was subjected to suction filtration through Florisil, celite, and then alumina. The filtrate was condensed to obtain a solid, and the solid was recrystallized with ethanol, whereby 5.6 g of a white powdery solid, which was a target matter, was obtained with the yield of 92%.

(ii) Synthesis of 9-bromo-10-(2-naphthyl)anthracene

A synthesis scheme of 9-bromo-10-(2-naphthyl)anthracene is shown in (F-2).

(F-2)

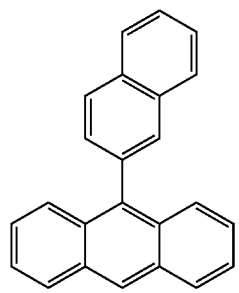

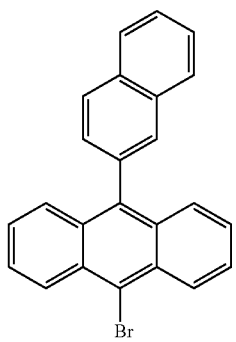

5.6 g (18.0 mmol) of 9-(2-naphthyl)anthracene and 90 mL of carbon tetrachloride were put into a 500-mL three-neck flask and stirred. A solution in which 3.2 g (20 mmol) of bromine was dissolved in 10 mL of carbon tetrachloride was dropped into the above solution through a dropping funnel. After that, the solution was stirred at the room temperature for 1 hour, and a sodium thiosulfate aqueous solution was added to the reaction solution to complete the reaction. A water layer of the reaction mixture was extracted by chloroform, and the extracted solution and an organic layer were together washed with a saturated sodium hydrogen carbonate solution and saturated saline. The organic layer was dried with magnesium sulfate, and the mixture was filtrated naturally to remove the magnesium sulfate. Then, the filtrate was condensed to obtain a solid. The obtained solid was recrystallized with ethanol, whereby 5.5 g of a yellow powdery solid, which was a target matter, was obtained with the yield of 79%.

[Step 2] Synthesis of 9-[4-(carbazol-9-yl)phenyl]-10-(2-naphthyl)anthracene (abbreviation: βNCzPA)

A synthesis scheme of βNCzPA is shown in (F-3).

(F-3)

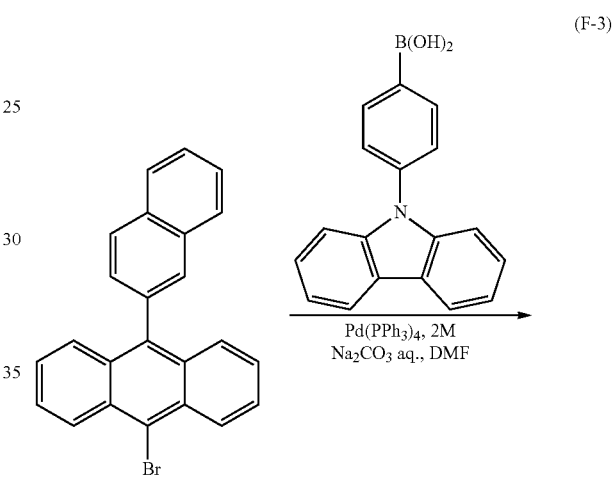

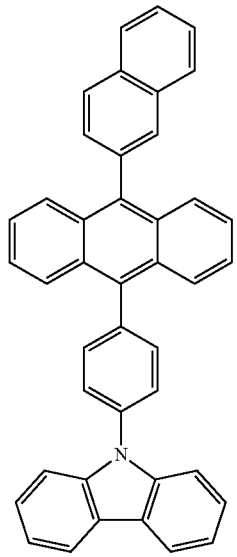

3.0 g (7.8 mmol) of 9-bromo-10-(2-napthyl)anthracene and 2.3 g (7.8 mmol) of 4-(carbazol-9-yl)phenylboronic acid were put into a 100-mL three-neck flask, and nitrogen substitution in the system was carried out. 25 mL of ethylene glycol dimethyl ether (DME) and 10 mL (2.0 mol/L) of a potassium carbonate solution were added to this mixture, and the mixture was stirred under reduced pressure and degassed. After that, 90 mg (0.017 mmol) of tetrakis(triphenylphosphine)palladium(0) was added. This reaction mixture was stirred at 80° C. for 12 hours under nitrogen gas stream. Then, the reaction mixture was washed with water. A water layer of the mixture was extracted using ethyl acetate, the extracted solution and an organic layer were washed together using saturated saline, and the organic layer was dried with magnesium sulfate. The mixture was filtrated naturally to remove magnesium sulfate. The filtrate was condensed to obtain a solid, and the solid was purified by silica gel column chromatography (hexane:toluene=7:3). The resulting solid was recrystallized with hexane, whereby 2.4 g of a light yellow solid, which was a target matter, was obtained with the yield of 57%. By a nuclear magnetic resonance measurement (NMR), it was confirmed that this compound was 9-[4-(carbazol-9-yl)phenyl]-10-(2-naphthyl)anthracene (abbreviation: βNCzPA).

Figure 30A:
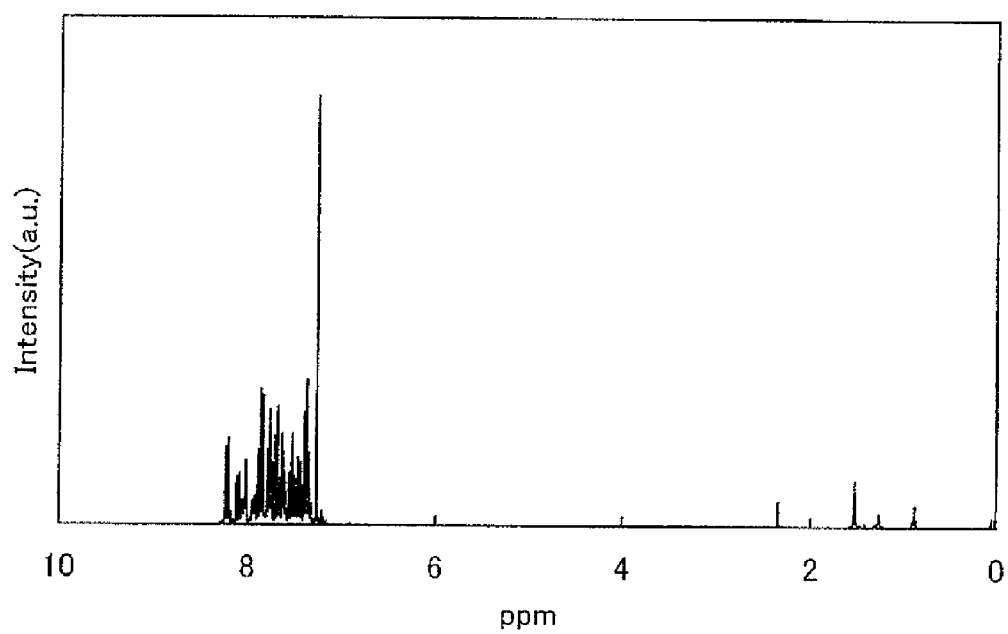
FIGS. 30A and 30B are graphs each showing $^1$H NMR of 9-[4-(carbazol-9-yl)phenyl]-10-(2-naphthyl)anthracene.
Figure 30B:
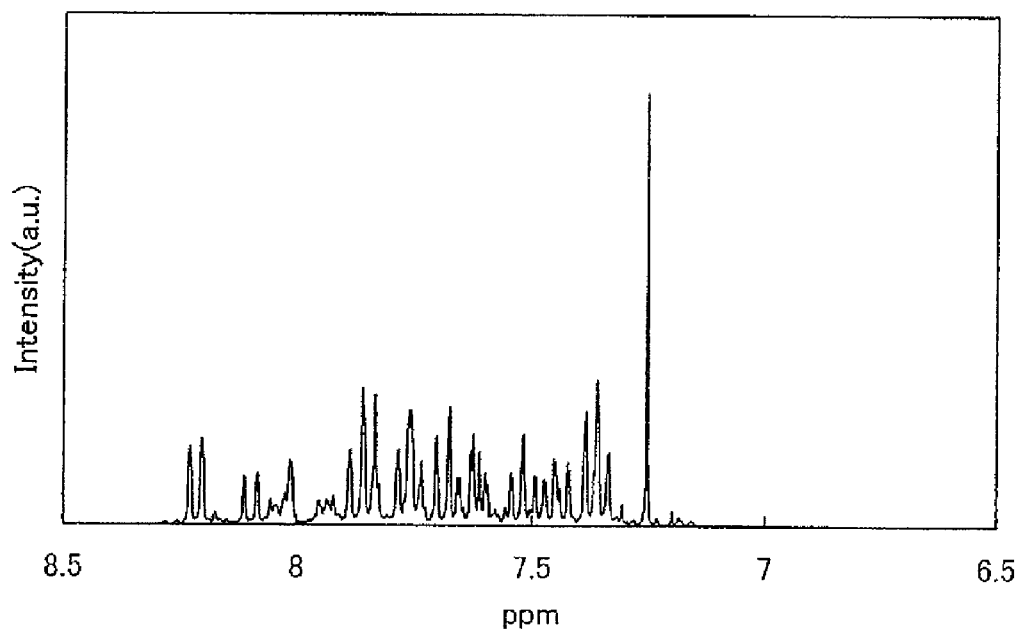

$^1$H NMR data of βNCzPA is shown below. 1H NMR (300 MHz, CDCl$_3$); δ=7.33-7.56 (m, 9H), 7.59-7.78 (m, 9H), 7.83-7.89 (m, 4H), 7.92-7.95 (m, 1H), 8.01-8.06 (m, 2H), 8.10 (d, J=8.7 Hz, 1H), 8.22 (d, J=7.2 Hz, 2H). The $^1$H NMR chart is shown in FIGS. 30A and 30B. It is to be noted that the range of 6.5 ppm to 8.5 ppm in FIG. 30A, which is expanded, is shown in FIG. 30B.

When 1.79 g of the obtained βNCzPA by the above synthesis method was purified by sublimation for 12 hours under such condition that the flow of argon was 3.0 ml/min, the pressure was 8.0 Pa, and the heating temperature was 290° C., 1.59 g of a light yellow needle crystal of βNCzPA was obtained with the yield of 89%.

The thermogravimetry-differential thermal analysis (TG/DTA) of βNCzPA was performed using a thermo-gravimetric/differential thermal analyzer (TG/DTA 320, product of Seiko Instruments Inc.). As a result, based on the relationship between gravity and temperature (thermogravimetric measurement), the temperature under normal pressure was 368° C. that is the temperature at which the gravity is 95% or less of the gravity at the starting point of the measurement. It was found that had favorable heat resistance.

Figure 31:
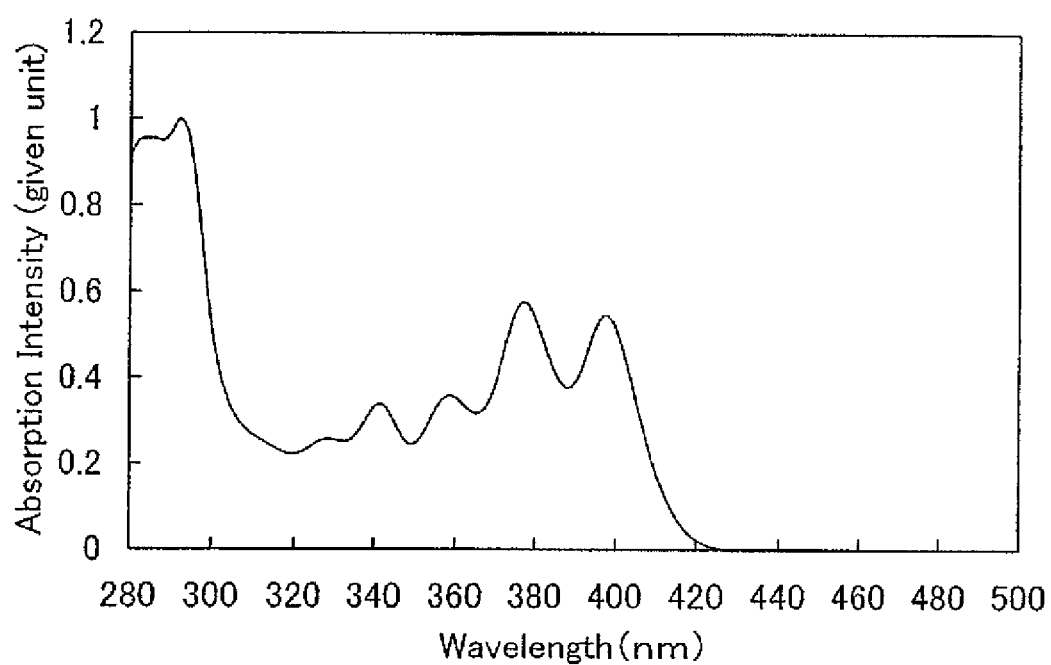
FIG. 31 is a graph showing an absorption spectrum of a toluene solution of 9-[4-(carbazol-9-yl)phenyl]-10-(2-naphthyl)anthracene.
Figure 32:
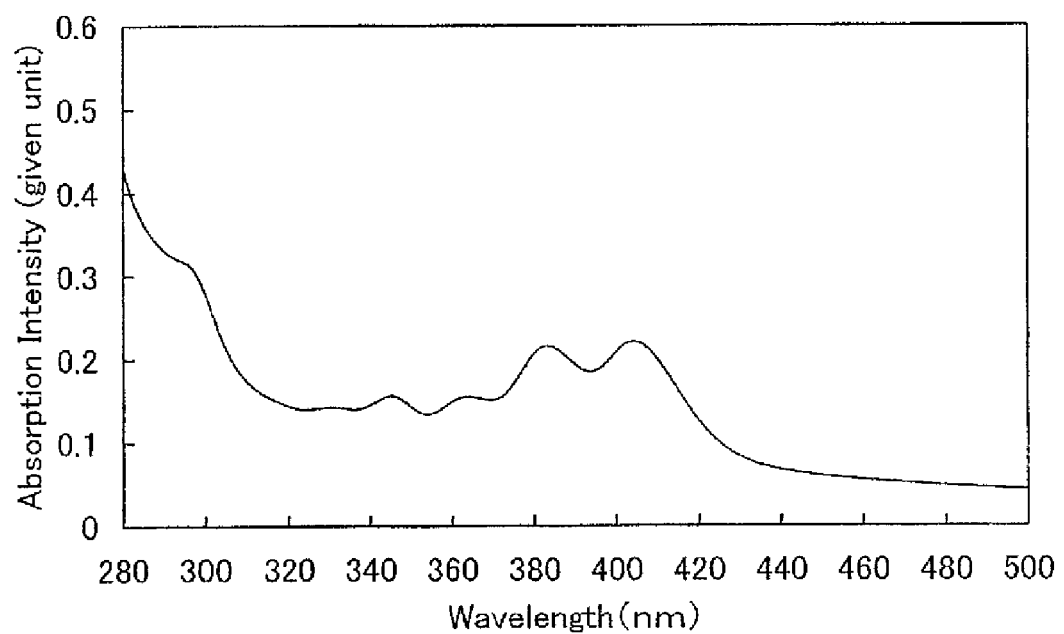
FIG. 32 is a graph showing an absorption spectrum of a thin film of 9-[4-(carbazol-9-yl)phenyl]-10-(2-naphthyl)anthracene.
Figure 33:
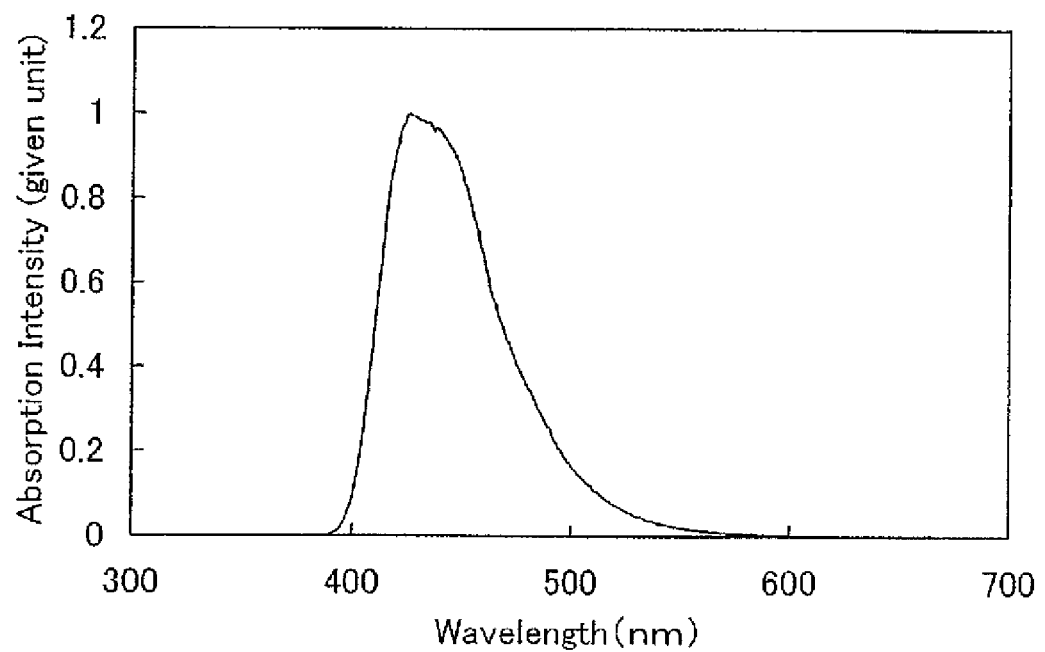
FIG. 33 is a graph showing an emission spectrum of a toluene solution of 9-[4-(carbazol-9-yl)phenyl]-10-(2-naphthyl)anthracene.
Figure 34:
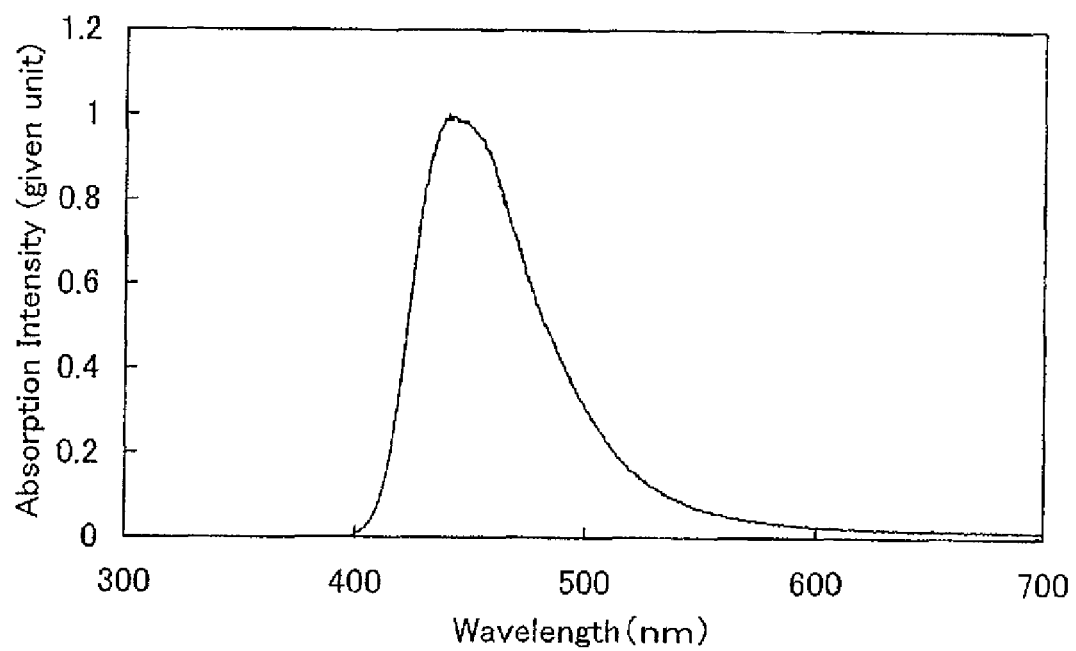
FIG. 34 is a graph showing an emission spectrum of a thin film of 9-[4-(carbazol-9-yl)phenyl]-10-(2-naphthyl)anthracene.

FIG. 31 shows an absorption spectrum of a toluene solution of βNCzPA. FIG. 32 shows an absorption spectrum of a thin film of βNCzPA. The measurement was conducted by using a UV-visible spectrophotometer (V-550, manufactured by JASCO Corporation). The solution was put in a quartz cell, and the thin film was evaporated on a quartz substrate to form the samples. The absorption spectra thereof, from each of which the absorption spectrum of quartz was subtracted, are shown in FIGS. 31 and 32. In FIGS. 31 and 32, the horizontal axis indicates a wavelength (nm) while the vertical axis indicates absorption intensity (given unit). In the case of the toluene solution, absorption based on an anthracene skeleton was observed at around 378 nm and 398 nm, and in the case of the thin film, absorption based on an anthracene skeleton was observed at around 384 nm and 404 nm. The light emission spectrum of the toluene solution of βNCzPA (excitation wavelength: 370 nm) is shown in FIG. 33, while that of the thin film of βNCzPA (excitation wavelength: 381 nm) is shown in FIG. 34. In FIGS. 33 and 34, the horizontal axis indicates a wavelength (nm) and the vertical axis indicates light emission intensity (given unit). The maximum light emission wavelength was 426 nm in the case of the toluene solution (excitation wavelength: 370 nm), and 440 nm in the case of the thin film (excitation wavelength: 381 nm).

In addition, the HOMO level of βNCzPA in the thin film state was −5.72 eV, which was measured by a photoelectron spectrometer (AC-2, manufactured by Riken Keiki Co., Ltd.) in the air. Moreover, the absorption edge was obtained from Tauc plot using data on the absorption spectrum of the thin film of βNCzPA in FIG. 32, When the absorption edge was estimated as an optical energy gap, the energy gap was 2.92 eV. Therefore, the LUMO level was −2.80 eV.

Moreover, the oxidation-reduction reaction characteristic of βNCzPA was measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Aldrich, 99.8%, catalog number: 22705-6) was used as a solvent. Tetra-n-butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to be 1 mmol/L. Further, a platinum electrode (a PTE platinum electrode, manufactured by BAS Inc.) was used as a work electrode. A platinum electrode (a VC-3 Pt counter electrode (5 cm), manufactured by BAS Inc.) was used as an auxiliary electrode. An Ag/Ag$^+$ electrode (an RE5 nonaqueous solvent reference electrode, manufactured by BAS Inc.) was used as a reference electrode. It is to be noted that the measurement was conducted at the room temperature.

The reduction reaction characteristic of βNCzPA was measured as follows. A scan for changing the potential of the work electrode with respect to the reference electrode from −2.40 V to −0.24 V after changing the potential from −0.24 V to −2.40 V was set as one cycle, and 100 cycles were measured. Further, the oxidation reaction characteristic of βNCzPA was measured as follows. A scan for changing the potential of the work electrode with respect to the reference electrode from 1.20 V to −0.30 V after changing the potential from −0.30 V to 1.20 V was set as one cycle, and 100 cycles were measured. Further, the scanning speed of the CV measurement was set to be 0.1 V/s.

Figure 64:
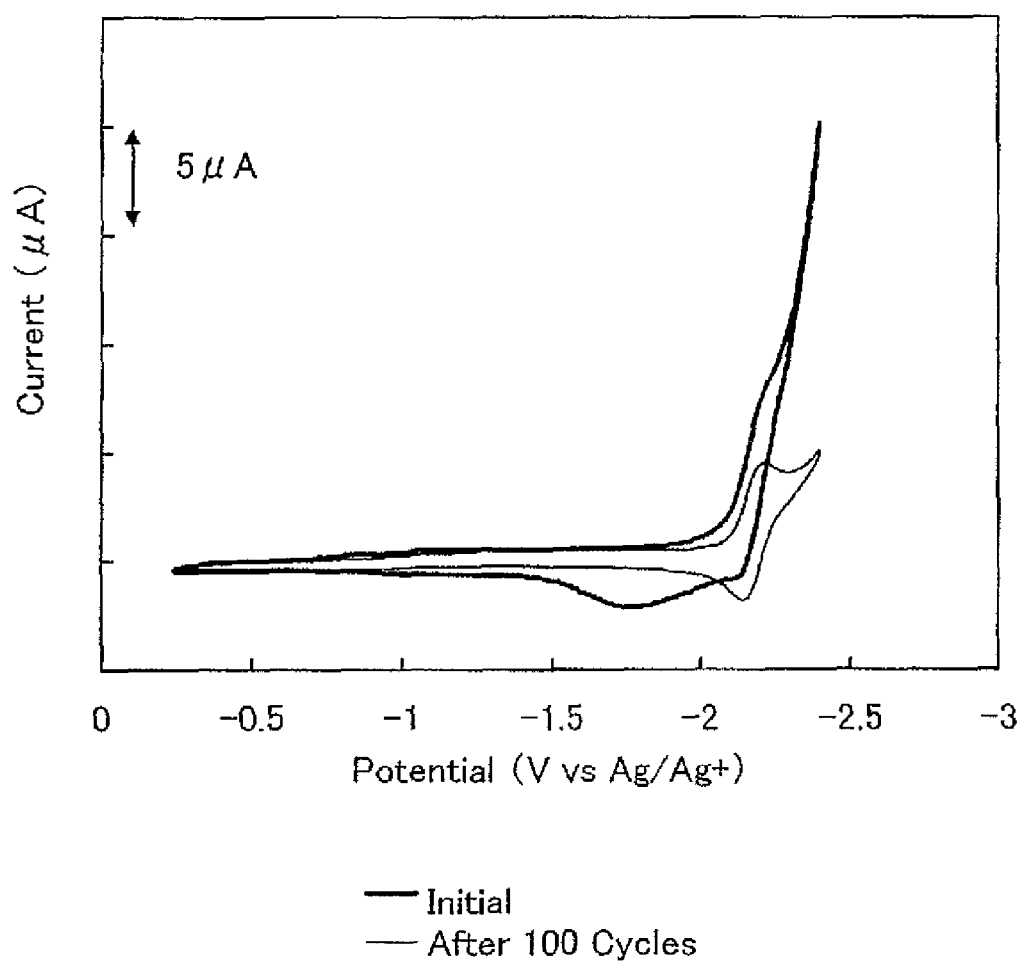
FIG. 64 is a graph showing a CV measurement result of a reduction side of 9-[4-(carbazol-9-yl)phenyl]-10-(2-naphthyl)anthracene.
Figure 65:
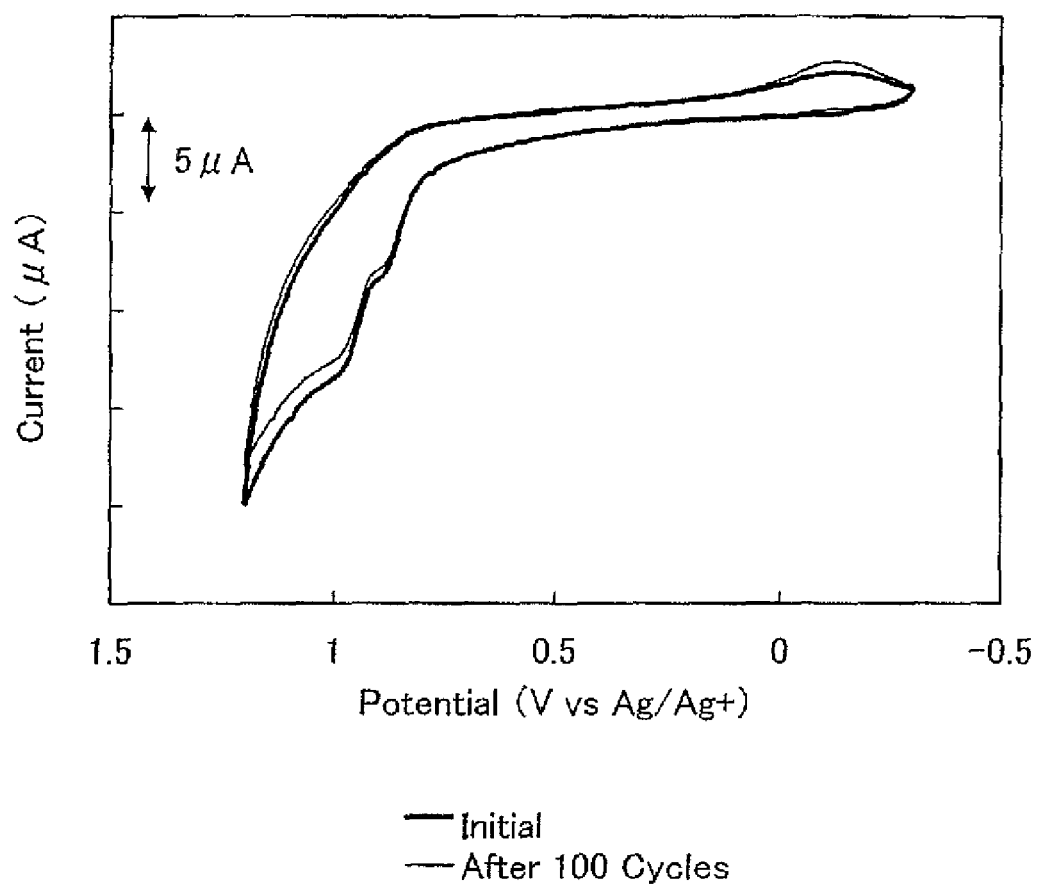
FIG. 65 is a graph showing a CV measurement result of an oxidation side of 9-[4-(carbazol-9-yl)phenyl]-10-(2-naphthyl)anthracene.

FIG. 64 shows a result of the CV measurement on the reduction side of βNCzPA, and FIG. 65 shows a result of the CV measurement on the oxidation side of βNCzPA. In FIG. 64 and FIG. 65, the horizontal axis indicates the potential (V) of the work electrode with respect to the reference electrode, while the vertical axis indicates a value (μA) of current flowing between the work electrode and the auxiliary electrode.

From FIG. 64 and FIG. 65, in the case of βNCzPA, reversible peaks are shown on the oxide side and the reduction side. In addition, even when 100 cycles of oxidation to reduction or reduction to oxidation were repeated, peak intensity is hardly changed. From the above, it is found that the anthracene derivative of the present invention is extremely stable to the repetition of oxidation-reduction reaction.

Embodiment 6

Figure 55:
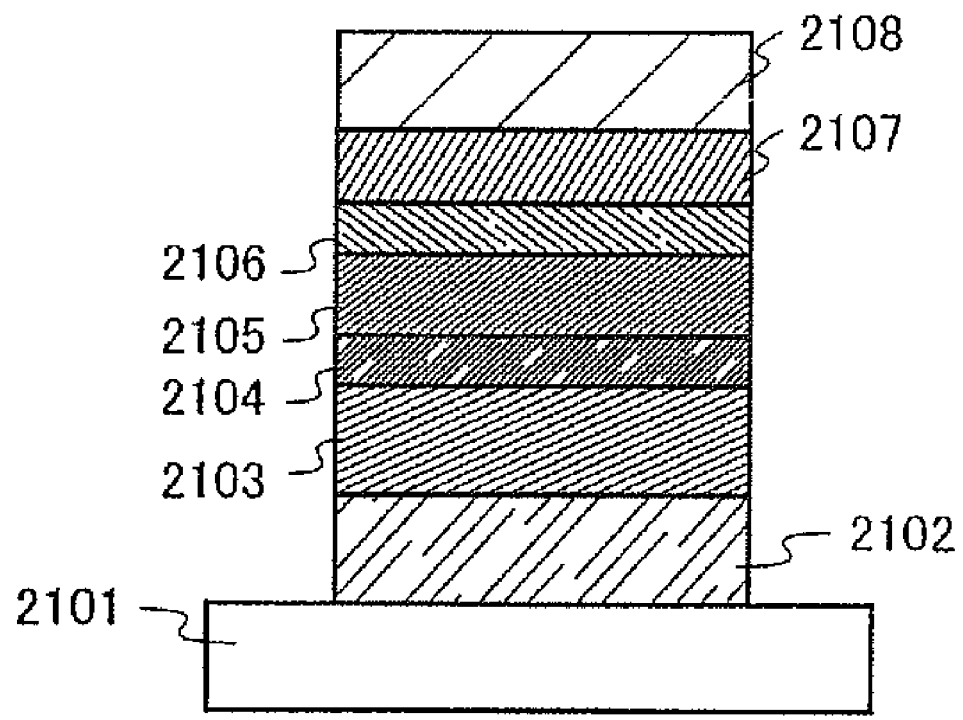
FIG. 55 is a view explaining a light-emitting element of embodiments.

In this embodiment, a light-emitting element of the present invention will be described with reference to FIG. 55. A chemical formula of a material used in this embodiment is shown below.

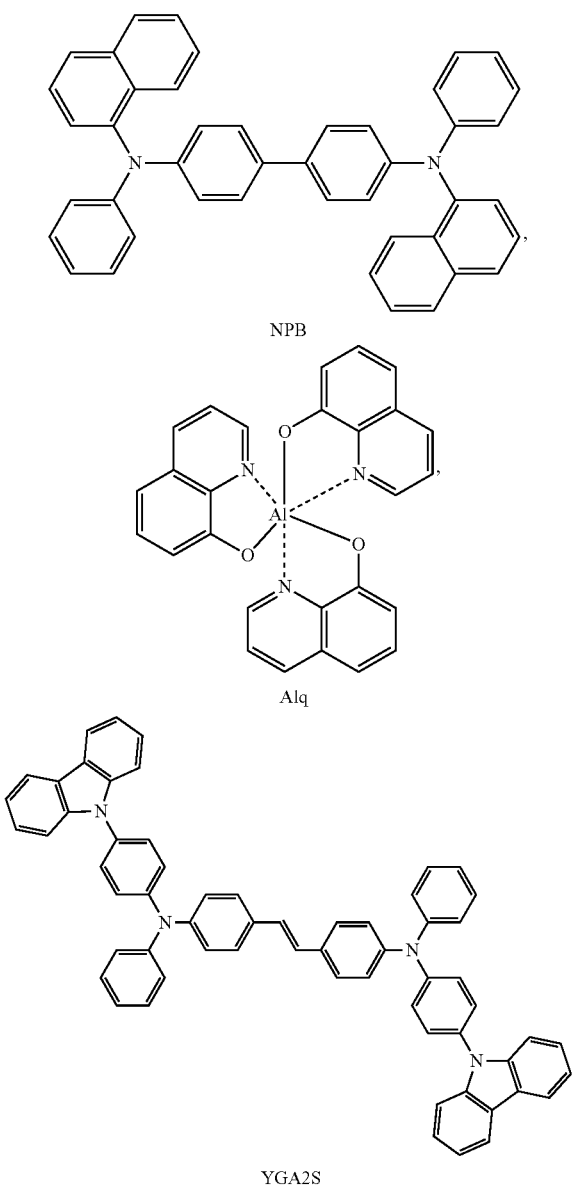

NPB

Alq

YGA2S

Hereinafter, a method for manufacturing a light-emitting element of this embodiment is shown.

First, indium tin oxide containing silicon oxide (ITSO) was deposited over a glass substrate 2101 by a sputtering method, so that a first electrode 2102 was formed. It is to be noted that the thickness thereof was 110 nm and an electrode area was 2 nm×2 nm.

Next, the substrate over which the first electrode was formed was fixed to a substrate holder provided in a vacuum evaporation apparatus in such a way that a surface of the substrate having the first electrode faced downward. The pressure was reduced to be about $10^{-4}$ Pa and then, 4,4'-bis [N-(1-napthyl)-N-phenylamino]biphenyl (abbreviation: NPB) and molybdenum oxide(VI) were co-evaporated on the first electrode 2102, thereby forming a layer 2103 containing a composite material of an organic compound and an inorganic compound. The film thickness of the layer 2103 was 50 nm, and the weight ratio between NPB and molybdenum oxide(VI) was set 4:1 (=NPB:molybdenum oxide). It is to be noted that the co-evaporation method is an evaporation method in which evaporation is performed at one time from plural evaporation sources in one process chamber.

Subsequently, a hole-transporting layer 2104 was formed having a thickness of 10 nm over the layer 2103 containing a composite material using 4,4'-bis[N-(1-napthyl)-N-phenylamino]biphenyl (abbreviation: NPB) by an evaporation method using resistance heating.

Further, a light-emitting layer 2105 having a thickness of 30 nm was formed over the hole-transporting layer 2104 by co-evaporating 9-[4-(N-carbazolyl)]phenyl-10-phenylanthracene (abbreviation: CzPA) represented by the structural formula (11) and N,N'-bis[4-(9H-carbazol-9-yl)phenyl]-N, N'-diphenylstilbene-4,4'-diamine (abbreviation: YGA2S). Here, the weight ratio between CzPA and YGA2S was adjusted so as to be 1:0.05 (=CzPA:YGA2S).

After that, an electron-transporting layer 2106 was formed having a thickness of 10 nm using tris(8-quinolinolato)aluminum (abbreviation: Alq) over the light-emitting layer 2105 by an evaporation method using resistance heating.

Moreover, an electron-injecting layer 2107 was formed having a thickness of 20 nm by co-evaporating tris(8-quinolinolato)aluminum (abbreviation: Alq) and lithium over the electron-transporting layer 2106. Here, the weight ratio between Alq and lithium was adjusted so as to be 1:01 (=Alq:lithium).

Then, a second electrode 2108 was formed of aluminum having a thickness of 200 nm over the electron-injecting layer 2107 by an evaporation method using resistance heating. Thus, a light-emitting element 1 was manufactured.

Figure 35:
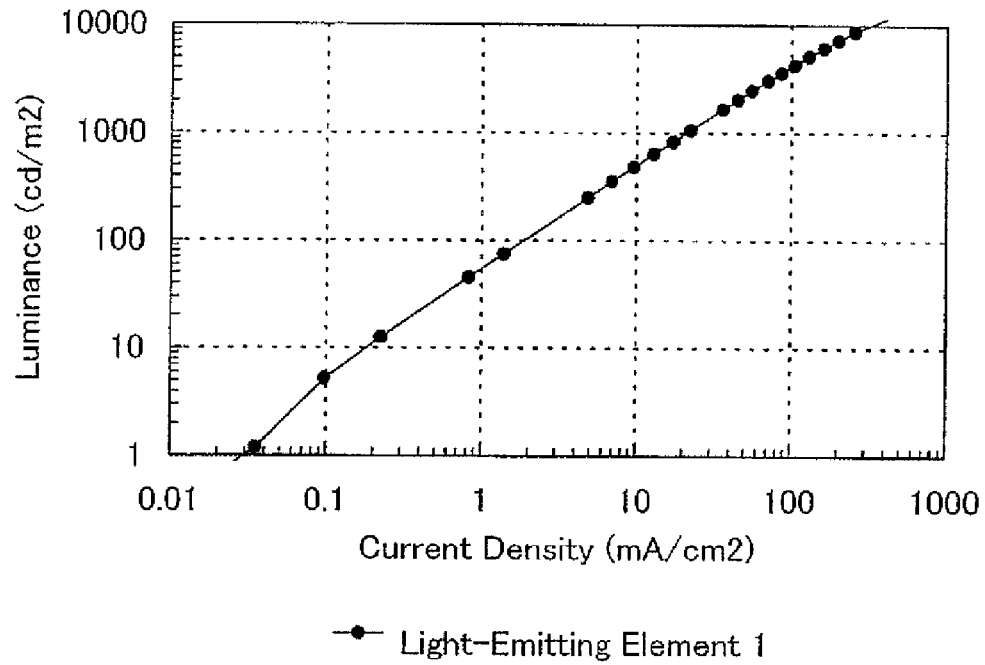
FIG. 35 is a graph showing current density vs. luminance characteristics of a light-emitting element manufactured in Embodiment 6.
Figure 36:
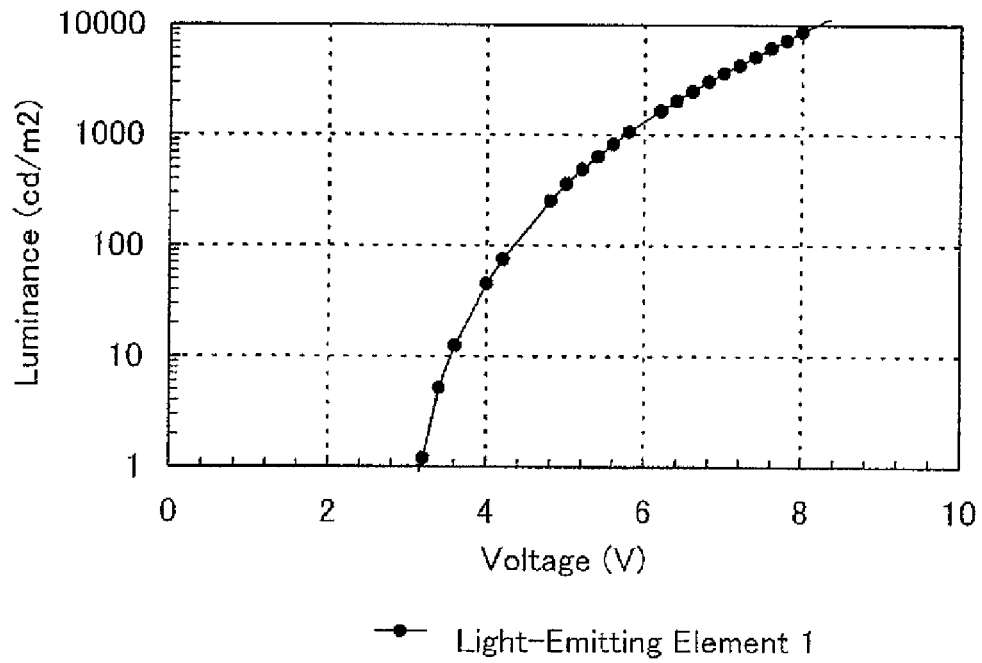
FIG. 36 is a graph showing voltage vs. luminance characteristics of a light-emitting element manufactured in Embodiment 6.
Figure 37:
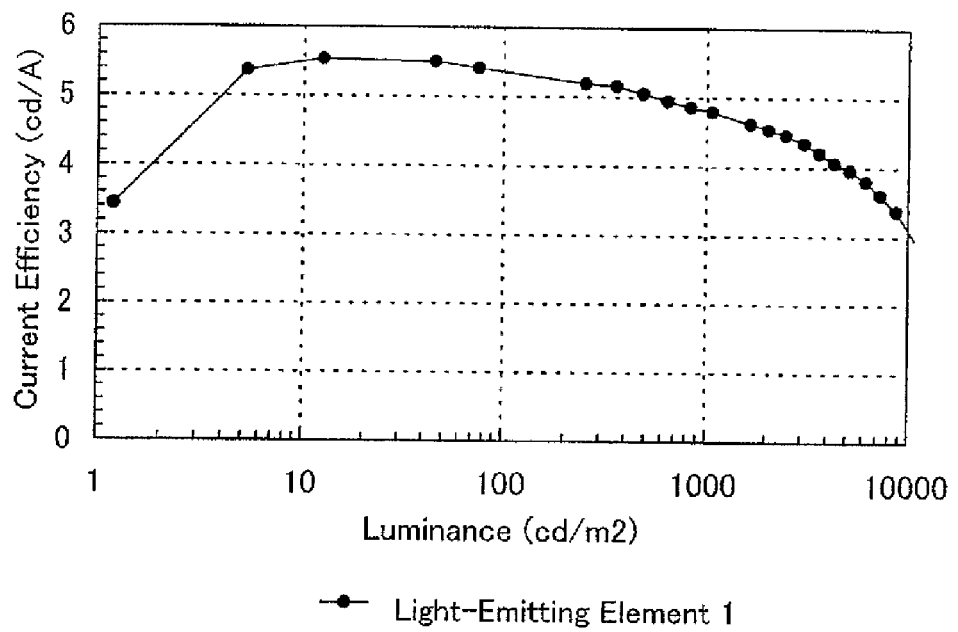
FIG. 37 is a graph showing luminance vs. current efficiency characteristics of a light-emitting element manufactured in Embodiment 6.
Figure 38:
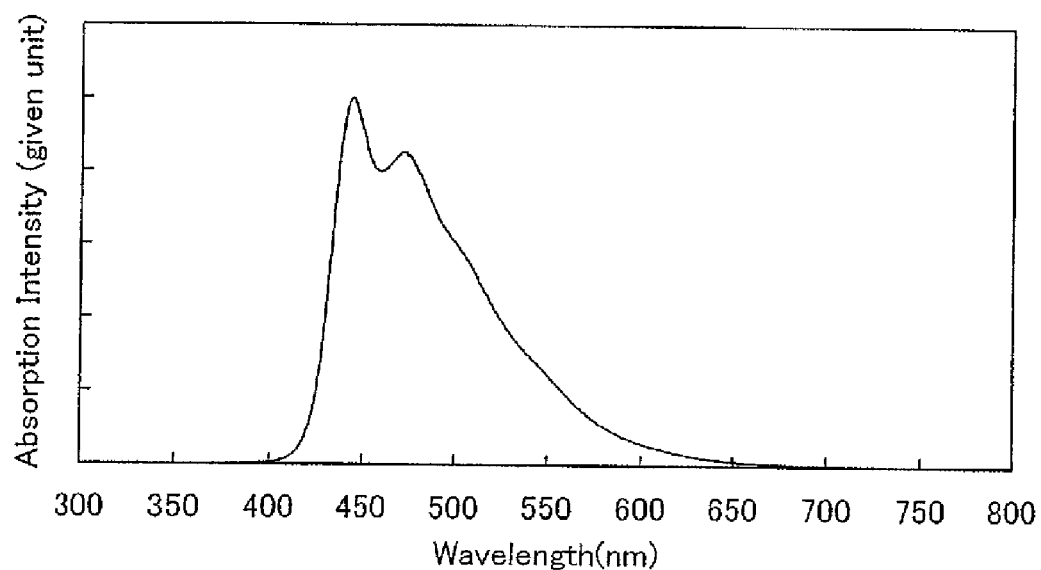
FIG. 38 is a graph showing an emission spectrum of a light-emitting element manufactured in Embodiment 6.

FIG. 35 shows current density vs. luminance characteristics of the light-emitting element 1, FIG. 36 shows voltage vs. luminance characteristics thereof, and FIG. 37 shows luminance vs. current efficiency characteristics thereof. Also, FIG. 38 shows the emission spectrum which was obtained at a current of 1 mA. A CIE chromaticity coordinate of the light-emitting element 1 at luminance of 1064 cd/m² was (x=0.17, y=0.20), and light emission was blue. Current efficiency at luminance of 1064 cd/m² was 4.8 cd/A, and at that time, the voltage was 5.8 V and the current density was 22.2 mA/cm². In addition, as shown in FIG. 38, maximum emission wavelength at a current of 1 mA was 444 nm.

Embodiment 7

In this embodiment, a light-emitting element of the present invention will be described with reference to FIG. 55. Hereinafter, a method for manufacturing a light-emitting element of this embodiment is shown.

First, indium tin oxide containing silicon oxide (ITSO) was deposited over a glass substrate 2101 by a sputtering method, so that a first electrode 2102 was formed. It is to be noted that the thickness thereof was 110 nm and an electrode area was 2 nm×2 nm.

Next, the substrate over which the first electrode was formed was fixed to a substrate holder provided in a vacuum evaporation apparatus in such a way that a surface of the substrate having the first electrode faced downward. The pressure was reduced to be about $10^{-4}$ Pa and then, 4,4'-bis [N-(1-napthyl)-N-phenylamino]biphenyl (abbreviation: NPB) and molybdenum oxide(VI) were co-evaporated on the first electrode 2102, thereby forming a layer 2103 containing a composite material of an organic compound and an inorganic compound. The film thickness of the layer 2103 was 50 nm, and the weight ratio between NPB and molybdenum oxide(VI) was set 4:1 (=NPB:molybdenum oxide). It is to be noted that the co-evaporation method is an evaporation method in which evaporation is performed at one time from plural evaporation sources in one process chamber.

Subsequently, a hole-transporting layer 2104 was formed having a thickness of 10 nm over the layer 2103 containing a composite material using 4,4'-bis[N-(1-napthyl)-N-phenylamino]biphenyl (abbreviation: NPB) by an evaporation method using resistance heating.

Further, a light-emitting layer 2105 having a thickness of 30 nm was formed over the hole-transporting layer 2104 by co-evaporating 9-(biphenyl-4-yl)-10-[4-(carbazol-9-yl)phenyl]anthracene (abbreviation: PPCzPA) represented by the structural formula (12) and N,N'-bis[4-(9H-carbazol-9-yl)pheny]-N,N'-diphenylstilbene-4,4'-diamine (abbreviation: YGA2S). Here, the weight ratio between PPCzPA and YGA2S was adjusted so as to be 1:0.05 (=PPCzPA:YGA2S).

After that, an electron-transporting layer 2106 was formed having a thickness of 10 nm using tris(8-quinolinolato)aluminum (abbreviation: Alq) over the light-emitting layer 2105 by an evaporation method using resistance heating.

Moreover, an electron-injecting layer 2107 was formed having a thickness of 20 nm by co-evaporating tris(8-quinolinolato)aluminum (abbreviation: Alq) and lithium over the electron-transporting layer 2106. Here, the weight ratio between Alq and lithium was adjusted so as to be 1:0.01 (=Alq:lithium).

Then, a second electrode 2108 was formed of aluminum having a thickness of 200 nm over the electron-injecting layer 2107 by an evaporation method using resistance heating. Thus, a light-emitting element 2 was manufactured.

Figure 39:
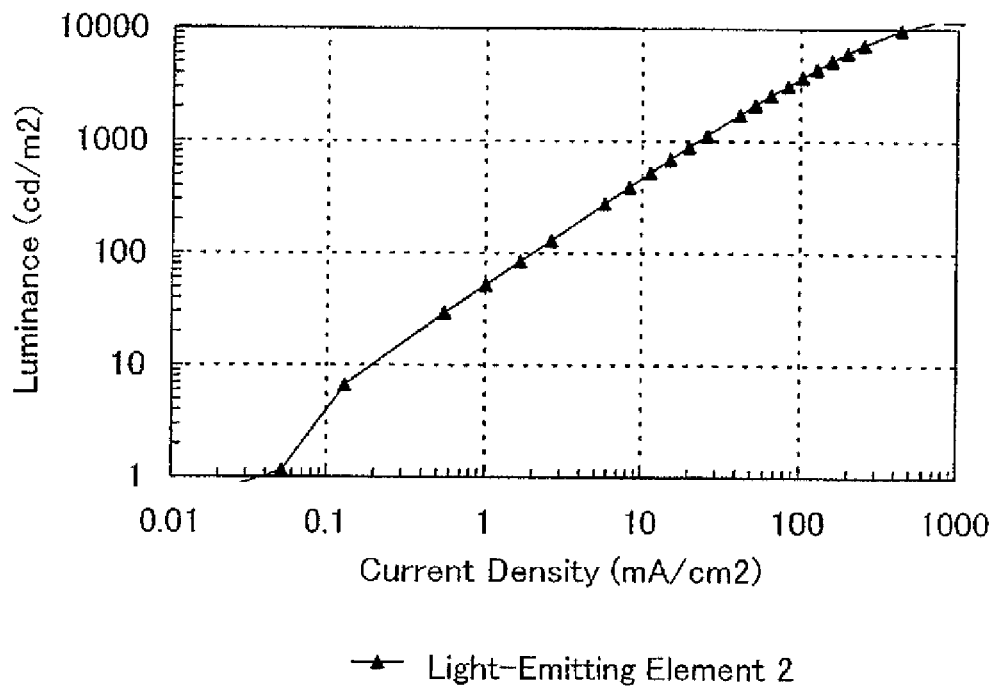
FIG. 39 is a graph showing current density vs. luminance characteristics of a light-emitting element manufactured in Embodiment 7.
Figure 40:
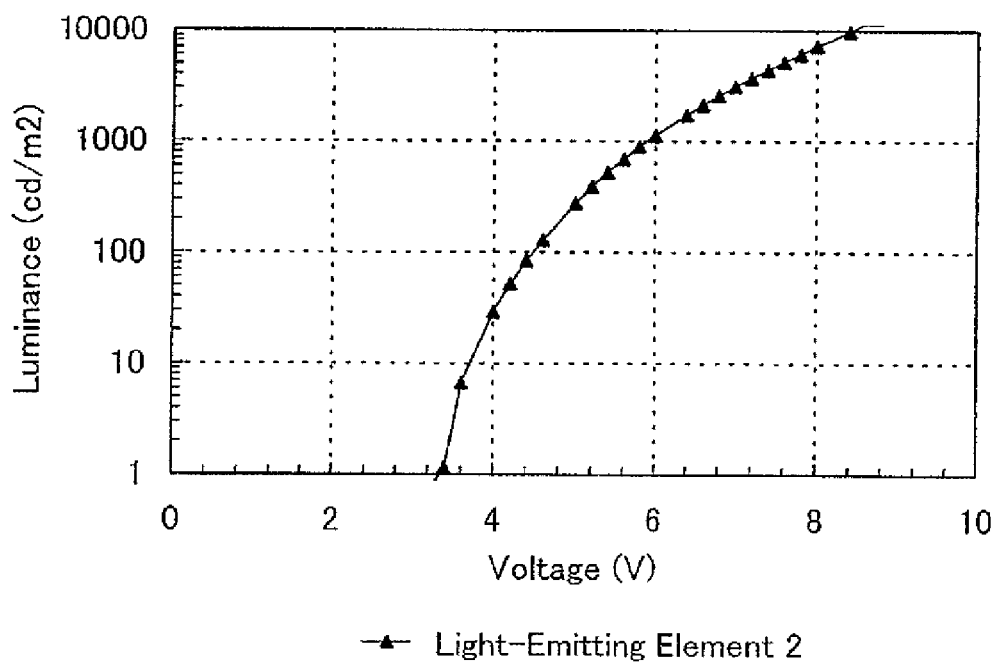
FIG. 40 is a graph showing voltage vs. luminance characteristics of a light-emitting element manufactured in Embodiment 7.
Figure 41:
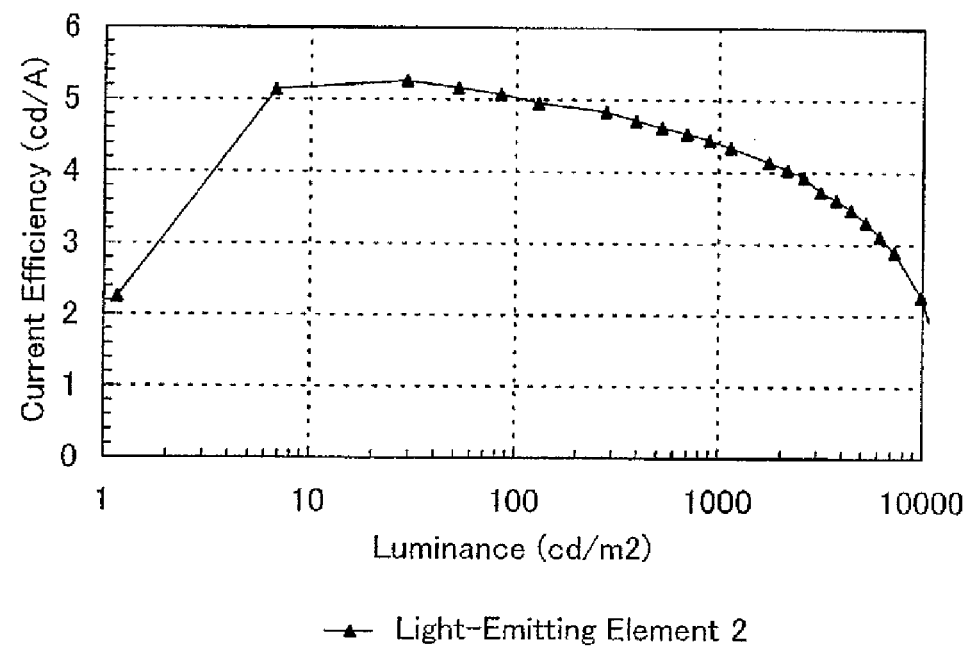
FIG. 41 is a graph showing luminance vs. current efficiency characteristics of a light-emitting element manufactured in Embodiment 7.
Figure 42:
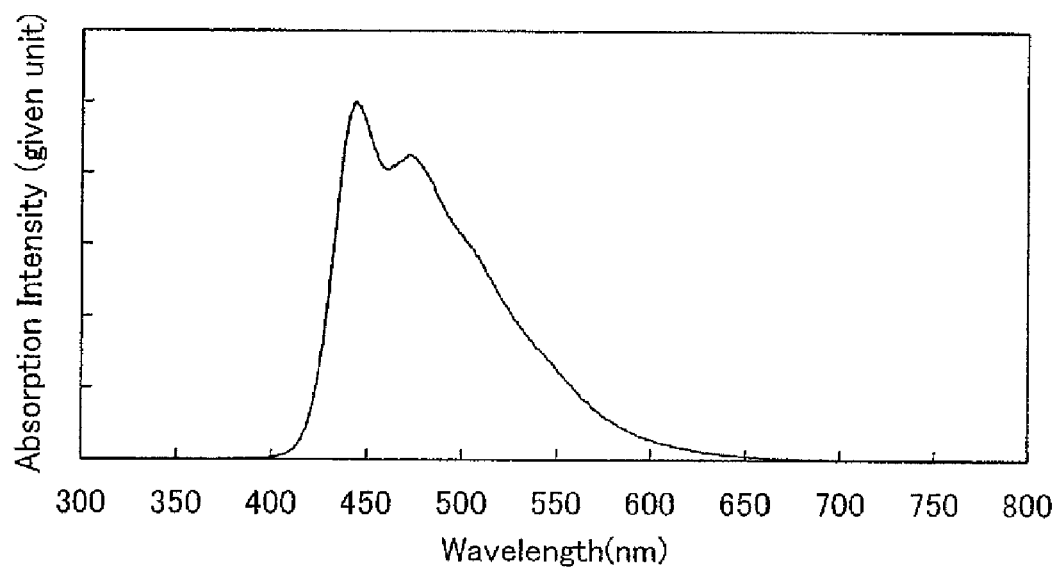
FIG. 42 is a graph showing an emission spectrum of a light-emitting element manufactured in Embodiment 7.

FIG. 39 shows current density vs. luminance characteristics of the light-emitting element 2, FIG. 40 shows voltage vs. luminance characteristics thereof, and FIG. 41 shows luminance vs. current efficiency characteristics thereof. Also, FIG. 42 shows the emission spectrum which was obtained at a current of 1 mA. A CIE chromaticity coordinate of the light-emitting element 2 at luminance of 895 cd/m$^2$ was (x=0.17, y=0.20), and light emission was blue. Current efficiency at luminance of 895 cd/m$^2$ was 4.4 cd/A, and at that time, the voltage was 5.8 V and the current density was 20.1 mA/cm$^2$. In addition, as shown in FIG. 42, maximum emission wavelength at a current of 1 mA was 443 nm.

Embodiment 8

In this embodiment, a light-emitting element of the present invention will be described with reference to FIG. 55. Hereinafter, a method for manufacturing a light-emitting element of this embodiment is shown.

First, indium tin oxide containing silicon oxide (ITSO) was deposited over a glass substrate 2101 by a sputtering method, so that a first electrode 2102 was formed. It is to be noted that the thickness thereof was 110 nm and an electrode area was 2 nm×2 nm.

Next, the substrate over which the first electrode was formed was fixed to a substrate holder provided in a vacuum evaporation apparatus in such a way that a surface of the substrate having the first electrode faced downward. The pressure was reduced to be about 10$^{-4}$ Pa and then, 4,4'-bis[N-(1-napthyl)-N-phenylamino]biphenyl (abbreviation: NPB) and molybdenum oxide(VI) were co-evaporated on the first electrode 2102, thereby forming a layer 2103 containing a composite material of an organic compound and an inorganic compound. The film thickness of the layer 2103 was 50 nm, and the weight ratio between NPB and molybdenum oxide(VI) was set 4:1 (=NPB:molybdenum oxide). It is to be noted that the co-evaporation method is an evaporation method in which evaporation is performed at one time from plural evaporation sources in one process chamber.

Subsequently, a hole-transporting layer 2104 was formed having a thickness of 10 nm over the layer 2103 containing a composite material using 4,4'-bis[N-(1-napthyl)-N-phenylamino]biphenyl (abbreviation: NPB) by an evaporation method using resistance heating.

Further, a light-emitting layer 2105 having a thickness of 30 nm was formed over the hole-transporting layer 2104 by co-evaporating 9-(4-tert-butylphenyl)-10-[4-(carbazol-9-yl)]phenylanthracene (abbreviation: PTBCzPA) represented by the structural formula (20) and N,N'-bis[4-(9H-carbazol-9-yl)phenyl]-N,N'-diphenylstilbene-4,4'-diamine (abbreviation: YGA2S). Here, the weight ratio between PTBCzPA and YGA2S was adjusted so as to be 1:0.05 (=PTBCzPA:YGA2S).

After that, an electron-transporting layer 2106 was formed having a thickness of 10 nm using tris(8-quinolinolato)aluminum (abbreviation: Alq) over the light-emitting layer 2105 by an evaporation method using resistance heating.

Moreover, an electron-injecting layer 2107 was formed having a thickness of 20 nm by co-evaporating tris(8-quinolinolato)aluminum (abbreviation: Alq) and lithium over the electron-transporting layer 2106. Here, the weight ratio between Alq and lithium was adjusted so as to be 1:0.01 (=Alq:lithium).

Then, a second electrode 2108 was formed of aluminum having a thickness of 200 nm over the electron-injecting layer 2107 by an evaporation method using resistance heating. Thus, a light-emitting element 3 was manufactured.

Figure 43:
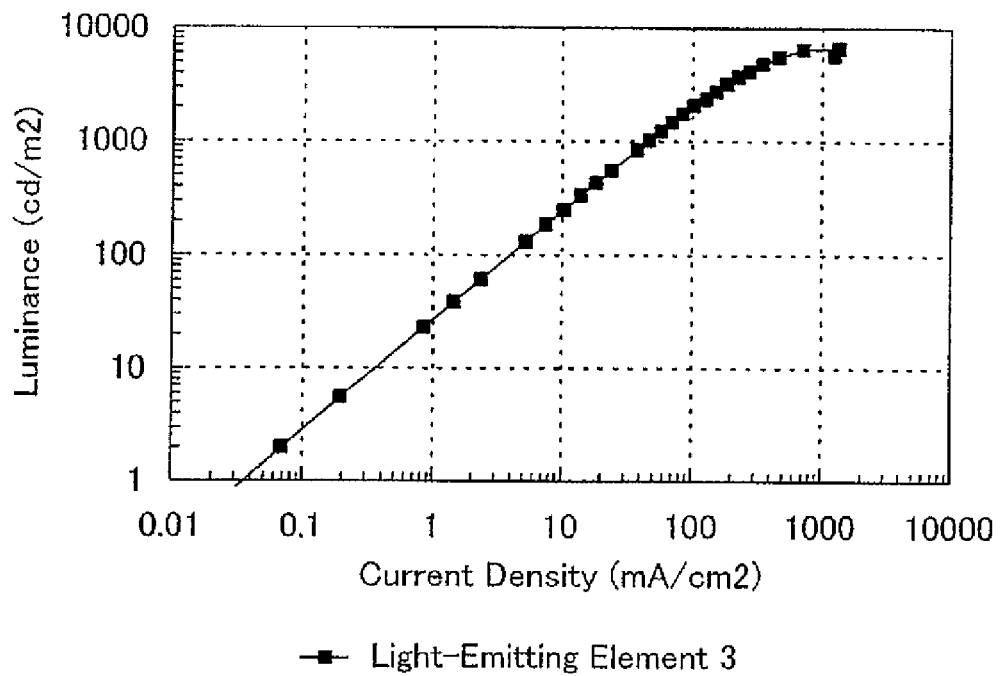
FIG. 43 is a graph showing current density vs. luminance characteristics of a light-emitting element manufactured in Embodiment 8.
Figure 44:
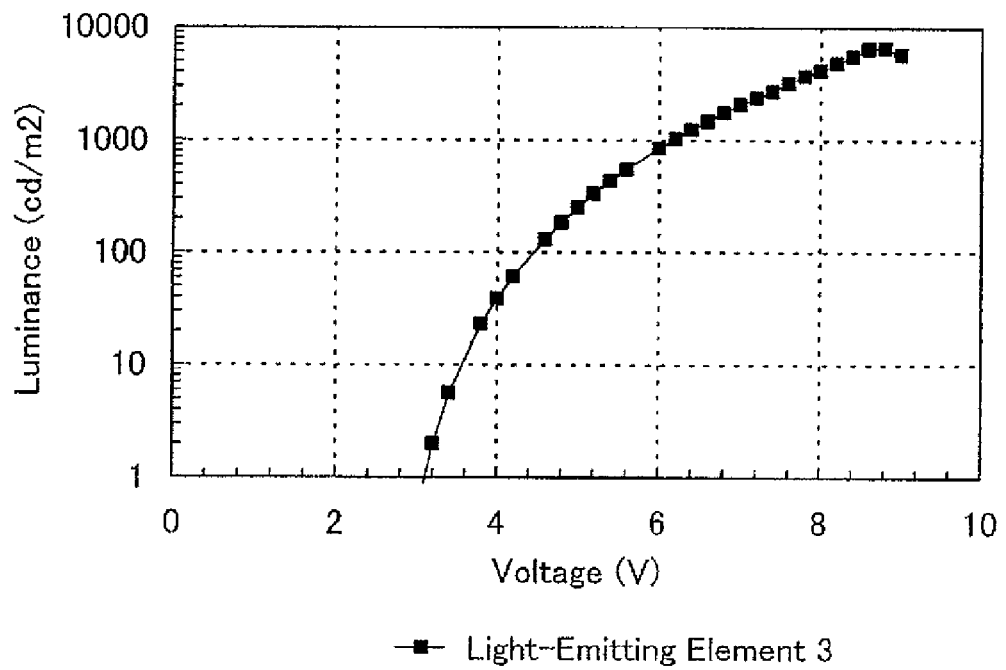
FIG. 44 is a graph showing voltage vs. luminance characteristics of a light-emitting element manufactured in Embodiment 8.
Figure 45:
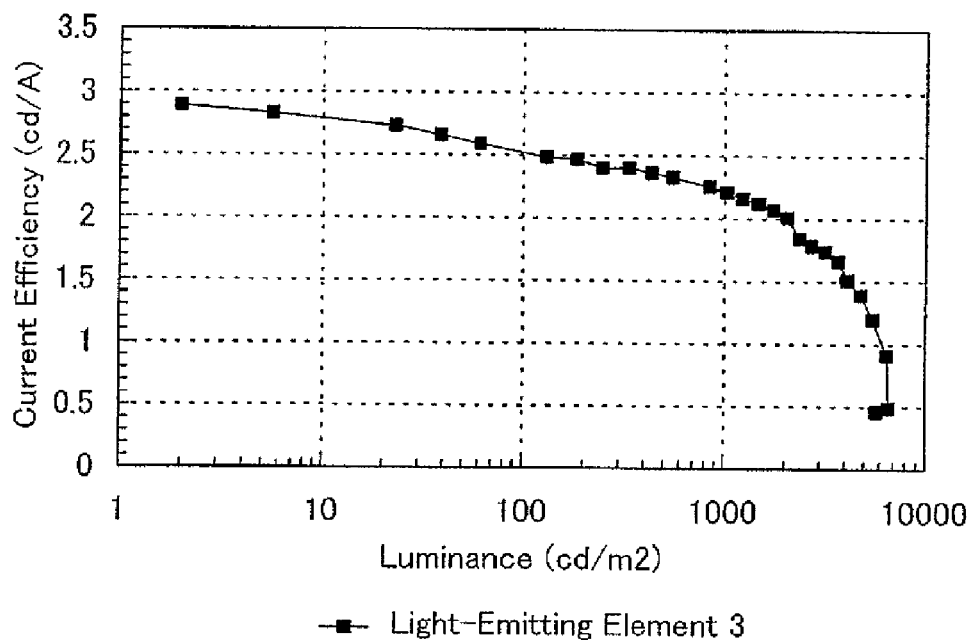
FIG. 45 is a graph showing luminance vs. current efficiency characteristics of a light-emitting element manufactured in Embodiment 8.
Figure 46:
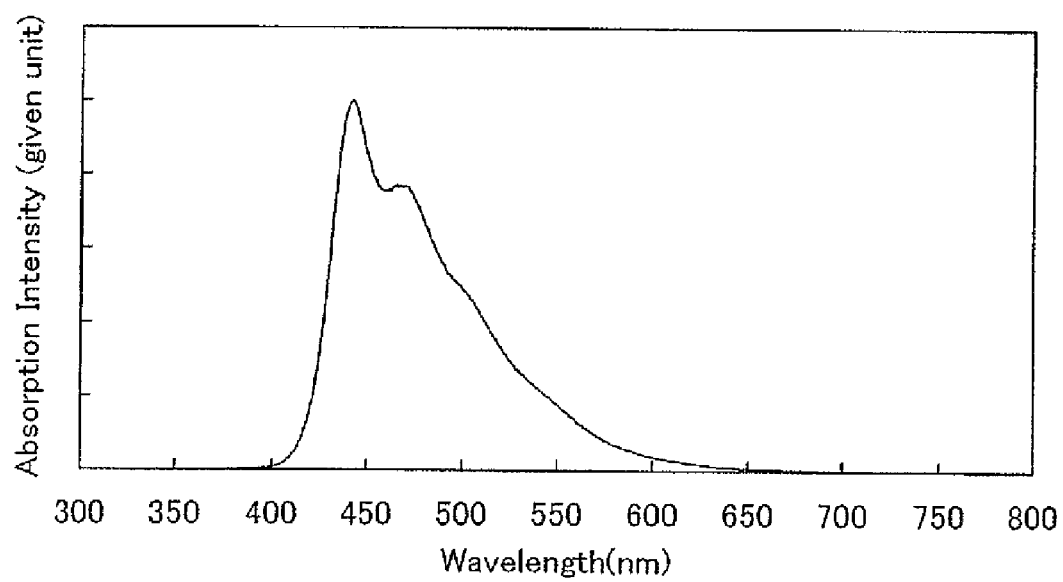
FIG. 46 is a graph showing an emission spectrum of a light-emitting element manufactured in Embodiment 8.

FIG. 43 shows current density vs. luminance characteristics of the light-emitting element 3, FIG. 44 shows voltage vs. luminance characteristics thereof, and FIG. 45 shows luminance vs. current efficiency characteristics thereof. Also, FIG. 46 shows the emission spectrum which was obtained at a current of 1 mA. A CIE chromaticity coordinate of the light-emitting element 3 at luminance of 1025 cd/m$^2$ was (x=0.16, y=0.16), and light emission was blue. Current efficiency at luminance of 1025 cd/m$^2$ was 2.2 cd/A, and at that time, the voltage was 6.2 V and the current density was 46.4 mA/cm$^2$. In addition, as shown in FIG. 46, maximum emission wavelength at a current of 1 mA was 442 nm.

Embodiment 9

In this embodiment, a light-emitting element of the present invention will be described with reference to FIG. 55. Hereinafter, a method for manufacturing a light-emitting element of this embodiment is shown.

First, indium tin oxide containing silicon oxide (ITSO) was deposited over a glass substrate 2101 by a sputtering method, so that a first electrode 2102 was formed. It is to be noted that the thickness thereof was 110 nm and an electrode area was 2 nm×2 nm.

Next, the substrate over which the first electrode was formed was fixed to a substrate holder provided in a vacuum evaporation apparatus in such a way that a surface of the substrate having the first electrode faced downward. The pressure was reduced to be about 10$^{-4}$ Pa and then, 4,4'-bis[N-(1-napthyl)-N-phenylamino]biphenyl (abbreviation: NPB) and molybdenum oxide(VI) were co-evaporated on the first electrode 2102, thereby forming a layer 2103 containing a composite material of an organic compound and an inorganic compound. The film thickness of the layer 2103 was 50 nm, and the weight ratio between NPB and molybdenum oxide(VI) was set 4:1 (=NPB:molybdenum oxide). It is to be noted that the co-evaporation method is an evaporation method in which evaporation is performed at one tine from plural evaporation sources in one process chamber.

Subsequently, a hole-transporting layer 2104 was formed having a thickness of 10 nm over the layer 2103 containing a composite material using 4,4'-bis[N-(1-napthyl)-N-phenylamino]biphenyl (abbreviation: NPB) by an evaporation method using resistance heating.

Further, a light-emitting layer 2105 having a thickness of 30 nm was formed over the hole-transporting layer 2104 by co-evaporating 9-[4-(carbazol-9-yl)phenyl]-10-(2-naphthyl)anthracene (abbreviation: βNCzPA) represented by the structural formula (16) and N,N'-bis[4-(9H-carbazol-9-yl)phenyl]-N,N'-diphenylstilbene-4,4'-diamine (abbreviation: YGA2S). Here, the weight ratio between βNCzPA and YGA2S was adjusted so as to be 1:0.05 (=βNCzPA:YGA2S).

After that, an electron-transporting layer 2106 was formed having a thickness of 10 nm using tris(8-quinolinolato)aluminum (abbreviation: Alq) over the light-emitting layer 2105 by an evaporation method using resistance heating.

Moreover, an electron-injecting layer 2107 was formed having a thickness of 20 nm by co-evaporating tris(8-quinolinolato)aluminum (abbreviation: Alq) and lithium over the electron-transporting layer 2106. Here, the weight ratio between Alq and lithium was adjusted so as to be 1:0.01 (=Alq:lithium).

Then, a second electrode 2108 was formed of aluminum having a thickness of 200 nm over the electron-injecting layer 2107 by an evaporation method using resistance heating. Thus, a light-emitting element 4 was manufactured.

Figure 47:
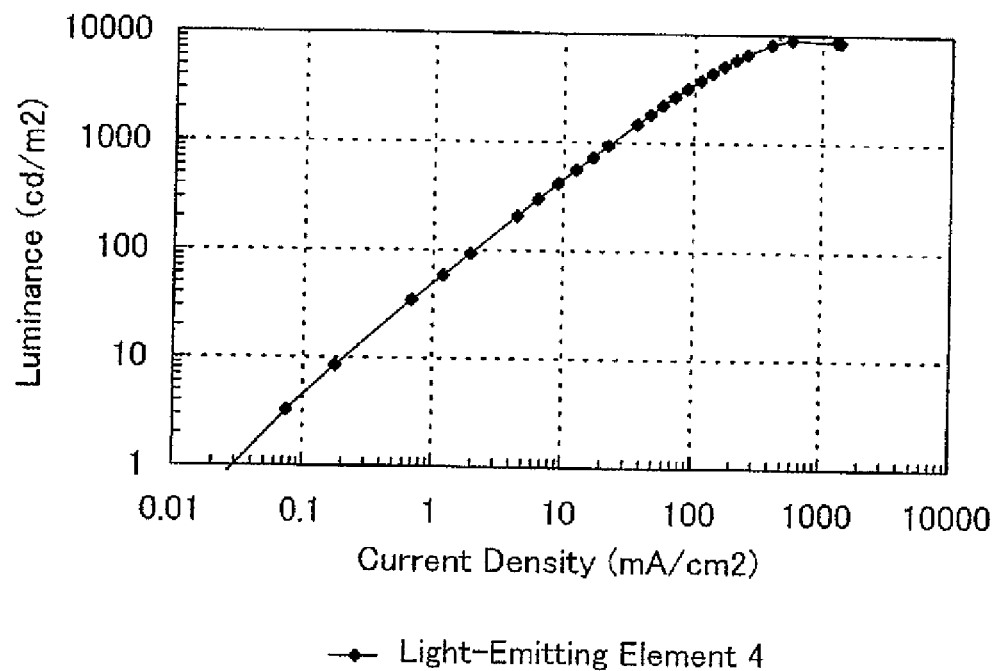
FIG. 47 is a graph showing current density vs. luminance characteristics of a light-emitting element manufactured in Embodiment 9.
Figure 48:
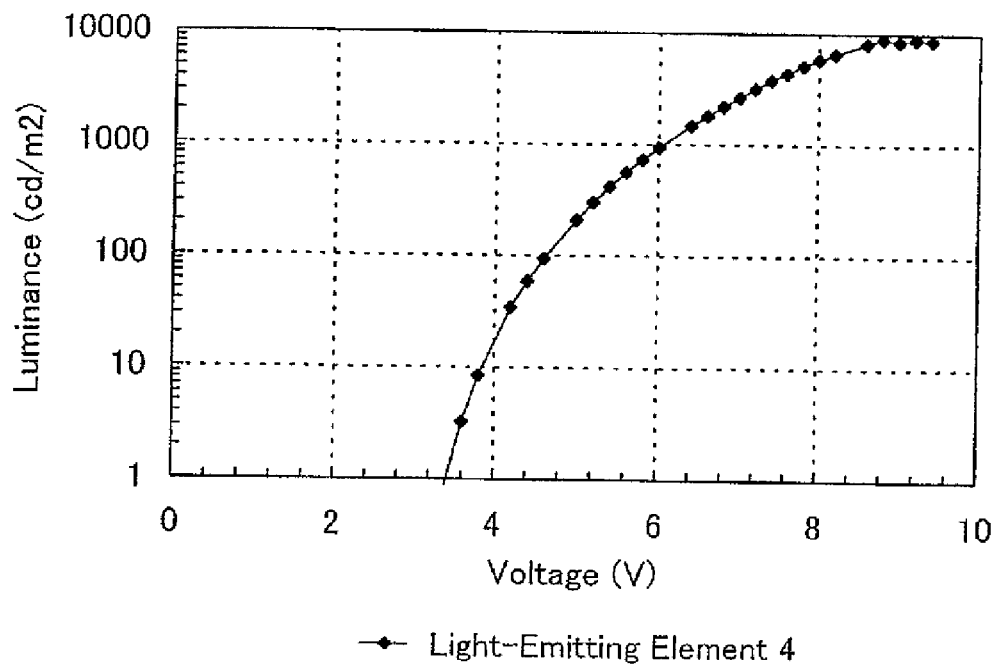
FIG. 48 is a graph showing voltage vs. luminance characteristics of a light-emitting element manufactured in Embodiment 9.
Figure 49:
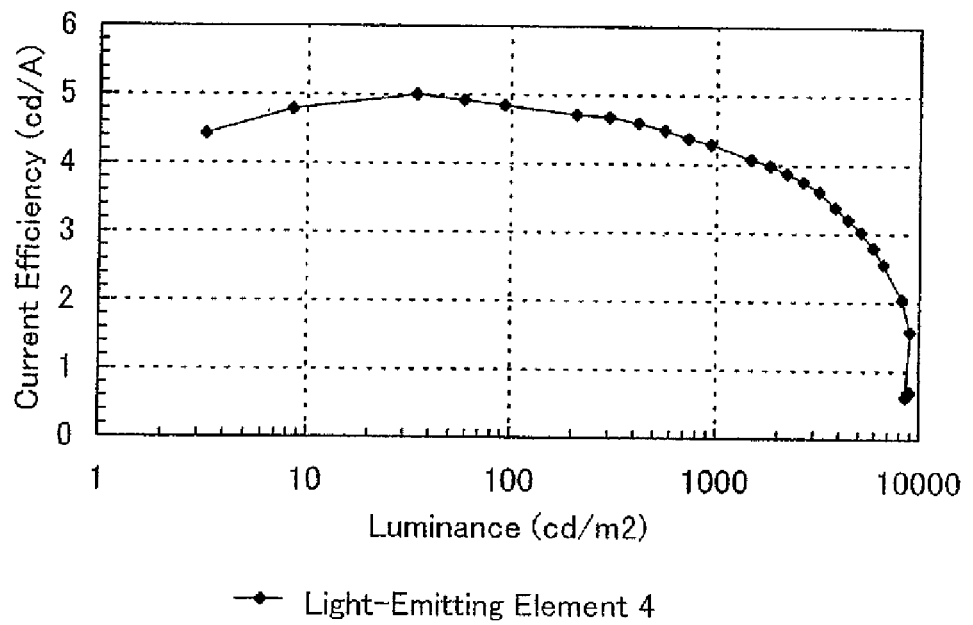
FIG. 49 is a graph showing luminance vs. current efficiency characteristics of a light-emitting element manufactured in Embodiment 9.
Figure 50:
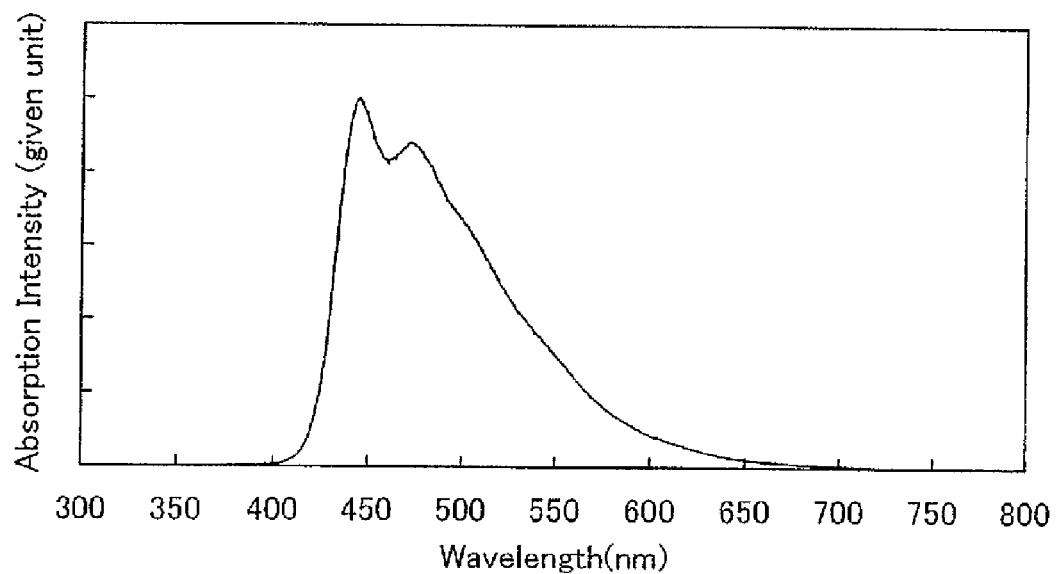
FIG. 50 is a graph showing an emission spectrum of a light-emitting element manufactured in Embodiment 9.

FIG. 47 shows current density vs. luminance characteristics of the light-emitting element 4, FIG. 48 shows voltage vs. luminance characteristics thereof, and FIG. 49 shows luminance vs. current efficiency characteristics thereof. Also, FIG. 50 shows the emission spectrum which was obtained at a current of 1 mA. A CIE chromaticity coordinate of the light-emitting element 4 at luminance of 938 cd/m$^2$ was (x=0.18, y=0.22), and light emission was blue. Current efficiency at luminance of 938 cd/m$^2$ was 4.3 cd/A, and at that time, the voltage was 6.0 V and the current density was 21.9 mA/cm$^2$. In addition, as shown in FIG. 50, maximum emission wavelength at a current of 1 mA was 445 nm.

Embodiment 10

In this embodiment, a light-emitting element of the present invention will be described with reference to FIG. 55. Hereinafter, a method for manufacturing a light-emitting element of this embodiment is shown.

First, indium tin oxide containing silicon oxide (ITSO) was deposited over a glass substrate 2101 by a sputtering method, so that a first electrode 2102 was formed. It is to be noted that the thickness thereof was 110 nm and an electrode area was 2 nm×2 nm.

Next, the substrate over which the first electrode was formed was fixed to a substrate holder provided in a vacuum evaporation apparatus in such a way that a surface of the substrate having the first electrode faced downward. The pressure was reduced to be about 10$^{-4}$ Pa and then, 4,4'-bis[N-(1-napthyl)-N-phenylamino]biphenyl (abbreviation: NPB) and molybdenum oxide(VI) were co-evaporated on the first electrode 2102, thereby forming a layer 2103 containing a composite material of an organic compound and an inorganic compound. The film thickness of the layer 2103 was 50 nm, and the weight ratio between NPB and molybdenum oxide(VI) was set 4:1 (=NPB:molybdenum oxide). It is to be noted that the co-evaporation method is an evaporation method in which evaporation is performed at one time from plural evaporation sources in one process chamber.

Subsequently, a hole-transporting layer 2104 was formed having a thickness of 10 nm over the layer 2103 containing a composite material using 4,4'-bis[N-(1-napthyl)-N-phenylamino]biphenyl (abbreviation: NPB) by an evaporation method using resistance heating.

Further, a light-emitting layer 2105 having a thickness of 30 nm was formed over the hole-transporting layer 2104 by co-evaporating 9-[4-(carbazol-9-yl)phenyl]-10-(4-trifluoromethylphenyl)anthracene (CF3CzPA) represented by the structural formula (42) and N,N'-bis[4-(9H-carbazol-9-yl)phenyl]-N,N'-diphenylstilbene-4,4'-diamine (abbreviation: YGA2S). Here, the weight ratio between CF3CzPA and YGA2S was adjusted so as to be 1:0.05 (=CF3CzPA:YGA2S).

After that, an electron-transporting layer 2106 was formed having a thickness of 10 nm using tris(8-quinolinolato)aluminum (abbreviation: Alq) over the light-emitting layer 2105 by an evaporation method using resistance heating.

Moreover, an electron-injecting layer 2107 was formed having a thickness of 20 nm by co-evaporating tris(8-quinolinolato)aluminum (abbreviation: Alq) and lithium over the electron-transporting layer 2106. Here, the weight ratio between Alq and lithium was adjusted so as to be 1:0.01 (=Alq:lithium).

Then, a second electrode 2108 was formed of aluminum having a thickness of 200 nm over the electron-injecting layer 2107 by an evaporation method using resistance heating. Thus, a light-emitting element 5 was manufactured.

Figure 51:
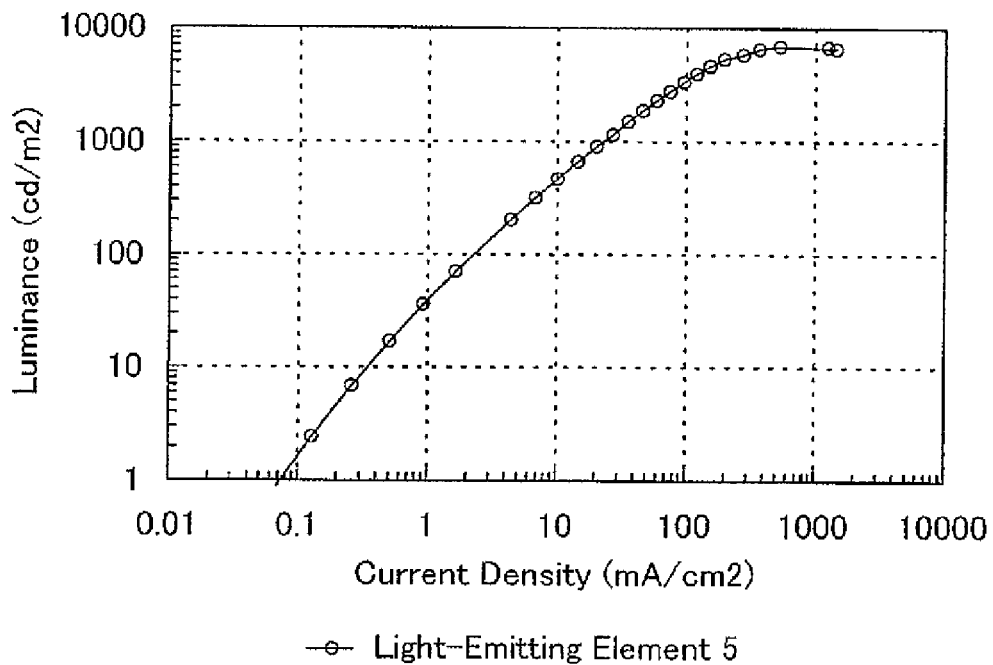
FIG. 51 is a graph showing current density vs. luminance characteristics of a light-emitting element manufactured in Embodiment 10.
Figure 52:
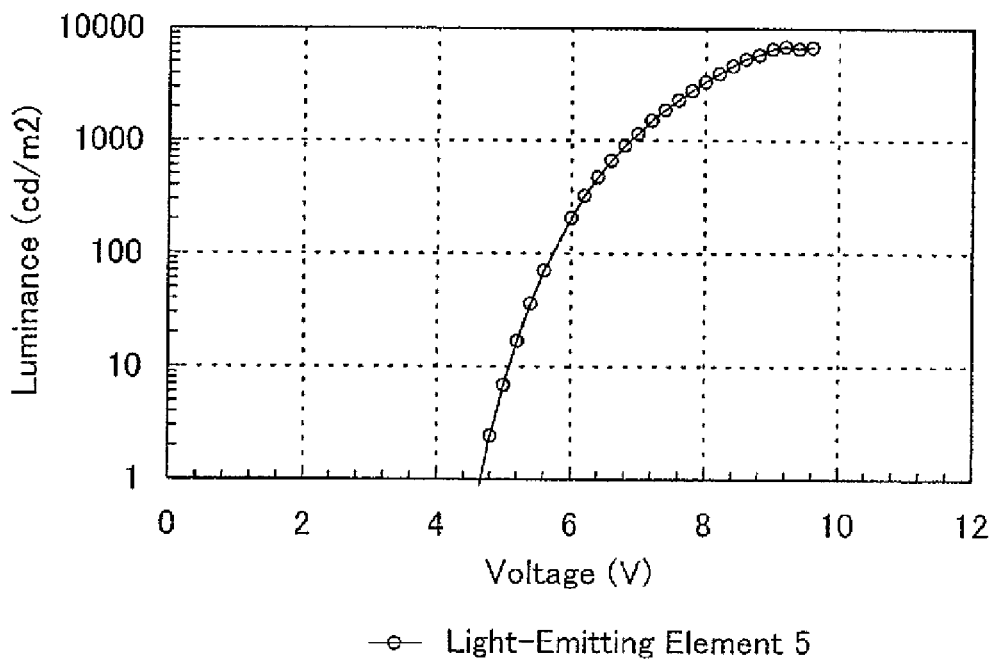
FIG. 52 is a graph showing voltage vs. luminance characteristics of a light-emitting element manufactured in Embodiment 10.
Figure 53:
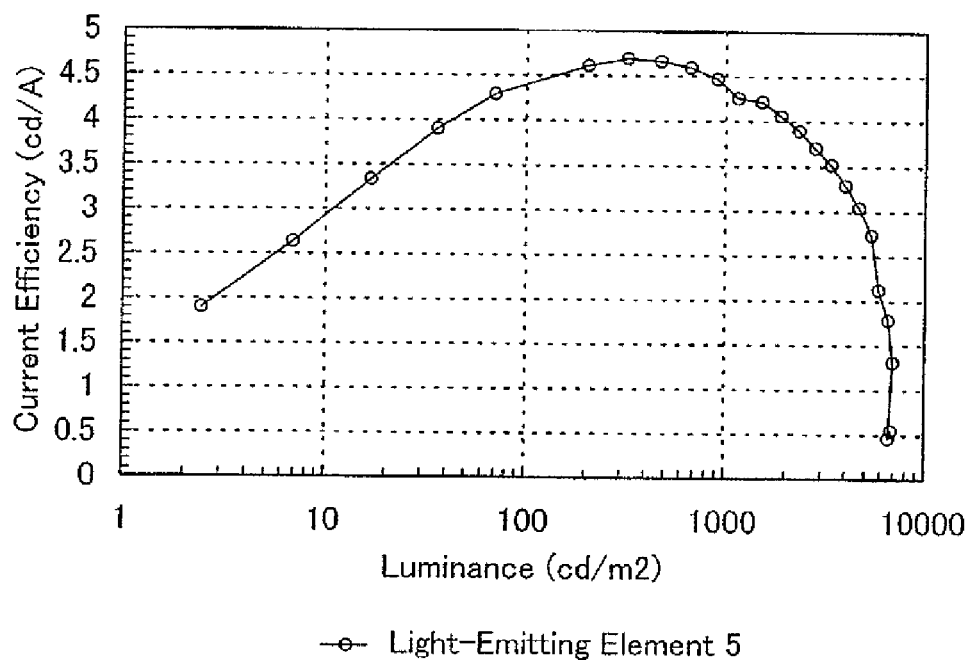
FIG. 53 is a graph showing luminance vs. current efficiency characteristics of a light-emitting element manufactured in Embodiment 10.
Figure 54:
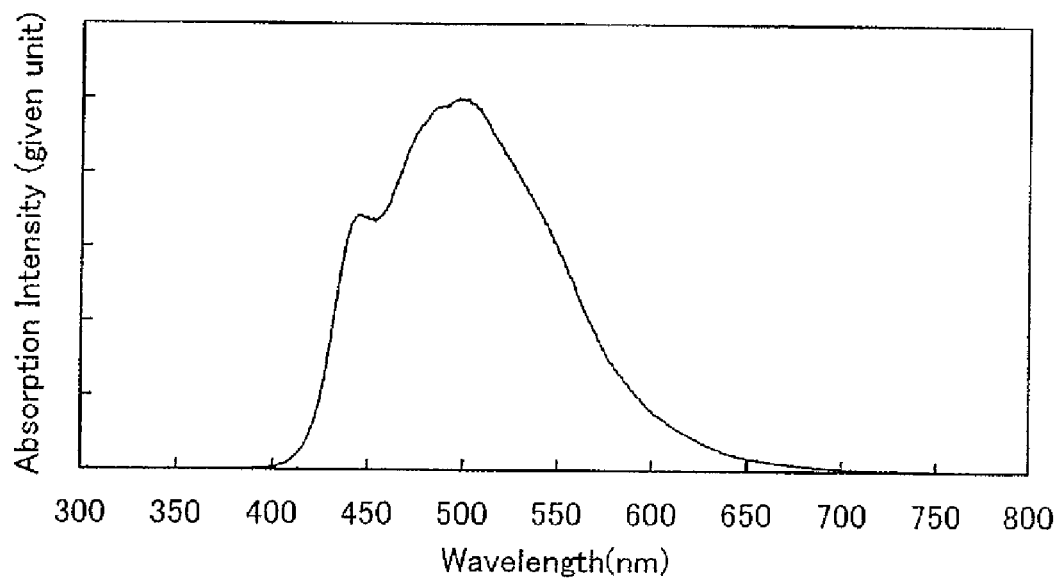
FIG. 54 is a graph showing an emission spectrum of a light-emitting element manufactured in Embodiment 10.

FIG. 51 shows current density vs. luminance characteristics of the light-emitting element 5, FIG. 52 shows voltage vs. luminance characteristics thereof, and FIG. 53 shows luminance vs. current efficiency characteristics thereof. Also, FIG. 54 shows the emission spectrum which was obtained at a current of 1 mA. A CIE chromaticity coordinate of the light-emitting element 5 at luminance of 907 cd/m$^2$ was (x=0.20, y=0.33), and light emission was light blue. Current efficiency at luminance of 907 cd/m$^2$ was 4.5 cd/A, and at that time, the voltage was 6.8 V and the current density was 20.3 mA/cm$^2$. In addition, as shown in FIG. 54, maximum emission wavelength at a current of 1 mA was 497 nm.

This application is based on Japanese Patent Application serial no. 2006-234639 filed in Japan Patent Office on Aug. 30, 2006, the entire contents of which are hereby incorporated by reference.

What is claimed is:

1. An anthracene derivative represented by structural formula (42):

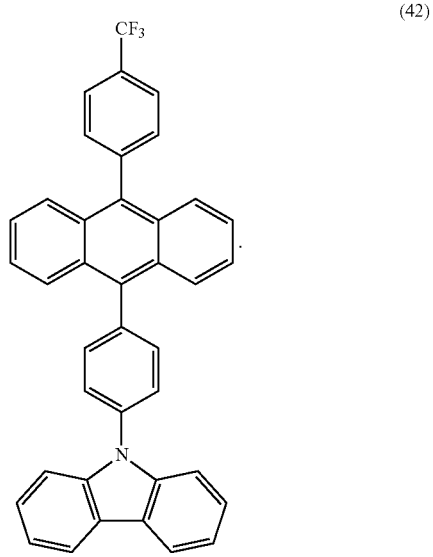

(42)

2. A light-emitting element comprising the anthracene derivative according to claim 1 between a pair of electrodes.

3. A light-emitting element comprising a light-emitting layer between a pair of electrodes,
wherein the light-emitting layer includes the anthracene derivative according to claim 1.

4. A light-emitting element comprising a light-emitting layer between a pair of electrodes,
  wherein the light-emitting layer includes the anthracene derivative according to claim 1, and
  wherein the anthracene derivative emits light.

5. A light-emitting device comprising:
  the light-emitting element according to claim 3; and
  a controller for controlling light emission of the light-emitting element.

6. An electronic device comprising a display portion,
  wherein the display portion is provided with a light-emitting element according to claim 3 and a controller for controlling light emission of the light-emitting element.

7. A lighting device comprising the light-emitting element according to claim 3.

* * * * *